United States Patent
Jain et al.

(10) Patent No.: US 11,393,592 B2
(45) Date of Patent: *Jul. 19, 2022

(54) NEXT BEST ACTION BASED BY QUANTIFYING CHRONIC DISEASE BURDEN ON A PATIENT AND THEIR WILLINGNESS TO TAKE THAT ACTION

(71) Applicants: Jawahar Jain, Los Altos, CA (US); Vishal Agarwal, Cupertino, CA (US); Lakshya Jain, Los Altos, CA (US); Saurabh Tara, Henderson, NV (US)

(72) Inventors: Jawahar Jain, Los Altos, CA (US); Vishal Agarwal, Cupertino, CA (US); Lakshya Jain, Los Altos, CA (US); Saurabh Tara, Henderson, NV (US)

( * ) Notice: Subject to any disclaimer, the term of this patent is extended or adjusted under 35 U.S.C. 154(b) by 292 days.

This patent is subject to a terminal disclaimer.

(21) Appl. No.: 16/862,490

(22) Filed: Apr. 29, 2020

(65) Prior Publication Data
US 2020/0258636 A1    Aug. 13, 2020

Related U.S. Application Data

(63) Continuation of application No. 16/217,888, filed on Dec. 12, 2018, now Pat. No. 10,930,398.

(60) Provisional application No. 62/597,818, filed on Dec. 12, 2017.

(51) Int. Cl.
G16H 50/30   (2018.01)
G16H 10/20   (2018.01)
G16H 40/60   (2018.01)

(52) U.S. Cl.
CPC ............ *G16H 50/30* (2018.01); *G16H 10/20* (2018.01); *G16H 40/60* (2018.01)

(58) Field of Classification Search
CPC ................................................ G06Q 50/20–26
See application file for complete search history.

(56) References Cited

U.S. PATENT DOCUMENTS

| | | | |
|---|---|---|---|
| 2014/0276549 A1* | 9/2014 | Osorio ................ | A61B 5/4803 604/503 |
| 2017/0228517 A1* | 8/2017 | Saliman ................ | G16H 10/20 |
| 2017/0372029 A1* | 12/2017 | Saliman ................ | G16H 10/60 |

* cited by examiner

*Primary Examiner* — Neal Sereboff
(74) *Attorney, Agent, or Firm* — Maschoff Brennan; Paul G. Johnson

(57) ABSTRACT

A method may include collecting sensor data and patient data. The method may include receiving input from a patient that provides a quantification of a present health risk assessment of the patient using minimum clicks in minimum categories using a VAS. The method may include receiving patient input including both manual input and sensor output in response to one or more questions directed to a quality of health of the patient. The method may include generating a CCB score with a pre-defined risk stratification. The CCB score may be based on at least two of the patient data, the sensor data, and the patient input. The method may include generating a CCB result. The CCB result may include the CCB score and a risk stratification of the patient based on the pre-defined risk stratification and the CCB score. The method may include providing a CCB result to a care-provider.

18 Claims, 16 Drawing Sheets

NEXT BEST ACTION BASED BY QUANTIFYING CHRONIC DISEASE BURDEN ON A PATIENT AND THEIR WILLINGNESS TO TAKE THAT ACTION

CROSS-REFERENCE TO RELATED APPLICATION

This application is a continuation of U.S. application Ser. No. 16/217,888 filed Dec. 12, 2018 which claims the benefit of and priority to U.S. Provisional App. No. 62/597,818 filed Dec. 12, 2017. The Ser. No. 16/217,888 application and the 62/597,818 application is each incorporated herein by reference.

FIELD

The embodiments discussed herein are related to leveraging graded escalation triage algorithm to quantify chronic disease burden on a patient and creating the next best action for the patient based on their willingness to that action.

BACKGROUND

Unless otherwise indicated herein, the materials described herein are not prior art to the claims in the present application and are not admitted to be prior art by inclusion in this section.

Chronic diseases have a significant impact on patients, offices of physicians, and hospitals. For example, on average forty five percent of Medicare patients will visit an emergency room in a twelve month period. Each visit to the emergency room may cost a patient around $3000 and consumes the time of both the patient and physicians that work in the emergency room. Similarly, the personal physician of the patient will perform a follow up visit to make sure the chronic disease is being properly treated after the visit to the emergency room by the patient. Prediction of onset of chronic diseases, and their management without conducting an in-person physician visit and/or without being overly burdensome on the patient and/or physician is a complex and expensive issue.

One aspect that makes management of chronic diseases, and prediction of an impact chronic diseases will have on a patient, so complex is the large number of physical, mental, and demographic factors that may be taken into account. Similarly, capturing data related to the physical and mental factors that impact managing chronic diseases and predicting the impact of chronic diseases on a patient is typically an arduous and drawn out process, which adds layers of complexity to managing chronic diseases and predicting the impact of chronic diseases on a patient. Likewise, existing methods for combining the available data are not simple, efficient, practical, nor easy to use, which adds yet another layer of complexity to managing chronic diseases and predicting the impact of chronic diseases on a patient.

Additionally, testing each patient that has one or more chronic diseases for different chronic diseases or changes to the previously diagnosed chronic diseases may be exorbitantly expensive to conduct. In some scenarios, the cumulative cost of testing every patient to detect the unhealthy cases may be so exorbitant that it outweighs the benefit, in terms of an increased quality adjusted life year, that it provides to the average patients.

The subject matter claimed herein is not limited to embodiments that solve any disadvantages or that operate only in environments such as those described above. Rather, this background is only provided to illustrate one example technology area where some embodiments described herein may be practiced.

BRIEF SUMMARY OF SOME EXAMPLE EMBODIMENTS

This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter.

Some embodiments described herein generally relate to efficient detection of chronic disease care burden.

In an example embodiment, a method to evaluate and stratify a chronic care burden of a patient may include collecting sensor data related to a quality of health of a patient that includes at least one of an activity level, a heart rate, a posture, a stress, a blood pressure variation, a blood glucose, a heart rhythm, a smoking status, a pain level, and a GPS data. The method may include collecting patient data that indicates at least one of a biological profile of the patient, a psychological profile of the patient, a social profile of the patient, physician notes related to the biological profile of the patient, physician notes related to the psychological profile of the patient, baseline of sensor based data, and physician notes related to the social profile of the patient. The method may include receiving input from the patient that provides a quantification of a present health risk assessment of the patient using minimum clicks in minimum categories using a visual analog scale (VAS). The method may include receiving patient input including both manual input and sensor output in response to one or more questions directed to a quality of health of the patient. The method may include generating a chronic care burden (CCB) score with a pre-defined risk stratification, wherein the CCB score is based on at least two of the patient data, the sensor data, and the patient input. The method may include generating a CCB result, wherein the CCB result includes the CCB score and a risk stratification of the patient based on the pre-defined risk stratification and the CCB score. The method may include providing a CCB result to a care-provider.

In another example embodiment, a system to evaluate and stratify a chronic care burden of a patient may include one or more sensors, an electronic health record (EHR) database, a chronic care burden (CCB) module, a questionnaire module, a memory, and a processor. The one or more sensors may be configured to collect sensor data related to a quality of health of a patient that includes at least one of an activity level, a heart rate, a posture, a stress, a blood pressure variation, a blood glucose, a heart rhythm, a smoking status, a pain level, and a GPS data. The EHR database may include patient data that indicates at least one of a biological profile of the patient, a psychological profile of the patient, a social profile of the patient, physician notes related to the biological profile of the patient, physician notes related to the psychological profile of the patient, baseline of sensor based data, and physician notes related to the social profile of the patient. The CCB module may be configured to receive both manual input and sensor output from the patient that provides a quantification of a present health risk assessment of the patient using minimum clicks in minimum categories using a VAS. The questionnaire module may be configured to receive patient input in response to one or more questions directed to a quality of health of the patient. The memory may be configured to store the sensor data, the EHR database, the patient input, and the quantification of the present health risk assessment of the patient. The processor may be coupled to the one or more sensors, the EHR database, the CCB module, the questionnaire module, and the memory. The processor may be configured to perform executable operations that include generating a CCB score with a pre-defined risk stratification, wherein the CCB score is based on at least two of the patient data, the sensor data, and the patient input. The operations may include generating a CCB result, wherein the CCB result includes the CCB score and a risk stratification of the patient based on the pre-defined risk stratification and the CCB score. The operations may include providing a CCB result to a care-provider.

These example embodiments are mentioned not to limit or define the disclosure, but to provide examples to aid understanding thereof. Additional embodiments are discussed in the Detailed Description, and further description is provided there. Advantages offered by one or more of the various embodiments may be further understood by examining this specification or by practicing one or more embodiments presented.

BRIEF DESCRIPTION OF THE FIGURES

These and other features, aspects, and advantages of the present disclosure are better understood when the following Detailed Description is read with reference to the accompanying drawings.

DETAILED DESCRIPTION

Figure 1:
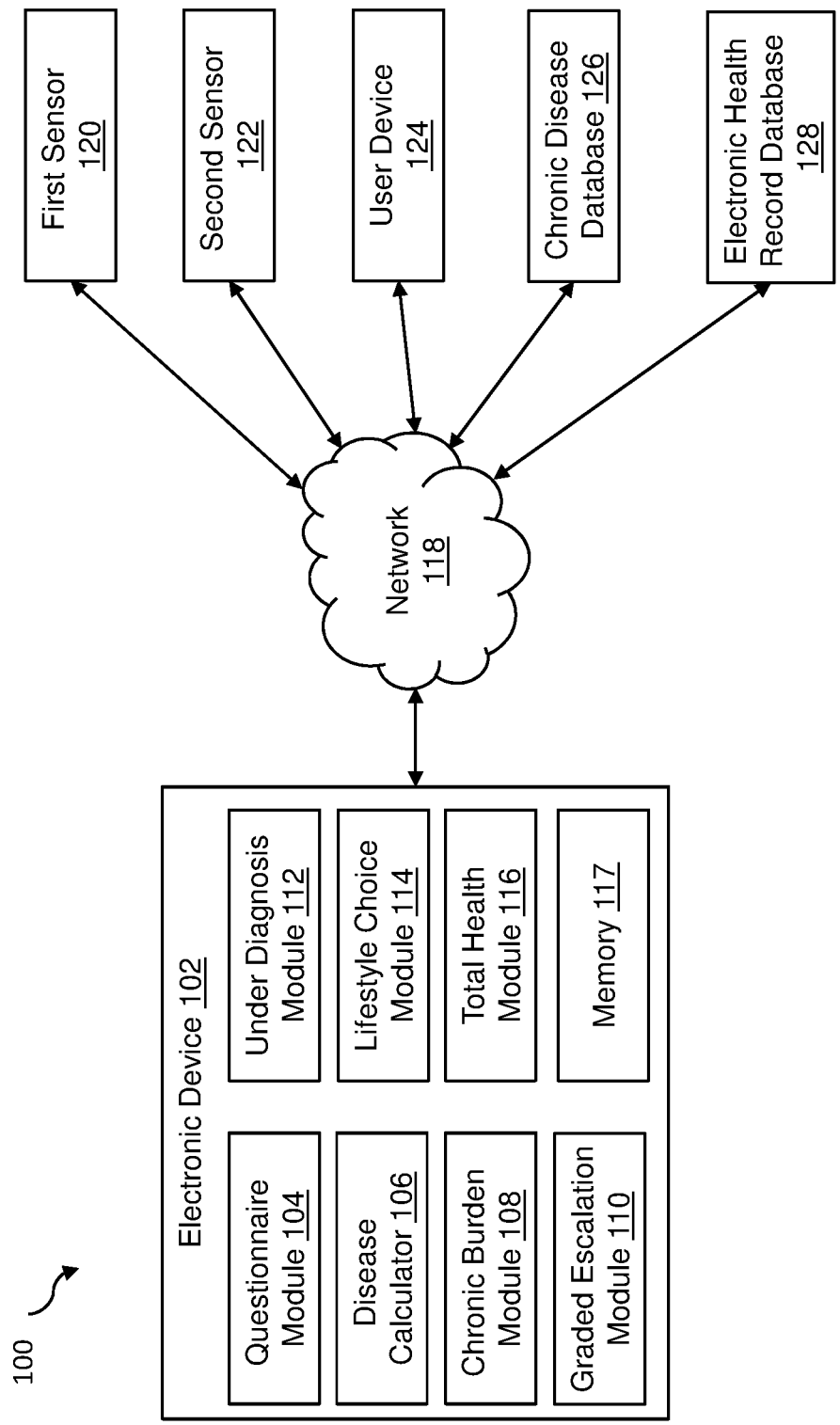
FIG. 1 is a block diagram of an example chronic care management system.

Several factors may affect management of chronic diseases and predicting an impact of chronic diseases on a patient. For example, there may be patient level factors (e.g., personality, psychological state, values, and/or preferences of the patient) along with environmental/community factors (e.g., psychological, social, and/or economic state of the community) that may have an impact. Likewise, there may be biological, physiological, and/or nonmedical factors of the patient that may have an impact. Clinical symptoms of the patient may be affected by the personality and/or psychological state of the patient; psychological state of the community; and/or the biological and/or physiological state of the patient. Additionally, physical and psychological function of the patient may be impacted by the clinical symptoms of the patient; the personality and/or psychological state of the patient; and/or the social and/or economic state of the community.

Similarly, general health perceptions of the patient may be affected by the physical and psychological function of the patient; the values and/or preferences of the patient; and/or the social and/or psychological state of the community. Likewise, overall quality of life of the patient may be affected by the general health perceptions of the patient; the values and/or preferences of the patient; the social and/or psychological state of the community; and/or various nonmedical factors. Some of these factors may vary depending on the age, gender, race, ethnicity, geographic location, and/or other demographic factors of the patient.

There are also several metrics that are available to determine the different factors discussed above. For example, the metrics may include a quality of wellbeing scale self-administered (QWB-SA), a health and activities limitation index (HALex), a short form six dimension (SF-6D), a health utilities index mark 2 (HUI2), a health utilities index mark 3 (HUI3), a euroQOl five dimension (EQ-5D), or any other acceptable metric for determining one or more of the factors that may affect management of chronic diseases and predicting an impact of chronic diseases on a patient.

Management of chronic diseases and predicting the impact of chronic diseases on the patient in a simple, efficient, and easy to use manner may be achieved by combining patient input that provides meaningful information related to the current health of the patient with additional data that is easy to measure, is credible, and can be readily obtained by a physician or their office. The combination of the different pieces of information may provide simple and efficient methods for determining a short-term health compliance (SHC) score, a chronic care burden (CCB) score, a lifestyle choice compliance (LCC) score, and/or a total health score of the patient. Additionally, combining the different pieces of information may provide simple and efficient methods for determining a risk of under diagnosis of one or more chronic diseases within a practice of the physician. Additionally, a large portion of the information may be obtained without the patient having to visit the physician in person.

Furthermore, combining the different pieces of information may provide both valid and reliable results that are easily understood by physicians and other people who use the results. Likewise, the results may be measurable over time and may be measurable for different geographic locations and/or demographics of patients. Additional factors that may be considered may include socioeconomic conditions, environmental conditions, or public policies that may impact the patient. Likewise, providing efficient and simple methods for obtaining the different pieces of information may reduce a standard error of patient data since patients may be tested more often (e.g., every two weeks) with a reduced burden on the patient.

In one embodiment, prediction of a patient with at least one chronic disease experiencing an acute event (e.g., visiting an emergency room (ER) and/or hospitalization) in the near future (e.g., within the next thirty to sixty days) may be performed. In some embodiments, prediction of a patient with at least one chronic disease experiencing an acute event in the intermediate future (e.g., in six to twelve months) may be performed. An electronic device may receive patient general health input in response to a general health questionnaire from a patient with at least one chronic disease. For example, the electronic device may receive the patient general health input indicating whether the patient would say that in general their health is excellent, very good, fair, or poor. As another example, the electronic device may provide an anatomically detailed avatar to the patient to allow the patient to provide a visual analog scale (VAS) pain scale score on a portion of the avatar related to pain being experienced by the patient. If the patient general health input indicates that, in general, their health is fair or poor, the electronic device may provide and/or administer a questionnaire about activity limitations, such as HALex questionnaire, to the patient via a user interface of the electronic device. Patient HALex input may be received in response to the HALex questionnaire. The patient HALex input may indicate whether the patient has recently experienced or is currently experiencing a limitation in activity. The electronic device may determine whether the patient is likely to experience an acute event in the near future (e.g., in thirty to sixty days) based on the patient general health input, the VAS pain scale, and/or the patient HALex input.

If the patient HALex input does not indicate that the patient has recently experienced or is currently experiencing a limitation in activity, the electronic device may provide and/or administer a health related quality of life (HRQOL) questionnaire to the patient. Patient HRQOL input may be received in response to the HRQOL questionnaire. The electronic device may determine whether the patient is likely to experience an acute event in the near future (e.g., the next thirty to sixty days) based on the patient general health input, the VAS pain scale, the patient HALex input, and/or the patient HRQOL input. In some embodiments, the electronic device may compare the patient HRQOL input to chronic data (e.g., chronic data included in a center for disease control and prevention (CDC) database and/or a national health interview survey (NHIS) database or other source) related to the one or more chronic diseases that impacts the patient. For example, the electronic device may compare the patient HRQOL input to the chronic data related to other patients that have similar demographic or geographic characteristics. The electronic device may provide the patient general health input, the patient HALex input, and/or the patient HRQOL input to the physician so that the physician can contact the patient to discuss the results of the various questionnaires or to schedule an in-person examination.

In an embodiment, prediction of a risk of a patient with at least one chronic disease experiencing a rise in a chronic care burden associated with one or more chronic disease (e.g., admission to an intensive care unit (ICU) and/or hospitalization) in the intermediate future (e.g., in six to twelve months) may be performed. In some embodiments, prediction of a risk of a patient with at least one chronic disease experiencing a rise in a chronic care burden associated with one or more chronic disease in the near future (e.g., within the next thirty to sixty days) may be performed. The electronic device may receive electronic health data record (EHR) data from the physician of the patient. The EHR data may include a list of chronic diseases of the patient (e.g., a patient clinic profile). Additionally, the EHR data may include a patient profile of the patient. In some embodiments, when a short-term period is event free, then with passage of time (almost up to two years), one may see a gradually diminishing and quantifiable contribution of risk from the factors contributing to short term risk. On the other hand, with passage of time one may see gradually increasing and quantifiable contribution of risk from the factors contributing to the chronic care burden.

The risk of the patient experiencing a rise in the chronic care burden associated with chronic diseases may be adjusted based on hazards that are included in the patient profile. For example, the patient profile may include a hazard score which reflects the chronic care burden associated with patient's diseases profile and patient's socioeconomic profile. If the patient profile suggest a hazard, the electronic device may provide an alert to the physician indicating that the patient has increasing likelihood to experience an acute event in the near future. The electronic device may determine the chronic care burden of the patient based on the EHR data, and/or responses to questionnaires. Additionally, or alternatively, the chronic care burden may be further based on a disease score obtained using a disease calculator.

In an embodiment, risk prediction can be made for an impact that the lifestyle choices of the patient may have on their chronic diseases. The electronic device may receive patient lifestyle input in response to a healthy lifestyle and personal control questionnaire (HLPCQ). The patient lifestyle input may include data related to dietary health choices, dietary harm avoidance, daily routine, organized physical exercise, and/or social and mental balance of the patient. The electronic device may store a database of statistically significant number of similar and comparable patients and using that it may determine the impact the various lifestyle choices of the patient may have on the chronic diseases of the patient. The electronic device may determine a lifestyle choice compliance (LCC) score based on the patient lifestyle input. Additionally, the electronic device may determine one or more lifestyle changes (e.g., lifestyle prescriptions) that the patient should make to reduce the impact the current lifestyle choices of the patient have. The electronic device may provide a list of the lifestyle changes to the patient and/or the physician.

In an embodiment, a total health score of the patient may be determined. The total health score may indicate an overall health of the patient and areas of health that are a concern to the physician. The electronic device may determine the total health score based on the SHC score, the CCB score, and the LCC score. The SHC score may be based on the prediction of the patient experiencing an acute event in the near future. The CCB score may be based on the prediction of the risk of the patient with at least one chronic disease experiencing a rise in the chronic care burden. Also, the LCC score may be based on the prediction of the impact lifestyle choices of the patient may have on their chronic diseases. Each portion of the total health score may be weighted equally. Alternatively, one or more portions of the total health score may be weighted differently than one or more other portions. The total health score may provide quantified guidance to the patient and/or the physician with regards to the short-term health, the chronic burden, and/or the lifestyle impact on chronic diseases of the patient.

In an embodiment, a possible under diagnosis of one or more chronic diseases within a practice of a physician may be determined. The electronic device may receive the EHR data from the office of the physician. The EHR data may indicate a percentage of patients that are diagnosed with one or more chronic diseases in the office of the physician. The electronic device may also receive the chronic data related to one or more chronic diseases. The chronic data may indicate a percentage of patients in a similar geographic region and/or with similar demographic characteristics that are diagnosed with the same chronic diseases. The percentage of patients that are diagnosed with the chronic diseases that are included in the EHR data may be compared to the percentage of patients that are diagnosed with the same chronic diseases that are included in the chronic data. If a difference between the two sets of data is outside a threshold diagnosis value range, the electronic device may provide an alert to the physician indicating that the percentage of patients in the EHR data is not the same or similar to the percentage of patients in the chronic data and the physician may want to evaluate why the difference exists. The threshold value range may be adjusted based on the hazards identified in the input data.

Being able to better manage chronic diseases and predict impact of chronic diseases on a patient may improve the quality of life of the patient and reduce financial burdens associated with treating chronic diseases.

FIG. 1 is a block diagram of an example chronic care management (CCM) system 100 (hereinafter "system 100"), arranged in accordance with at least one embodiment described herein. As depicted in FIG. 1, the system 100 may include an electronic device 102, a network 118, a user device 124, a chronic disease database 126, and an electronic health record (EHR) database 128. Additionally, the system 100 may include one or more sensors. For example, the system 100 may include a first sensor 120 and a second sensor 122 (collectively referred to herein as the sensors 120 and 122). While two sensors 120 and 122 are shown in FIG. 1, more generally the system 100 may include one sensor 120 or 122, may not include a sensor 120 or 122, or may include more than two sensors 120 and 122.

The electronic device 102 may include a computer-based hardware device that includes a processor, memory, and communication capabilities. The electronic device 102 may be coupled to the network 118 to communicate data with any of the other components of the system 100. Some examples of the electronic device 102 may include a mobile phone, a smartphone, a tablet computer, a laptop computer, a desktop computer, a set-top box, a virtual-reality device, a connected device, or other suitable electronic device. The electronic device 102 may include a processor-based computing device. For example, the electronic device 102 may include a hardware server or another processor-based computing device configured to function as a server. The electronic device 102 may include memory and network communication capabilities.

The network 118 may include any communication network configured for communication of data and/or signals between any of the components (e.g., 102, 120, 122, 124, 126, and/or 128) of the system 100. The network 118 may be wired or wireless. The network 118 may have numerous configurations including a star configuration, a token ring configuration, or another suitable configuration. Furthermore, the network 118 may include a local area network (LAN), a wide area network (WAN) (e.g., the Internet), and/or other interconnected data paths across which multiple devices may communicate. In some embodiments, the network 118 may include a peer-to-peer network. The network 118 may also be coupled to or include portions of a telecommunications network that may enable communication of data in a variety of different communication protocols.

In some embodiments, the network 118 may include or may be configured to include a BLUETOOTH® communication network, a Z-Wave® communication network, an Insteon® communication network, an EnOcean® communication network, a wireless fidelity (Wi-Fi) communication network, a ZigBee communication network, a HomePlug communication network, a Power-line Communication (PLC) communication network, a message queue telemetry transport (MQTT) communication network, a MQTT-sensor (MQTT-S) communication network, a constrained application protocol (CoAP) communication network, an extensible messaging and presence protocol (XMPP) communication network, a cellular communications network, any similar communication networks, or any combination thereof for sending and receiving data. The data communicated in the network 118 may include data communicated via short messaging service (SMS), multimedia messaging service (MMS), hypertext transfer protocol (HTTP), direct data connection, wireless application protocol (WAP), e-mail, smart energy profile (SEP), ECHONET Lite, OpenADR, or any other protocol that may be implemented with the electronic device 102, the sensors 120 and 122, the user device 124, the chronic disease database 126, the EHR database 128, a cloud server communication, and/or a gateway.

One or more of the sensors 120 and 122 may include any type of sensor to gather sensor data related to a physical state of a patient. For example, one or more of the sensors 120 and 122 may include a global positioning system (GPS) sensor, an accelerometer sensor, a pedometer sensor, a heart rate (HR) sensor, a blood pressure (BP) sensor, a blood glucose sensor, an electromyography (EMG) sensor, an electrocardiogram (ECG) sensor, an electroencephalography EEG sensor, a Galvanic Skin Response (GSR) sensor, a photoplethysmography (PPG) sensor, a temperature sensor, a sleep sensor, a posture sensor, a respiration sensor, a cardiac output sensor, a ballistocardiography (BCG) sensor, a stress sensor, an emotion sensing system, or any other sensor to detect and/or gather data about a physical state of the patient. Alternatively or additionally, one or more of the sensors 120 and 122 may include any type of sensor to gather sensor data related to a mental state of the patient. For example, one or more of the sensors 120 and 122 may detect emotional resilience, tiredness, mood, or any other mental state of the patient. In some embodiments, one or more of the sensors 120 and 122 may include on-body (e.g., wearable) devices and/or off-body (e.g., non-wearable) devices.

The interpretation of sensor data may depend on a baseline and hence may be adjusted based on different factors. For example, the interpretation of sensor data may be adjusted based on an age, a race, a gender, an ethnicity, a health state, a health need, or any other appropriate patient based factor that may affect the health of the patient. Additionally, the interpretation of sensor data may be adjusted based on when the sensor data is gathered such as for different months, days, seasons, or any other appropriate time based factor that may affect the health of the patient.

The sensor data may permit quantification of health habits in terms of activity, sleep, stress, posture, outdoor time, regularity of routine, number of cigarettes per day, number of times fast food is consumed, or number of times alcohol is consumed or a restaurant that serves alcohol is visited, what type of food is being consumed (e.g., amounts of salt, sugar, trans-fat, or alcohol) of the patient. Alternatively or additionally, the sensor data may permit quantification of blood pressure, heart rate, heart rate variability, cardiac output, oxygen saturation, emotion markers, or pain markers of the patient. Furthermore, the sensor data may include data indicating interaction of the patient with a smartphone or similar device, which may permit quantification of a social life of the patient. The sensor data may be used to verify the various health scores discussed in the present disclosure, which may obviate exaggerated or understated health concerns of the patient.

In some embodiments, the sensor data may permit responses to questionnaires to be obtained using the sensor data. The sensor data may be used to generate patient profiles for various categories to which the patient belongs. Additionally, the sensor data may be used to determine whether the patient is deviating from standard norms of the patient.

The chronic disease database 126 may include any computer-based source for collecting and/or storing chronic data related to patients that have one or more chronic diseases (e.g., arthritis, diabetes, epilepsy, heart disease, chronic obstructive pulmonary disease (COPD), asthma, cancer, cardiovascular disease, or any other chronic disease). In some embodiments, the chronic disease database 126 may include a sufficiently large and publicly available database (such as CDC database and/or an NHIS database). The chronic data may be broken down into statistical data sets based on regions, states, counties, and/or cities of patients included in the chronic data. For example, the chronic data related to patients that have diabetes may be broken down into data sets that include all patients located in an entire region such as the entire Pacific Northwest, patients located in all of a single state such as Washington, patients located only in one county of the state such as King County, or patients located just in one city, town, or metropolitan area such as Seattle.

The chronic data may include psychophysiological, physiological, healthcare choices, lifestyle choices, and/or social profiles of the different patients included in the chronic data. Likewise, the chronic data may include patient responses to various health related questionnaires, such as a HRQOL, HALex, patient healthcare questionnaire 2 (PHQ2), or any other health related questionnaires. The patient responses then may be stored as patient HRQOL input, patient HALex input, and/or patient PHQ2 input. The chronic data may also include sensor data, such as the sensor data gathered by the sensors 120 and 122.

The patient HRQOL input may include a perceived overall quality of life of the patient by determining a state of physical and/or mental health of individual patients or a group of patients. The patient HRQOL input may also include VAS based quantification of broad multidimensional subjective evaluations of both positive and negative aspects of the life of patients. The patient HRQOL input may be related to chronic diseases and/or risk factors of the patients. For example, the patient HRQOL input may include a list of chronic diseases each patient has been diagnosed with along with any risk factors that may affect the chronic diseases of the patients. Risk factors may include body mass index (BMI), physical inactivity, smoking, alcohol and/or other risk factors.

The data regarding functional limitation (patient activity limitation data such as HALex input) may indicate limitation of activity of the patients included in the chronic data. For example, the patient HALex input may indicate whether the patients are receiving help with daily tasks such as grooming, getting dressed, eating, or other activities though previously these were being done unassisted. The patient HALex input may also include a database which may have data for a similar group of patients across a wide range of regions. For example, the patient HALex input may be collected and analyzed by city, state, and/or region that the different patients reside within.

The patient PHQ2 input may indicate PHQ2 depression score of the patients along with in the context of the patient's depression especially the historic pattern. For example, the patient PHQ2 input may indicate whether the patients are experiencing worsening depression or not. The patient PHQ2 input may be adjusted based on factors that may affect depression. For example, the patient PHQ2 input may be adjusted based on a season, time of day, recent life experiences, or other data.

The EHR database 128 may include any computer-based source for patient data (e.g., EHR data) related to patients that visit an office of a physician associated with the EHR database 128. The EHR data may include information gathered during examination by physicians or staff at the office of the physician. The EHR data may include patient data that indicates at least one of a biological profile of the patient, a psychological profile of the patient, a social profile of the patient, physician notes related to the biological profile of the patient, physician notes related to the psychological profile of the patient, and physician notes related to the social profile of the patient. Additionally, the EHR data may include data related to clinical symptoms such as COPD of the patients; risk factors such as BMI and BP of the patients; extenuating factors such as pain of the patients; and psychosocial factors such as financial status of the patients. The EHR data may be combined with the sensor data to determine responses to questionnaires without the patient providing additional information. Using the sensor data combined with the EHR data to determine responses to the questionnaires without the patient providing additional information may reduce overhead associated with providing the questionnaires and/or storing information related to the questionnaires and may also improve the patient's experience by reducing and/or eliminating the patient's attentive involvement in responding to the questionnaires, e.g., the patient may be involved by going about the patient's regular activities while the sensor(s) collect data without otherwise having to take time to attentively respond to questionnaires.

The user device 124 may include a computer-based hardware device that includes a processor and communication capabilities. The user device 124 may be coupled to the network 118 to communicate data with any of the other components of the system 100. For example, the user device 124 may communicate with the electronic device 102 to provide data or receive data related to the patient. Some examples of the user device 124 may include a mobile phone, a smartphone, a tablet computer, a laptop computer, a desktop computer, a set-top box, a virtual-reality device, a connected device, or other user device. The user device 124 may include a processor-based computing device. For example, the user device 124 may include a hardware server or another processor-based computing device configured to function as a server.

The user device 124 may also include an interface for facilitating communication with the patient. For example, the interface may be configured to communicate with external devices such as input devices (e.g., keyboard, mouse, pen, voice input device, touch input device, and/or others), or the sensors 120 and 122. Alternatively or additionally, the user device 124 may include an integrated input device to receive input from the patient, such as a touchscreen display, a virtual keyboard, or other input device.

The electronic device 102 may include a computer-based hardware device that includes a processor and communication capabilities. The electronic device 102 may be coupled to the network 118 to communicate data with any of the other components of the system 100. Some examples of the electronic device 102 may include a mobile phone, a smartphone, a tablet computer, a laptop computer, a desktop computer, a set-top box, a virtual-reality device, a connected device, or other electronic device. The electronic device 102 may include a processor-based computing device. For example, the electronic device 102 may include a hardware server or another processor-based computing device configured to function as a server. The electronic device 102 may include a questionnaire module 104, a disease calculator 106, a chronic burden module 108, a graded escalation module 110, an under diagnosis module 112, a lifestyle choice module 114, a total health module 116, and a memory 117. Although not depicted in FIG. 1, the electronic device 102 may additionally include one or more processors and/or communication interfaces.

The memory 117 may include computer-readable storage media for collecting or storing data thereon. For example, the memory 117 may include computer-readable storage media that may be tangible or non-transitory computer-readable storage media such as Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other tangible and non-transitory storage medium which may be used to store data that may be accessed by a general-purpose or special-purpose computer.

The memory 117 may store various data in any data structure, such as a relational database structure. For example, the memory 117 may include collected data obtained from one or more of the sensors 120 and 122, the user device 124, the chronic disease database 126, and/or the EHR database 128.

The questionnaire module 104 may include software executable by or on the electronic device 102. For example, the questionnaire module 104 may include code stored on the electronic device 102 that may be executed line-by-line by the processor of the electronic device 102 and/or may be loaded into the memory 117 and executed by the processor of the electronic device 102 to perform or control performance of one or more operations described herein in connection with the questionnaire module 104. Alternatively or additionally, the questionnaire module 104 may be implemented in hardware, e.g., as an application specific integrated circuit (ASIC), a field programmable gate array (FPGA), or other hardware device configured to perform or control performance of one or more operations described herein in connection with the questionnaire module 104.

The questionnaire module 104 may be configured to provide one or more health related questionnaires to the patient via user device 124. For example, the questionnaire module 104 may provide the HALex, PHQ2, a healthy lifestyle and personal control questionnaire (HLCPQ), HRQOL, and/or any other appropriate health based questionnaires. Alternatively or additionally, the questionnaire module 104 may provide a euroQOl five dimension (EQ-5D-3L), a health utilities index mark 2 (HUI2), a health utilities index mark 3 (HUI3), a short form six dimension (SF-6D), and/or quality of well-being scale questionnaires, and/or other suitable questionnaires. The identification, selection, and/or timing of the administration/provision of the questionnaire(s) to the patient via user device 124 may be controlled by the chronic burden module 108, the graded escalation module 110, the lifestyle choice module 114, and/or the total health module 116.

In some embodiments, the questionnaire to assess the functional activity limitation, such as HALex questionnaire, may include one or more questions directed to a functional status or limitation of activity of the patient. Questions in the HALex questionnaire may include: "Because of a physical, mental, or emotional problem do you need the help of other persons with your personal care needs, such as eating, bathing, dressing, or getting around inside the home?" "Because of a physical, mental, or emotional problem do you need the help of other persons in handling routine needs, such as everyday household chores, doing necessary business, shopping, or getting around for other purposes?" "Does a physical, mental, or emotional problem now keep you from working at a job or business?" "Are you limited in the kind or amount of work you do because of physical, mental, or emotional problems?" and "Are you limited in any way in any activities because of the physical, mental, or emotional problems?", and/or other suitable questions about a functional status or limitation of activity of the patient.

In some embodiments, the HRQOL questionnaire may include one or more questions directed to general health factors that encompass one or both of physical and mental health of the patient. Questions in the HRQOL questionnaire may include: "Would you say that in general your health is excellent, very good, good, fair, or poor?" "Now thinking about your physical health, which includes physical illness and injury, for how many days during the past thirty days was your physical health not good?" "Now thinking about your mental health, which includes stress, depression, and problems with emotions, for how many days during the past thirty days was your mental health not good?" and "During the past thirty days, for about how many days did poor physical or mental health keep you from doing your usual activities, such as self-care, work, or recreation?", and/or other suitable questions about general health factors that may encompass one or both of physical and mental health of the patient.

In some embodiments, the HLCPQ questionnaire may include one or more questions directed to lifestyle choices of the patient. The HLCPQ questionnaire may include one or more subjects related to lifestyle choices of the patient. For example, the one or more subjects may include dietary health choices, dietary harm avoidance, daily routine, organized physical exercise, social and mental balance, and/or risk taking choices of the patient. Questions in the dietary health choices of the patient may include: ""Do you carefully control the amount of food on your plate at mealtime?" ?" "Do you check the food labels before buying a product?" "Do you calculate the calories of your meals?" "Do you limit fat in your meals?" "Do you limit meat in your diet?" and "Do you feel you eat sufficient amount of fruits and vegetables?", and/or other suitable questions about dietary health lifestyle choices of the patient.

In some embodiments, questions in the dietary harm avoidance of the patient may include "Do you eat pre-packed, frozen or fast food?" "Do you avoid soft drinks?" ""Do you change your eating habits when stressed or disappointed?" "Do you overeat when eating out with friends?", "In a typical week, do you eat most of your [all your] meals at around the same time?". "Are you careful about not missing a meal each day?", "Do you eat a nutritionally balanced breakfast?", and/or other suitable questions about dietary harm avoidance lifestyle choices of the patient. Questions in the daily routine of the patient may include: "Do you have a regular schedule you follow every day?" "Do you sleep at around the same time each day?" "Do you eat breakfast at the same time each day?" "Do you eat lunch at the same time each day?" and "Do you eat dinner at the same time each day?", and/or other suitable questions about daily routine lifestyle choices of the patient.

In some embodiments, questions in the organized physical exercise of the patient may include: "Do you undertake moderate or rigorous physical activities for at least one hundred minutes per week?" and "Do you exercise in an organized/regular manner?", and/or other suitable questions about organized physical exercise lifestyle choices of the patient. Questions in the social and mental balance of the patient may include: "Do you use any support system of friends and/or family when you face a personal problem or worry?" "When going through difficulties, do you try to remain optimistic or concentrate on positive thoughts?" "Do you consciously try to relax before sleeping?" "Do you care about meeting and discussing with your family on a daily basis?" and "Do you balance your time between work, personal life, and leisure?", and/or other suitable questions about social and mental balance lifestyle choices of the patient.

In some embodiments, questions in the risk-taking choices of the patient may be treated differently. The patient's response for the questions in the risk taking questionnaire may be used to scale his score obtained from the rest of the HLPCQ survey. The risk taking questionnaire may include: "Do you smoke? If Yes, then how many cigarettes a day?" "Do you consume alcohol? If so, how many servings a day?" "Do you get exposed to significant pollution besides during commute? If so then for how many minutes per day?" "Do you have a congested commute by road? If so then for how many minutes per day?" "Do you use sunscreen or take measures to protect yourself from direct (afternoon) sun?" and "Do you ever skip medications? If so, how many times a week?", and/or other suitable questions about risk taking lifestyle choices of the patient.

The HLPCQ questions can be used to compute behavioral score of the patient, dubbed as BICO score (Behavior Index Comprehensive ScOre).

The questions may be categorized into 6 categories namely C1, C2, C3, C4, C5 and C6. A particular question can belong to only one category but one category can have multiple question. The answer to each question may be given one of the following weights 0, 1.25, 2, 5, 3.75 or 5. The answer to each may be stored in variable $A_{ij}$, where i is one of the 6 categories and j is a particular question in the category i. When all the questions are answered, a score may be calculated as follows: $C_i=\Sigma(A_{ij})$ where i=1 to 6 representing each category and j=1 to n with n being the number of questions in that category. Once the score for each category is calculated the behavior score, BICO, may be calculated by appropriately combining the scored categories. For example, one method of combining the categories adds all category scores except the risk taking category, and multiplies the resulting value with appropriately weighted risk taking factor. One embodiment of such a method is the following formula: BICO=(C1+C2+C3+C4+C5)*(1−C6/20+R)*100/88. Here R is a regularization factor that allows the risk factor to appropriately scale the composite value obtained from all other categories. In the formula described above, R is given a value of 0.1.

In some embodiments, the questions that lead to computation of lifestyle choices may be determined using input from the sensors. For example, one can use sensors that can analyze the quantity and the quality of the patient's diet. For example, sensors that use accelerometer in a smart glass or anywhere in an upper torso of the patient that can detect the chewing of the user help analyze the dietary dimensions. Sensors which work by analyzing the image of food and quantity of food left after the meal are additional such approaches. One can also use sensors that analyze whether a person is smoke free and the frequency of possible smoking as is already known in the published state of the art. One can also use sensors including GPS that analyze the extent of exposure to pollution. One can also use sensors that determine the regularity of the schedule which simply look at the type of activities, time and duration of sleep, location as function of time and calendar, time and extent of eating, to determine the regularity of the lifestyle. One can also combine the above lifestyle choice calculating modules with stress and emotion detection to quantify the patient's lifestyle choices. One can also combine the above lifestyle choice calculating modules with speech recognition to further quantify the patient's lifestyle choices. One can also combine a breath analyzer with the above sensing modalities to further quantify the extent of alcohol a patient drinks.

In some embodiment, the patient response is auto-filled via the sensor input as described above and then validated by the patient. In some embodiment, the sensor derived input(s) can over-ride the patient provided input(s). In some embodiment, the patient response is taken as the weighted average of sensor derived input and the patient derived input. In some other embodiment, the patient credibility is given a weightage by the care-provider which is used to create the composite patient response by combining patient provided input and input derived via sensor. In some embodiment, the physician is provided patient sensor value that can be compared to patient's response to determine the veracity of the patient's response, and hence create the patient credibility. In some embodiment, the physician is provided a range of credibility weightage to provide to the patient-derived input so that a range of scores are computed for the patient and based on the physician's clinical assessment he can empirically determine the credibility weightage.

In some embodiment, for each response the patient provides, he is asked a set of questions specific to that response to validate the patient provided inputs and guide him to make the correct assessment. For example, suppose a patient is asked if he needs help to do the daily tasks of living. Now, if his response is YES but it is due to a mistaken understanding of what it means to get help to get dressed then the additional questions serve to clarify his input.

In some embodiment, the sensor derived input is calibrated by a statistical analysis of the expected value from a matching set of users. In some embodiment, the sensor derived input is calibrated by a statistical analysis of the expected value from a matching set of users as determined by the physician with or without an analysis of the statistical information.

In some embodiments, the questionnaire module 104 may include a general state of health of the patient question, which may include "Would you say that in general your health is excellent, very good, good, fair, or poor?"

The user device 124 may display the questionnaires to the patient, one at a time or two or more simultaneously. The patient may provide responses (e.g., patient input) to the questionnaires via the one or more input devices coupled to the user device 124. The user device 124 may provide the patient input to the electronic device 102 via the network 118. The patient input may be stored in the memory 117 for further manipulation or later access by the electronic device 102.

The disease calculator 106 may include software executable by or on the electronic device 102. For example, the disease calculator 106 may include code stored on the electronic device 102 that may be executed line-by-line by the processor of the electronic device 102 and/or may be loaded into the memory 117 and executed by the processor of the electronic device 102 to perform or control performance of one or more operations described herein in connection with the disease calculator 106. Alternatively or additionally, the disease calculator 106 may be implemented in hardware, e.g., as an ASIC, an FPGA, or other hardware device configured to perform or control performance of one or more operations described herein in connection with the disease calculator 106.

The disease calculator 106 and/or the questionnaire module 104 may be configured to provide one or more disease calculator questionnaires about one or more chronic diseases to the patient via the user device 124. For example, the disease calculator 106 and/or the questionnaire module 104 may provide one or more disease calculator questionnaires. An example, is the questionnaires available at https://www.adma.org.au/clearinghouse.html at least as of Dec. 12, 2017 and/or the disease calculator 106 may be implemented as any of the calculators available at the same source. As another example, the disease calculator 106 and/or the questionnaire module 104 may provide one or more disease calculator questionnaires available at https://siteman.wustl.edu/prevention/ydr/ or https://reference.medscape.com/guide/medical-calculators at least as of Mar. 28, 2018 and/or the disease calculator 106 may be implemented as any of the calculator available at the same source. Alternatively or additionally, the disease calculator 106 may determine a chronic disease calculator score based on patient responses to the one or more questionnaires.

The user device 124 may display the disease calculator questionnaires to the patient. The patient may provide responses (e.g., disease calculator patient input) to the disease calculator questionnaires via one or more input devices coupled to the user device 124. The user device 124 may provide the disease calculator patient input to the electronic device 102 via the network 118. The disease calculator patient input may be stored in the memory 117 for further manipulation or later access by the electronic device 102. The identification, selection, and/or timing of the administration/provision of disease calculator questionnaires to the patient via the user device 124 may be controlled by the chronic burden module 108, the graded escalation module 110, the lifestyle choice module 114, and/or the total health module 116.

The graded escalation module 110 may include software executable by or on the electronic device 102. For example, the graded escalation module 110 may include code stored on the electronic device 102 that may be executed line-by-line by the processor of the electronic device 102 and/or may be loaded into the memory 117 and executed by the processor of the electronic device 102 to perform or control performance of one or more operations described herein in connection with the graded escalation module 110. Alternatively or additionally, the graded escalation module 110 may be implemented in hardware, e.g., as an ASIC, an FPGA, or other hardware device configured to perform or control performance of one or more operations described herein in connection with the graded escalation module 110.

The graded escalation module 110 may be configured to determine short-term triage of the patient based on factors that may include responses by the patient to one or more questionnaires. Similarly, the graded escalation module 110 may be configured to predict a likelihood of the patient experiencing an acute event (e.g., visiting an emergency room (ER) and/or hospitalization) in the near future based on changes in short-term health aspects of the patient. The likelihood of the patient experiencing an acute event in the near future may be determined based on the patient input (e.g., the patient responses to the questionnaires provided by the questionnaire module 104 and/or the disease calculator questionnaires provided by the disease calculator 106). Alternatively or additionally, the likelihood of the patient experiencing an acute event in the near future may be determined based on the chronic data included in the chronic disease database 126 and/or the EHR data included in the EHR database 128.

For example, the likelihood of the patient experiencing an acute event in the near future may be determined based on a number of unhealthy days of the patient and/or an amount of pain the patient is currently experiencing. As another example, the likelihood of the patient experiencing an acute event in the near future may be determined based on the number of unhealthy days of the patient, patient functional activity limitation input, such as HALex input, and/or the amount of pain the patient is currently experiencing which can be input using a VAS (visual analog scale) that is calibrated, for example, between 0 to 10, or between 0 to 100. As yet another example, the likelihood of the patient experiencing an acute event in the near future may be determined based on the number of unhealthy days of the patient, the patient HALex input, the amount of pain the patient is currently experiencing, and/or patient PHQ2 input. Alternatively, the likelihood of the patient experiencing an acute event in the near future may be determined based on the patient HALex input and/or patient general health input.

The graded escalation module 110 may determine the likelihood of the patient experiencing an acute event in the near future without the patient having to visit an office of the physician.

In some embodiments, the graded escalation module 110 may provide an anatomically detailed human avatar (referred to herein as 'avatar') to the patient via the user device 124. The avatar may allow the patient to enter the amount of pain the patient is experiencing, where that patient is experiencing pain, and/or whether the pain is musculoskeletal or visceral organ by using a visual analog scale (VAS) pain scale. The amount of pain the patient is experiencing, where that patient is experiencing pain, and/or whether the pain is musculoskeletal or visceral organ may be stored as a VAS score. The VAS score may be received from the user device 124 by the electronic device 102 and stored in the memory 117. Alternatively or additionally, the VAS score may be received from the user device 124 by the graded escalation module 110. The graded escalation module 110 may be configured to determine an etiology of pain of the patient using the avatar.

In some embodiments, the graded escalation module 110 may direct the questionnaire module 104 to provide one or more questions to the patient via the user device 124 in response to the patient indicating that they are experiencing pain or discomfort in one or more regions of the body. For example, the questionnaire may include a somatic symptom questionnaire. The questions may be directed to what type of pain or discomfort the patient is experiencing and its intensity or any other appropriate question related to the pain or discomfort of the patient with respect to the region of the body under question. A patient response to the one or more questions along with a current VAS score may be collected and stored as VAS data (e.g., a two-dimensional VAS pain or discomfort scale)

In some embodiments, the VAS score may be judged relative to a previous score or a standard score. This can happen if the patient has previously been diagnosed with a specific chronic disease for which an absolute scale of maximum discomfort or abnormality is known or the VAS scale from a previous episode is known. In such cases, a simple normalization may be applied to the VAS score with respect to the maximum score or the score during the previous instance. For example, the VAS scale for amnesia may be adjusted up/down to provide a normalized VAS score for the severity of amnesia. Additionally, the VAS scale for a new episode of disabling back pain may be scored with respect to the previous disabling episode. In suitable cases, such as when patient is in a malignant state where no recovery is possible and only palliative treatment can be provided, then the patient's VAS score can be compared to the scores of the matching patient The graded escalation module 110 may repeat the acquisition of the VAS score and/or the VAS data after a specified period of time has elapsed since a VAS score and/or VAS data was last obtained from the patient. The specified period of time may be equal to or greater than two weeks. In some embodiments, the specified period of time may be less than two weeks. The graded escalation module 110 may notify the patient that they are supposed to indicate on the avatar and/or respond to the one or more questions after the specified period of time has elapsed. Each time a VAS score and/or VAS data is received, the VAS score and/or VAS data may be stored in the memory 117 and/or the graded escalation module 110 as a current VAS score and/or a current VAS data.

In some embodiments, the graded escalation module 110 may generate a first quality of health marker based on a comparison of the current VAS score and/or the current VAS data to a previous VAS score and/or a previous VAS data stored in the memory 117 and/or the graded escalation module 110. In some embodiments, the first quality of health marker may indicate a first dimension of the health of the patient as a pain dimension of the health of the patient. In these and other embodiments, the first quality of health marker may indicate whether additional examination of the health of the patient is to be performed by the physician.

In some embodiments, the graded escalation module 110 may determine whether the VAS score exceeds a VAS threshold value (such as around 8 in VAS pain scale). Additionally or alternatively it may determine the difference between the current VAS score and/or the current VAS data and the previous VAS score and/or the previous VAS data exceeds a threshold value. If a flag is raised because the VAS score does not exceed a threshold value or the difference between the current VAS score and/or the current VAS data and the previous VAS score and/or the previous VAS data does not exceed the threshold value, additional examination of the patient may not be performed by the graded escalation module 110 and the graded escalation module 110 may wait until the specified period of time has elapsed before repeating the acquisition of a subsequent VAS score and/or VAS data. Alternatively, if the VAS score exceeds a VAS threshold value or the difference between the current VAS score and/or the current VAS data and the previous VAS score and/or the previous VAS data exceeds the threshold value, additional examination of the patient may be performed by the graded escalation module 110.

In some embodiments, the graded escalation module 110 may determine whether the first quality of health marker indicates that the VAS score of somatic discomfort or pain is in the upper half of a range of VAS scores. If the first quality of health marker indicates that the VAS score is in the upper half of the range of VAS scores, the graded escalation module 110 may generate and provide a suitable alert to the physician or care-provider. The alert may include a quality of health result that indicates that the VAS score is in the upper half of the range of VAS scores and that the patient has an increased likelihood to experience an acute event in the near future and thus should have an additional in person examination performed by the physician and/or care-provider as soon as possible. In VAS scale of pain, a score of above 7.5 may show fairly severe pain and above 8.5 may be a cause for prompt attention. In the same way, in VAS health score, a score below 4 may show poor health that may require prompt attention.

In some embodiments, the graded escalation module 110 may direct the questionnaire module 104 to provide the general health questionnaire to the patient via the user device 124. In these and other embodiments, the first quality of health marker may be based on the patient general health input. If the patient general health input indicates that, in general, the health of the patient is excellent, very good, or good, additional examination of the patient may not be performed by the graded escalation module 110 and the graded escalation module 110 may wait until the specified period of time has elapsed before repeating the acquisition of patient general health input. Alternatively, if the patient general health input indicates that, in general, the health of the patient is fair or poor, additional examination of the patient may be performed by the graded escalation module 110. In some embodiments, if the health of the patient is being self-reported as fair or poor then to confirm the health status, the patient may be asked to provide the same information using an equivalent scale which is differently numbered such as a VAS scale where a score of 2 or less represents poor health and a score between 2 to 4 represents fair health. If the self-reported scores from both mechanisms do not match then the patient may be prompted again to provide the general status of his health till both the scores converge. In some embodiments, the first quality of health marker may include the first dimension as a general state of health dimension of the patient. In some embodiments, the first quality of health marker may be based on at least two of the patient general health input, the VAS score, and/or the VAS data. In some embodiments, if the health the first quality of health marker may additionally or alternatively be based on sensor data collected by the sensors 120 and 122. For example, the first quality of health marker may be based on sensor data collected by a PPG sensor, an ECG sensor, an EMG sensor, an accelerometer, a BP sensor, a blood glucose sensor, a respiration sensor, a posture sensor, a temperature sensor, an oxygen-saturation sensor, a cardiac output sensor, a sleep sensor, a stress sensor, an emotion sensing system, etc.

The graded escalation module 110 may compare the first quality of health marker to a first quality of health marker baseline value. If a difference between the first quality of health marker and the first quality of health marker baseline value exceeds a first quality of health marker threshold value, the graded escalation module 110 may generate and provide an alert to the physician or care-provider. The alert may include the quality of health result that indicates that the difference between the first quality of health marker and the first quality of health marker baseline value exceeds the first quality of health marker threshold value and that the patient is likely to experience an acute event in the near future and should have additional in person examination performed by the physician and/or care-provider as soon as possible.

The graded escalation module 110 may adjust one or more of a number of the questionnaires, a number of questions that are included in the questionnaires, and a type of questionnaires that are provided to the patient via the user device 124 based on the first quality of health marker. For example, if the difference between the current VAS score and/or the current VAS data and the previous VAS score and/or previous VAS data is between ten percent and twenty percent, the graded escalation module 110 may instruct the questionnaire module 104 to provide a single questionnaire with a reduced number of questions to the patient via the user device 124. As another example, if the difference between the current VAS score and/or the current VAS data and the previous VAS score and/or previous VAS data is between twenty percent and thirty percent, the graded escalation module 110 may instruct the questionnaire module 104 to provide a single questionnaire with an increased number of questions to the patient via the user device 124. As yet another example, if the patient general health input indicates a poor general state of health of the patient, the graded escalation module 110 may instruct the questionnaire module 104 to provide a single questionnaire with an increased number of questions to the patient via the user device 124.

Adjusting the number of questionnaires, the number of questions that are included in the questionnaires, and/or the type of questionnaires that are provided to the patient, may allow more relevant data to be collected by the graded escalation module 110, as warranted, while collecting less data patient data when not warranted. For example, if a patient is relatively healthy and is not experiencing much pain, questions related to high amounts of pain may not be relevant and may be omitted from the collection of data. Such adjustments may improve the functioning of the electronic device 102, the user device 124, and/or the network 118 compared to always administering all questionnaires and/or questions to a patient by administering only a subset of the questionnaires and/or questions as warranted. By administering only those questionnaires and/or questions that may be warranted, a reduction in communication bandwidth, processor bandwidth, and/or storage requirements may be achieved in one or more of the electronic device 102, the network 118, and/or the user device 124.

The questionnaires that the graded escalation module 110 instructs the questionnaire module 104 to provide to the patient via the user device 124 may provide an acute assessment of issues related to the quality of health of the patient. For example, the questionnaires may be related to mobility of the patient (e.g., the HALex questionnaire) or the quality of life of the patient (e.g., the HRQOL questionnaire). The graded escalation module 110 may generate a second quality of health marker of the patient based on the sensor provided HALex input (e.g., a present activity indicator) and/or the patient HRQOL input received in response to the corresponding questionnaire. The second quality of health marker may provide additional quantification of the quality of health of the patient in addition to the first quality of health marker.

In some embodiments, the graded escalation module 110 may instruct the questionnaire module 104 to provide the HALex questionnaire to the patient via the user device 124. Scores associated with responses to questions included in the patient HALex input may range between 0.1 to 1.0. The patient HALex input may indicate a perception of the patient of their general state of health (e.g., a perception score). Alternatively or additionally, the patient HALex input may indicate a functional status (e.g., a functional score) of the patient.

The graded escalation module 110 may determine an overall HALex score based on one or both of the perception score and the functional score. In some embodiments, if the perception score is high but the functional score is low, the overall HALex score may be low. In some embodiments, if the perception score is low but the functional score is high, the overall HALex score may be high.

In some embodiments, the graded escalation module 110 may scale the perception score based on chronic data obtained from the chronic disease database 126. For example, the graded escalation module 110 may access responses from other patients (e.g., NHIS data). The chronic data may include an averaged perception score of a variety of categories of patients. For example, the perception scores may be averaged according to various categories or combination thereof which influences the health of a patient even when all other things are equal such as age, gender, race, BMI, chronic disease, alcohol addiction, smoking addiction, daily activity level, availability of health insurance, education level, income level, place of residence, etc. For example, the graded escalation module 110 may multiply each perceived health score by a coefficient determined based on one or more such categories of which the patient is a member and which also have a markedly higher or lower risk than the mean value for the baseline categories.

The second quality of health marker may additionally or alternatively be based on sensor data collected by the sensors 120 and 122. For example, the first sensor 120 and/or the second sensor 122 may include a motion sensor (e.g., accelerometer) configured to determine how much the patient moves during a period of time. As another example, the first sensor 120 and/or the second sensor 122 may include a smart phone application configured to record daily events (e.g., number of baths, eating, getting dressed, or other events) of the patient and if another person assisted the patient. As yet another example, the first sensor 120 and/or the second sensor 122 may include a GPS sensor configured to determine whether another known GPS sensor was detected within a certain proximity of the patient during daily events of the patient.

The graded escalation module 110 may compare the second quality of health marker to a second quality of health marker baseline value. If a difference between the second quality of health marker and the second quality of health marker baseline value exceeds a second quality of health marker threshold value, the graded escalation module 110 may generate and provide the alert to the physician and/or care-provider. The alert may include the quality of health result that indicates that the difference between the second quality of health marker and the second quality of health marker baseline value exceeds the second quality of health marker threshold value and that the patient is likely to experience an acute event in the near future and should have additional in person examination performed by the physician and/or care-provider as soon as possible.

Alternatively, if the difference between the second quality of health marker and the second quality of health marker baseline value does not exceed the second quality of health marker threshold value, the graded escalation module 110 may instruct the questionnaire module 104 to provide the HRQOL questionnaire to the patient via the user device 124. The patient HRQOL input received in response to the HRQOL questionnaire may indicate a total number of physical unhealthy days and/or mental unhealthy days of the patient. Likewise, the patient HRQOL input may include a non-ordinal unhealthy days score (e.g., cardinal health score). In some embodiments, the non-ordinal unhealthy days score may be determined using factor analysis theory in statistics where based upon a variability among the observed variables, a smaller number of unobserved (e.g., latent) variables may be used to explain the observed variables. Additionally, the observed variables may include linear combinations of the unobserved variables and an error terms. The factor analysis theory may be performed using well known methods in the field.

In some embodiments, the graded escalation module 110 may generate the quality of health result based on at least one of the difference between the first quality of health marker and the first quality of health marker baseline value and the second quality of health marker and the second quality of health marker baseline value. The graded escalation module 110 may generate and provide the alert that includes the quality of health result to the physician and/or care-provider. The quality of health result may indicate that the patient is not likely to experience an acute event in the near future and can have additional in person examination performed by the physician and/or care-provider at a later date.

The patient HRQOL input may indicate a current level, mood, and correlated data such as health risks and conditions; functional status; social support; and/or socioeconomic status of the patient. The patient HRQOL input may provide a way to determine an impact of the health of the patient on the quality of life of the patient outside of what can be determined by detailed medical analysis (e.g., use of a microscope). The patient HRQOL input may be used to determine a burden of preventable disease, injuries, and disabilities of the patient. Additionally, the number of physical healthy days and/or mental healthy days may be used to determine outcomes of the health of the patient and a predictor of changes in the health of the patient.

Alternatively or additionally, the patient HRQOL input may contain relational model that provide insight into relationships between data included in the patient HRQOL input and one or more risk factors. Furthermore, the patient HRQOL input may provide additional ways for physicians to monitor progress of the patient so as to achieve most Medicare health objectives whether stated or unstated. Also, the patient HRQOL input may be used as valid indicators of unmet health needs of the patient and to predict intervention outcomes. The patient HRQOL input may indicate practices that affect the physical and/or mental health of the patient and/or the patients that are included in the chronic data.

In some embodiments, the patient HRQOL input may provide new insights into the relationship between HRQOL and clinically-measured health characteristics and conditions such as BP; physical strength and endurance; oral health; and mental health etc. For example, if a patient with pre-chronic conditions is being considered then a certain quantum of change to the pre-chronic conditions may occur before the chronic condition sets in. For example, in older adults the HALEX score in a scale of zero to one hundred may change by fourteen points when the patient has developed heart failure. Similarly, a deterioration of HALEX score or any other health score by three percent may indicate worsening pre-chronic conditions such as thyroid but may not be indicative of a chronic condition like heart failure.

The HRQOL data of a patient may be interpreted in terms of what is expected and what is observed. The graded escalation module 110 may adjust the patient HRQOL input based on one or more factors that may affect perceived physical and/or mental unhealthy days by the patient. Additionally or alternatively, the graded escalation module 110 may adjust the patient HRQOL input based on the chronic data included in the chronic disease database 126. In some embodiments, the patient HRQOL input may be adjusted based on demographic, socioeconomic, phenotype, genotype, and/or health pattern factors of the patient. For example, the patient HRQOL input may be adjusted if the patient lives in a region that experiences a higher number of days of cloudy weather. As another example, the patient HRQOL input may be adjusted by using a weighted HRQOL score based on an overall HRQOL status of patients included in the chronic data. The HRQOL data of a patient may be interpreted in terms of what is expected and what is observed. Needless to say, the modules can be configured so that the HRQOL data of a patient reflects the difference between two perceived health markers; one may represent the expectation of the physician for the patient, and second that is actually being observed by patient as the status of his health.

The graded escalation module 110 may compare the patient HRQOL input to the objective markers included in the chronic database. For example, the chronic data may include the national health and nutrition examination survey (NHANES) data. The NHANES data may include objective measures of physical health and blood tests for a group of patients. The NHANES data may include the number of reported unhealthy days and activity limitation days of the group of patients in relation to risk factors such as measured BMI and/or physical endurance, as well as to reported nutritional and physical activity patterns of the group of patients.

In some embodiments, the HRQOL questionnaire may be provided as part of an overall behavioral risk factor surveillance system (BRFSS) health determination. The BRFSS health determination may be based on at least two of the VAS score, the VAS data, and the patient HRQOL input. The BRFSS health determination may provide an ordinal number to provide a trend analysis for the physician. In some embodiments, the BRFSS health determination may be further based on the sensor data obtained from the sensors 120 and 122. In some embodiments, as the system starts incorporating a larger sample of the patient wired with sensors, one can use the metadata derived from the sensor data as the baseline. The metadata may include the mood, activity, lifestyle trend, sleep, stress, or any such psychophysiological components of health that can be deduced from the sensor data.

The graded escalation module 110 may compare the total number of physical unhealthy days to a physical unhealthy days threshold value. Likewise, the graded escalation module 110 may compare the total number of mental unhealthy days to a mental unhealthy days threshold value. If either of the total number of physical unhealthy days or the total number of mental unhealthy days exceeds the corresponding threshold value, the graded escalation module 110 may generate and provide the alert to the physician and/or care-provider. The alert may indicate that either the total number of physical unhealthy days or the total number of mental unhealthy days exceeds the corresponding threshold value in terms of the actual or in terms of the deviation seen from the statistical viewpoint, and the probability computed from the data of similar patients that the patient is likely to experience an acute event in the near future and should have additional in person examination performed by the physician and/or care-provider as soon as possible. The quality of health result may also include the difference between the total number of physical unhealthy days and the physical unhealthy days threshold value.

Additionally or alternatively, if the total number of mental unhealthy days exceeds the mental unhealthy days threshold value, the graded escalation module 110 may direct the questionnaire module 104 to provide the PHQ2 questionnaire to the patient via the user device 124. The patient PHQ2 input received in response to the PHQ2 questionnaire may indicate a state of depression of the patient. In some embodiments, the PHQ2 questionnaire may be provided to the patient via the user device 124 before scheduling an in-person examination or at any other suitable time. In some embodiments, the module can escalate the depression detection by having the PHQ2 questionnaire be followed by the PHQ9 questionnaire if the PHQ2 questionnaire reflects that the patient may likely be depressed. Additionally, any other similar questionnaire that assesses depression can be employed as well.

The graded escalation module 110 may compare the patient PHQ2 input to a PHQ2 baseline value. If a difference between the patient PHQ2 input and the PHQ2 baseline value exceeds a PHQ2 threshold value (e.g., indicates that the patient is experiencing severe depression), the graded escalation module 110 may generate and provide the alert to the physician or care-provider. The alert may include the quality of health result that indicates that the difference between the patient PHQ2 input and the PHQ2 baseline value exceeds the PHQ2 threshold value and that the patient is likely to experience an acute event in the near future and should have additional in person examination performed by the physician and/or care-provider as soon as possible. In some embodiments, the PHQ2 value can be replaced by PHQ9 value when the depression detection is escalated by having the PHQ2 questionnaire be followed by the PHQ9 questionnaire. Additionally, as mentioned earlier, any other similar questionnaire that assesses depression can be employed as well.

If the difference between the patient PHQ2 input and the PHQ2 baseline value does not exceed the PHQ2 threshold value, the graded escalation module 110 may repeat the acquisition of patient PHQ2 input after a specified period of time has elapsed since patient PHQ2 input was last obtained from the patient. The specified period of time may be equal to or greater than two weeks. In some embodiments, the specified period of time may be less than two weeks. Additionally, the triggers can be generated using or in terms of PHQ9 or any similar depression questionnaire.

In some embodiments, if the total number of physical unhealthy days does not equal zero but does not exceed the physical unhealthy days threshold value but the recent VAS score and/or the recent VAS data indicates that the patient is experiencing significant amounts of pain, the graded escalation module 110 may yet generate and provide the alert to the physician or care-provider. The alert may include the quality of health result that indicates that the total number of physical unhealthy days does not equal zero but does not exceed the physical unhealthy days threshold value and that the patient is experiencing significant amounts of pain and given the high pain level interpreted in terms of data of similar patients, the patient is likely to experience an acute event in the near future and should have additional in person examination performed by the physician and/or care-provider as soon as possible.

If the total number of physical unhealthy days and the total number of mental unhealthy days does not exceed the corresponding threshold value. The graded escalation module 110 may repeat the acquisition of the patient HRQOL input after the specified period of time has elapsed since patient HRQOL input was last obtained from the patient. The specified period of time may be equal to or greater than two weeks. In some embodiments, the specified period of time may be also less than two weeks.

In some embodiments, the graded escalation module 110 may be configured to periodically monitor the health of the patient by collecting and monitoring multiple iterations of the quality of health result. If the first quality of health marker and the second quality of health marker included in the quality of health result indicate that the patient is not likely to experience an acute event in the near future, the quality of health result may be stored in the memory 117 and/or the graded escalation module 110 as a first quality of health result. After the specified period of time, the graded escalation module 110 may repeat the steps described above and may generate a second quality of health result, which may include a current first quality of health marker and a current second quality of health marker. The specified period of time may be equal to or greater than two weeks. In some embodiments, the specified period of time may be less than two weeks.

If either the current first quality of health marker or the current second quality of health marker indicates that that the patient is likely to experience an acute event in the near future, the alert may be generated and provided to the physician and/or care-provider. The alert may include the current first quality of health marker and/or the current second quality of health marker. Additionally, the alert may indicate that the patient should have additional in person examination performed by the physician and/or care-provider as soon as possible. Alternatively, if the current first quality of health marker and the current second quality of health marker indicate that the patient is not likely to experience an acute event in the near future, the second quality of health result may be stored in the memory 117 and/or the graded escalation module 110.

Additionally, the graded escalation module 110 may be configured to compare the first quality of health result and the second quality of health result to determine a trend of the health of the patient. For example, the graded escalation module 110 may compare the first quality of health marker included in the first quality of health result to the first quality of health marker include in the second quality of health result. Likewise, the graded escalation module 110 may compare the second quality of health marker included in the first quality of health result to the second quality of health marker included in the second quality of health result.

The trend of the health of the patient may indicate whether the first quality of health markers and/or the second quality of health markers in the first quality of health result and the second quality of health result are the same/similar or are different. If the first quality of health markers and/or the second quality of health markers in the first quality of health result and the second quality of health result are the same/similar, the alert may indicate that the patient is not likely to experience an acute event in the near future. If the first quality of health markers and/or the second quality of health markers in the first quality of health result and the second quality of health result are different, the graded escalation module 110 may determine whether the difference is due to an improvement in the health of the patient (e.g., the scores associated with the first quality of health marker and/or second quality of health marker in the second quality of health result increased). If the difference is due to an improvement in the health of the patient, the alert may indicate that the patient is not likely to experience an acute event in the near future.

If the difference is not due to an improvement in the health of the patient (e.g., the scores associated with the first quality of health marker and/or the second quality of health marker in the second quality of health result decreased), the graded escalation module 110 may determine whether the difference exceeds an iteration threshold value. If the difference does not exceed the iteration threshold value, the alert may indicate that the patient is not likely to experience an acute event in the near future. For example, a difference of 0.5 or more in the patient HALex input included in the second quality of health result compared to the patient HALex input included in the first quality of health result may indicate that the trend of the health of the patient is worsening. In some embodiments, a difference of 0.03 in patient HALex input may indicate that the trend of the health of the patient is worsening. If the difference exceeds the iteration threshold value, the alert may indicate that the patient is likely to experience an acute event in the near future and should have additional in person examination performed by the physician and/or care-provider as soon as possible.

In some embodiments, the graded escalation module 110 may determine a short-term health compliance (SHC) score. The SHC score may be normalized to a score between zero and one hundred. The SHC score may be based on the patient HRQOL input being worth one hundred points (or other value); the patient HALex input being worth one hundred points (or other value); or the patient HRQOL input being worth fifty points (or other value) and the patient HALex input being worth fifty points (or other value) for a total of one hundred points (or other value).

In some embodiments, the graded escalation module 110 may determine an activity of daily living (ADL) value of the patient based on the patient HALex input. The ADL value may be compared to an ADL baseline of the patient that was previously determined. The ADL baseline may be determined based on the EHR data included in the EHR database 128 and/or previous patient HALex input received by the graded escalation module 110. The first quality of health marker may be further based on the comparison of the ADL value to the ADL baseline.

Additionally or alternatively, portions of the patient HALex input, patient HRQOL input, patient PHQ2 input, or any other patient related data may be collected via the sensors 120 and 122. For example, the first sensor 120 and/or the second sensor 122 may include an accelerometer configured to determine movement of the patient, which may be compared against prior movement of the patient to determine whether the patient's movement has increased, decreased, or remained constant, which may be used to determine the ADL value of the patient. As another example, each distinct, regular, activity can be recognized by studying the time series being generated from the accelerometer and/or any other wearable inertial sensors since different activities generate different pattern of movement in the three-dimensional space. Thus, in context of time and of activity energy, when sensor output is mapped and analyzed in each of the three dimensions (for example, x, y, z), the pattern that is repeated in time may be distinct and hence unique. The type of activity can be determined by looking at the signature of the time series data either completely or partially, when each of the three dimensions are concerned.

As another example, the first sensor 120 and/or the second sensor 122 may include a HR monitor configured to determine an HR of the patient, which may be used to determine if the patient is experiencing irregular heartbeats. As yet another example, the first sensor 120 and/or the second sensor 122 may include a GPS device configured to determine how much the patient is home bound, is exposed to polluted areas, where the patient eats, and/or is exposed to extreme temperatures either high or low.

In some embodiments, the mood of the patient may be determined by performing sensor analysis of the sensor data. The sensor data may include an analysis of facial expressions, balance of sympathetic and parasympathetic nervous system, heart rate, heart rate variability, respiration, Galvanic Skin Response (electro dermal analysis) of the patient based on at least one of a social interaction of the patient with a phone or a variation in activities of the patient with respect to a healthy patient emotional profile. Additionally, a heart rate of a patient and/or a heart rate variability of the patient may be analyzed in concert with the facial expressions using a camera (for facial action coding-based analysis), the posture of the patient, and/or similar biomarkers.

In some embodiment, the patient response may be auto-filled via the sensor input as described above and then validated by the patient. In some embodiment, the sensor derived input(s) can over-ride the patient provided input(s). In some embodiment, the patient response may be taken as the weighted average of sensor derived input and the patient derived input. In some other embodiment, the patient credibility may be given a weightage by the care-provider which may be used to create the composite patient response by combining patient provided input and input derived via sensor. In some embodiment, the physician may be provided patient sensor value that can be compared to patient's response to determine the veracity of the patient's response, and hence create the patient credibility. In some embodiment, the physician may be provided a range of credibility weightage to provide to the patient-derived input so that a range of scores may be computed for the patient and based on the physician's clinical assessment, the physician can empirically determine the credibility weightage.

In some embodiment, for each response the patient provides, the patient may be asked a set of questions specific to that response to validate the patient provided inputs and guide the patient to make the correct assessment. For example, if a patient is asked if he needs help to do the daily tasks of living. If the patient's response is YES but the response is due to a mistaken understanding of what it means to get help getting dressed then the additional questions may serve to clarify his input.

In some embodiment, the sensor derived input may be calibrated by a statistical analysis of the expected value from a matching set of users. In some embodiment, the sensor derived input may be calibrated by a statistical analysis of the expected value from a matching set of users as determined by the physician with or without an analysis of the statistical information.

The chronic burden module 108 may include software executable by or on the electronic device 102. For example, the chronic burden module 108 may include code stored on the electronic device 102 that may be executed line-by-line by the processor of the electronic device 102 and/or may be loaded into the memory 117 and executed by the processor of the electronic device 102 to perform or control performance of one or more operations described herein in connection with the chronic burden module 108. Alternatively or additionally, the chronic burden module 108 may be implemented in hardware, e.g., as an ASIC, an FPGA, or other hardware device configured to perform or control performance of one or more operations described herein in connection with the chronic burden module 108.

The chronic burden module 108 may be configured to evaluate and stratify a chronic care burden of a patient based on one or more factors that may include responses by the patient to questionnaires provided by the questionnaire module 104, sensor data collected by the sensors 120 and 122, and/or the EHR data included in the EHR database 128. In some embodiments, the chronic care burden of the patient may also be based on the chronic data included in the chronic disease database 126 and/or responses to questionnaires provided by the disease calculator 106 (e.g., a chronic disease calculator score). Additional or alternatively, the chronic burden module 108 may determine whether the patient in likely to experience a rise in the chronic care burden associated with one or more chronic diseases (e.g., admission to an intensive care unit (ICU) and/or hospitalization) in the intermediate future (e.g., in six to twelve months).

The chronic burden module 108 may be configured to determine the chronic care burden of the patient in one or more areas of assessment. This module scores on an ordinal system (say, no risk to very high risk) the factors that are well known to lead to the most common chronic diseases and also the factors that may act as an impediment in obtaining prompt and appropriate healthcare. For example, the one or more areas of assessment may include clinical symptom factors, service access factors, risk factors, extenuating factors, psycho-social factors, and/or change readiness factors. Clinical symptom factors may include COPD, CHF, dementia, depression, or any other appropriate clinical symptom factor. Service access factors may include hospital admissions, self-care, general practitioner follow up, or any other appropriate service access factor. Risk factors may include smoking, obesity, BP, HBA1C, drug use, alcohol abuse, recent hospitalization or any other appropriate risk factor. Extenuating factors may include pain, stress, wounds, or any other appropriate extenuating factor. Psycho-social factors may include financial, transport, disability, or any other appropriate psycho-social factor. Change readiness factors may include action relapse or any other appropriate change readiness factor.

The chronic burden module 108 may receive the EHR data related to the patient included in the EHR database 128. The chronic burden module 108 may determine a biological profile, a psychological profile, and/or a social profile of the patient based on the EHR data. The biological profile, psychological profile, and/or social profile of the patient may include physician notes regarding the different profiles of the patient.

The EHR data may include factors at a population level, a practice level, and/or a patient level to provide varying levels of CCB score granularity. Additionally, the EHR data may include data related to weight, height, BMI of the patient and BP of the patient. The EHR data may also include extenuating factors of the patient such as pain of the patient. The EHR data may additionally include psycho-social factors of the patient such as financial status of the patient. The chronic burden module 108 may include a list of chronic conditions that the patient is experiencing based on the EHR data.

In some embodiments, the chronic burden module 108 may provide the avatar to the patient via the user device 124. The chronic burden module 108 may determine the amount of pain the patient is experiencing, where on the body that patient is experiencing pain, and/or whether the nature of pain is neuropathic, musculoskeletal or visceral organ based on patient input provided on the avatar and by using the VAS score included in the patient input. In some embodiments, the VAS score may be between zero and ten, which may provide higher resolution of the CCB score.

In some embodiments, the chronic burden module 108 may direct the questionnaire module 104 to present one or more questionnaires related to the quality of health of the patient to the patient via the user device 124. The chronic burden module 108 may adjust the number of the questionnaires and/or the number of questions that are included in the questionnaires that are provided to the patient based on previous CCB scores or any additional information collected via interactions with the caregiving staff. The number of the questionnaires and/or the number of questions that are provided to the patient may be determined so as to reduce the number of clicks (e.g., responses to questions) by creating minimum number of categories (e.g., categories of health-related factors that influence CCB score) to determine the CCB score of the patient. The questions that are included in the questionnaire may be sorted into categories such as "Your Biological Risk Factors", "Your Readiness to Change Health Habits", "Your Capacity of Self-Care", and/or "Your Social Life." Each category may only include questions that pertain to the category. One questions may ask the patient to only identify which categories the patient has experienced changes. In some embodiments, the minimum number of clicks may be two clicks since the patient may only identify a single category in which the patient has experienced a change and then click a question corresponding to the category where the change has been experienced Alternatively or additionally, adjusting the number of questionnaires and/or questions that are provided to the patient as warranted, and as directed by the chronic burden module 108, may improve the functioning of the electronic device 102, the network 118, and/or the user device 124 as described above.

In some embodiments, the questions may include: "How do you feel?" "How are your health problems affecting you?" "How are your health problems affecting your ability/disability?" "How are your health problems affecting your functional capacity, independence, or other aspects of your health and well-being?" In these and other embodiments, the questionnaires may include the HALex, HRQOL, PHQ2, and/or any other appropriate questionnaire for determining the quality of health of the patient. Additionally or alternatively, the questions may include "What is your current weight, BP, glucose level, and/or waist to hip ratio (WHR)?"

The chronic burden module 108 may receive the sensor data from the sensors 120 and 122 related to the quality of health of the patient. The sensor data may include information regarding the state of depression, hypertensions, stroke risk, COPD, diabetes, fall risk, and/or any other appropriate sensor data related to the quality of health of the patient. For example, the sensor data may also include GPS data for determining service access such as ER visits, general physician (GP) follow-ups. Additionally, the sensor data may include data related to risk factors such as smoking and inactivity of the patient. COPD risk factors such as BP and psycho-social factors (e.g., depression) may be determined using bio-sensors.

The chronic burden module 108 may determine the CCB score of the patient and a pre-defined risk stratification based on at least two of the EHR data related to the patient, the sensor data, the patient input provided on the avatar, and/or the patient input received in response to the questionnaires. The CCB score may be broken down into one or more categories. For example, the CCB score may include one or more categories of a risk factor category, a social life category, and an approach toward health maintenance of the patient category. The CCB score may be normalized to a score between zero and one hundred or other range or values.

The pre-defined risk stratification may include a baseline score of one or more risk categories based on multiple factors. For example, the pre-defined risk stratification may be based on the chronic data included in the chronic disease database 126 related to patients that have similar health issues as the patient, patients that have similar demographic characteristics, patients that have similar bio-profiles, and/or any other appropriate patient characteristics that may be used to determine a baseline.

The chronic burden module 108 may determine a risk stratification of the patient based on the pre-defined risk stratification. The risk stratification may indicate a present health risk assessment of the patient (e.g., whether the patient is likely to experience a rise in the chronic care burden associated with one or more chronic diseases in the intermediate future). The risk stratification may include one or more of the following risk categories: urgent; very high; high; moderately high; moderate; and/or low.

The chronic burden module 108 may generate and provide a CCB result to the physician and/or care-provider. The CCB result may include the CCB score and the risk stratification of the patient. If the risk stratification of the patient is urgent, very high, high, or moderately high, the CCB result may also indicate that the patient should have additional in person examination performed by the physician and/or care-provider as soon as possible. Alternatively, if the risk stratification of the patient is moderate or low, the CCB result may be stored in the memory 117 and/or the chronic burden module 108 as a first CCB result. After the specified period of time, the chronic burden module 108 may repeat the steps described above and may generate a second CCB result. The specified period of time may be equal to or greater than two weeks. In some embodiments, the specified period of time may be less than two weeks.

The chronic burden module 108 may compare the first CCB result to the second CCB result to determine a trend of the health of the patient. If the trend of the health of the patient is improving, the second CCB result may be provided to the physician and/or care-provider and may be stored in the memory 117 and/or the chronic burden module 108. If the trend of the health of the patient is declining, an alert including the second CCB result may be generated and provided to the physician and/or care provider. The alert may indicate that the trend of the health of the patient is declining and that the patient should have additional in person examination performed by the physician and/or care-provider as soon as possible.

In some embodiments, the chronic burden module 108 may direct the questionnaire module to provide a general self-reported health (GSRH) question to the patient via the user device 124. A GSRH score may be determined based on patient GSRH input received in response to the GSRH question along a scale of zero to ten and/or the VAS score. Alternatively, the GSRH score may include a health status of the patient of excellent, very good, good, fair, or poor. The GSRH score may also be labeled as excellent, very good, average, poor, very poor.

The chronic burden module 108 may combine the CCB score and the GSRH score. The risk stratification may be determined based on the combined score of the CCB score and the GSRH score. In some embodiments, if the patient provides a low GSRH score and includes a high CCB score, the patient may be more likely to be at both a high acute risk as well as a high chronic care burden risk.

In some embodiments, the chronic burden module 108 may direct the questionnaire module 104 to provide the HRQOL questionnaire to the patient via the user device 124. The patient HRQOL input received in response to the HRQOL questionnaire may include the total number of physical unhealthy days and/or mental unhealthy days of the patient. Additionally or alternatively, the chronic burden module 108 may direct the questionnaire module to provide the HALex questionnaire to the patient via the user device 124. The patient HALex input received in response to the HALex questionnaire may indicate whether the patient has recently experienced a limitation in activity. Additionally or alternatively, the patient HALex input may include an activity limitation score indicating the limitation in activity. The activity limitation score may be based on a particular level of disability as indicated by the patient. Multiple questions may be provided to the patient to determine whether the patient is experiencing limitations in performing various tasks. For example, whether the patient is experiencing limitations performing the basic tasks for daily survival; tasks for daily chores; tasks to join work force due to physical, mental, or emotional problems; tasks in the work the patient is doing due to physical, mental, or emotional problems; or tasks in any aspect of life due to physical, mental, or emotional problems. Each question may include an ADL weight value. For example, the patient is experiencing limitations performing the basic tasks for daily survival may be assigned an ADL weight of 0; tasks for daily chores may be assigned an ADL weight of 0.2; tasks to join work force due to physical, mental, or emotional problems may be assigned an ADL weight of 0.4; tasks in the work the patient is doing due to physical, mental, or emotional problems may be assigned an ADL weight of 0.65; or tasks in any aspect of life due to physical, mental, or emotional problems may be assigned an ADL weight of 0.8. The ADL weight may be combined with PH coefficients determined based on GSRH questionnaires. For example, a GSRH score of excellent (top rank) may be assigned a PH coefficient of 1.0, very good (second rank) may be assigned a PH coefficient of 0.85, good (third rank) may be assigned a PH coefficient of 0.7, (second to the poor) may be assigned a PH coefficient of 0.3, and poor (worst rank) may be assigned a PH coefficient of 0. The activity limitation score in this example may be determined according to equation 1:

$$\text{Activity Score} = 0.1 + 0.9(0.41*PH + 0.41*ADL\ Weight + 0.18*PH*ADL\ Weight) \quad [\text{Equation 1}]$$

In Equation 1, PH may be the PH coefficient from the GSRH score and ADL weight may be the ADL weight in response to the multiple questions provided to the patient to determine whether the patient is experiencing limitations in performing various tasks.

The chronic burden module 108 may combine the CCB score with the patient HRQOL input and/or the patient HALex input. The risk stratification of the patient may be determined based on the combination of the CCB score with the patient HRQOL input and/or the patient HALex input.

In some embodiments, the chronic burden module 108 may direct the disease calculator 106 to provide one or more questionnaires to the patient via the user device 124. The chronic burden module 108 may determine the disease calculator score based on the responses to the questionnaires provided by the disease calculator 106. The chronic burden module 108 may combine the CCB score with the disease calculator score. The risk stratification of the patient may be determined based on the combination of the CCB score with the disease calculator score. In some embodiments, the risk stratification of the patient determined based on the combination of the CCB score with the disease calculator score may indicate impending chronic care diseases with a risk of sudden death (e.g., a sudden death burden).

The compliance to a recommended lifestyle health choice of a patient may be analyzed in the lifestyle choice module 114, which may include software executable by or on the electronic device 102. For example, the lifestyle choice module 114 may include code stored on the electronic device 102 that may be executed line-by-line by the processor of the electronic device 102 and/or may be loaded into the memory 117 and executed by the processor of the electronic device 102 to perform or control performance of one or more operations described herein in connection with the lifestyle choice module 114. Alternatively or additionally, the lifestyle choice module 114 may be implemented in hardware, e.g., as an ASIC, an FPGA, or other hardware device configured to perform or control performance of one or more operations described herein in connection with the lifestyle choice module 114.

The lifestyle choice module 114 may be configured to evaluate and stratify compliance to a recommended lifestyle health choice of a patient based on one or more factors that may include responses by the patient to questionnaires provided by the questionnaire module 104, sensor data collected by the sensors 120 and 122, and/or the EHR data included in the EHR database 128. In some embodiments, the lifestyle health compliance of the patient may also be based on the chronic data included in the chronic disease database 126 and/or responses to questionnaires provided by the disease calculator 106.

The lifestyle choice module 114 may be configured to determine whether the patient has experienced a change in lifestyle choice, for good or bad, in one or more categories over a period of time. In some embodiments, the period of time may include the period of time since the patient last had an in-person examination performed by the physician and/or care provider. The one or more categories may include dietary health choice; daily routine; dietary harm avoidance; organized physical activities; and/or social and mental balance. The lifestyle choice module 114 may determine a healthy lifestyle choice compliance (LCC) score based on changes in the lifestyle of the patient, which may indicate internal control of health of the patient. A LCC score of one hundred indicates full compliance to lifestyle choice prescriptions and a LCC score of zero indicates complete lack of compliance to the lifestyle choice prescriptions.

The lifestyle choice module 114 may have provision to provide or determine the classifiability, proportionality, and/or adaptability of the LCC score. Classifiabiltiy of the LCC score may be based on the chronic diseases of the patient. For example, if the patient has diabetes, the LCC score may be classified based on questions, data (possibly including from sensors), and/or patient input related to diabetes. Proportionality of the LCC score may be achieved by assigning categories that are more important for the particular case of the patient. For example, the patient may be compliant with dietary healthy choices, but may not be compliant with dietary harm avoidances and as such that category may be given greater weight using a VAS scale-based slider. Adaptability of the LCC score may be achieved by varying the LCC score in ordinal manner. For example, if a patient receives a score of four for exercising six days one week, the patient will receive a score of two for exercising three days a subsequent week.

The lifestyle choice module 114 may receive the EHR data related to the patient included in the EHR database 128. The lifestyle choice module 114 may determine a biological profile, a psychological profile, and/or a social profile of the patient based on the EHR data included in the EHR database 128. Additionally, or alternatively, the lifestyle choice module 114 may determine a previous lifestyle choice prescription of the patient based on the EHR data.

The lifestyle choice module 114 may direct the questionnaire module 104 to provide one or more questionnaires to the patient via the user device 124. For example, the lifestyle choice module 114 may direct the questionnaire module 104 to provide the HLPCQ questionnaire to the patient. Additionally, or alternatively, the lifestyle choice module 114 may direct the questionnaire module 104 to provide the question "How do you rate the efforts you make to take care of your health?"

The lifestyle choice module 114 may adjust the number of the questionnaires and/or the number of questions that are included in the questionnaires that are provided to the patient based on previous lifestyle choice prescriptions, as warranted. Adjusting the number of questionnaires and/or questions that are provided to the patient as warranted, and as directed by the lifestyle choice module 114, may improve the functioning of the electronic device 102, the network 118, and/or the user device 124 as described above.

Additionally, or alternatively, the lifestyle choice module 114 may ask the patient if the patient has experienced any changes in the one or more categories (e.g., dietary health choice; daily routine; dietary harm avoidance; organized physical activities; and/or social and mental balance). The number of the questionnaires and/or the number of questions that are included in the questionnaires that are provided to the patient may be determined so as to reduce a number of clicks (e.g., responses to questions) and a minimum number of categories (e.g., categories of health-related factors) to determine a lifestyle choice prescription or update the lifestyle choice prescription of the patient. In some embodiments, the minimum number of clicks may include fifteen or less clicks. Alternatively, the minimum number of clicks may include more than fifteen clicks.

The lifestyle choice module 114 may receive patient HLPCQ input in response to the HLPCQ questionnaire. The patient HLPCQ input may include responses to each of the questions indicating whether adherence to the question is strong, moderate, low, or absent. If the adherence is low or absent, the specified period of time between determinations of the lifestyle choice prescription may be reduced. For example, the specified period of time between determinations of the lifestyle choice prescription may be reduced to once every six weeks. The patient HLPCQ input may include response to the question of how do you rate the efforts you make to take care of your health as either Excellent, very good, good, fair, or poor.

Additionally or alternatively, the lifestyle choice module 114 may direct the questionnaire module 104 to provide a questionnaire to assess the lifestyle risk score (LRSQ) via the user device. The LRSQ response may indicate habits of the patient that may be harmful. For example, smoking, alcohol, dietary harm, sedentary lifestyle, schedule irregularity, quality of social, and/or stress management of the patient.

The lifestyle choice module 114 may receive the sensor data from the sensors 120 and 122 related to the quality of health of the patient. The sensor data may include information regarding lifestyle activities related to one or more chronic diseases of the patient. The sensor data may quantify compliance of the patient with the lifestyle choice prescriptions within a range of values between zero and one.

The lifestyle choice module 114 may determine the LCC score based on the sensor data, the patient LRSQ input, and/or the patient HLPCQ input. For example, each response included in the patient HLPCQ input may be assigned a weight of four (e.g., four points for strong, three points for moderate, two points for low, and one point for absent adherence). The total number of responses may be twenty five and the LCC score may be determined out of one hundred points. Alternatively, each response included in the patient HLPCQ input may be individually weighted based on the chronic diseases or the individual assessment of the patient. For example, adherence to medication lifestyle prescription may be weighted higher than other lifestyle prescriptions. Virtually in the advanced stages of most chronic diseases, there may be disease specific lifestyle constraints. Thus, a system that is directed towards elderly may account for personalization. The total score may be out of 100 but their weightage may be broken down over a smaller or larger number of questions. For example, if there are only twenty questions in the lifestyle questionnaire that are deemed relevant then the weight of each question may be five.

In some embodiments, the LCC score may include multiple categories, such as permanent and controllable. The permanent category may include permanent factors such as the age, the race, the gender, the existence of certain chronic diseases, the health history of the patient. The controllable category may include factors related to a patient's approach towards health care such as diet, exercise, disciplined daily routine, dietary harm avoidance, etc.

In some embodiments, the lifestyle choice module 114 may determine one or more lifestyle choice prescription compliance targets for the patient. Each of the lifestyle choice prescriptions targets may be assigned a separate weighted score from zero to one. The weighted scores may be assigned based on importance of the chronic disease and/or the lifestyle choice prescription.

The lifestyle choice module 114 may generate a lifestyle choice result that includes the LCC score of the patient. The lifestyle choice module 114 may provide the lifestyle choice result to the physician and/or care provider. The lifestyle choice module 114 may repeat the steps discussed above after the specified period of time has elapsed since a lifestyle choice prescription was last obtained from the patient. In some embodiments, the specified period of time may be between two and three months. Alternatively, the specified period of time may be greater than three months or less than two months. The length of the specified period may be based on the urgency of the lifestyle intervention and thus can be as less as even one week.

In some embodiments, the patient input (e.g., patient responses to the questionnaires) may be scaled within a range of zero to one and the LCC score may be based on the scaled patient input. In these and other embodiments, a score of one equals excellent adherence and a score of zero equals absent adherence to the corresponding lifestyle choice prescription. Others ranges or values may be used in other embodiments.

In some embodiments, the lifestyle choice module 114 may receive the chronic data from the chronic disease database 126. The chronic data may include LCC scores for patients that are similar to the patient (e.g., similar patients). For example, the patients may be a similar age, weight, gender, race, or any other appropriate characteristic for determining patients are similar. As another example, the patients may be experiencing the same chronic diseases. The lifestyle choice module 114 may compare the LCC score of the patient to the LCC scores included in the chronic data. The lifestyle choice result may also include a statistical rank of the patient compared to the patients included in the chronic data.

In some embodiments, if the LCC score of the patient falls below a pre-specified limit, the lifestyle choice module 114 may generate and provide an alert to the physician and/or care provider. The alert may include the LCC score and may indicate that the LCC score of the patient fell below the pre-specified limit and that the patient should have additional in person examination performed by the physician and/or care-provider as soon as possible. The pre-specified limit may be determined based on the patient input and/or the sensor data. In some embodiments, the pre-specified limit may be determine based on physician preferences. For example, the pre-specified limit may be set to one hundred fifty minutes of exercise a week, eight hours of sleep a night, or sleeping before midnight. Additionally or alternatively, the pre-specified limit may be based on a number of standard deviations of change that is observed below the pre-specified limit.

The total health module 116 may include software executable by or on the electronic device 102. For example, the total health module 116 may include code stored on the electronic device 102 that may be executed line-by-line by the processor of the electronic device 102 and/or may be loaded into the memory 117 and executed by the processor of the electronic device 102 to perform or control performance of one or more operations described herein in connection with the total health module 116. Alternatively or additionally, the total health module 116 may be implemented in hardware, e.g., as an ASIC, an FPGA, or other hardware device configured to perform or control performance of one or more operations described herein in connection with the total health module 116.

The total health module 116 may be configured to generate a health risk score of the patient. The health risk score may be based on responses by the patient to questionnaires provided by the questionnaire module 104, sensor data collected by the sensors 120 and 122, the SHC score determined by the graded escalation module 110, the CCB score determined by the chronic burden module 108, the LCC score determined by the lifestyle choice module 114, and/or the EHR data included in the EHR database 128. In some embodiments, the health risk score may also be based on the chronic data included in the chronic disease database 126.

The total health module 116 may determine the health risk score so as to indicate the short-term health (e.g., the risk of the patient experiencing an acute event in the near future), the chronic burden or CCB (e.g., the risk of the patient being admitted to an ICU and/or hospitalization in the intermediate future), and lifestyle choice (e.g., adherence to one or more lifestyle choice prescriptions) of the patient. The short-term health may include a first dimension of the health risk score. The CCB score may include a second health dimension of the health risk score. The lifestyle choice may include a third health dimension of the health risk score.

In some embodiments, each dimension of the health risk score of the patient may include a max value of one hundred points with the health risk score including a max value of three hundred points. Alternatively, each of the score may be assigned out of one thousand. Or, the composite score may be assigned out of one thousand. Alternatively, each dimension of the health risk score of the patient may include more or less than one hundred points. For example, the LCC score may include the dietary health choices worth twenty points, the daily routine choices worth twenty points, the dietary harm avoidance choices worth twenty four points, the organized physical activity choices worth sixteen points, and the social and mental balance choices worth twenty points. As another example, the SHC score may include the patient HRQOL input worth one hundred points; the patient HALex input worth one hundred points; or the patient HRQOL input worth fifty points and the patient HALex input worth fifty points for a total of one hundred points. As yet another example, the CCB score in some embodiments may be calculated out of fifty but then may be multiplied by two to normalize the score between zero and one hundred.

In some embodiments, the total health module 116 may generate the SHC score by repeating the same or similar steps discussed above in relation to the graded escalation module 110 generating the SHC score. The total health module 116 may also generate the CCB score by repeating the same or similar steps discussed above in relation to the chronic burden module 108 generating the CCB score. Likewise, the total health module 116 may generate the LCC score by repeating the same or similar steps discussed above in relation to the lifestyle choice module 114 generating the LCC score. Additionally or alternatively, the total health module 116 may obtain the SHC score from the graded escalation module 110, the CCB score from the chronic burden module 108, and/or the LCC score from the lifestyle choice module 114.

The total health module 116 may receive the sensor data from the sensors 120 and 122 related to the quality of health of the patient. The sensor data may include information regarding the state of depression, hypertensions, risk stroke, COPD, diabetes, fall risk, and/or any other appropriate sensor data related to the quality of health of the patient. For example, the sensor data may include GPS data for determining service access such as ER visits, GP follow-ups.

The total health module 116 may direct the questionnaire module 104 to provide one or more questionnaires to the patient via the user device 124. For example. The total health module 116 may direct the questionnaire module 104 to provide the HLPCQ, HRQOL, PHQ2, HLPCQ, or any other appropriate questionnaire to the patient.

The total health module 116 may adjust the number of the questionnaires and/or the number of questions that are included in the questionnaires that are provided to the patient based on previous health risk scores, as warranted. Adjusting the number of questionnaires and/or questions that are provided to the patient as warranted, and as directed by the total health module 116, may improve the functioning of the electronic device 102, the network 118, and/or the user device 124 as described above.

Additionally or alternatively, the total health module 116 may ask the patient if the patient has experienced any changes in the one or more categories (e.g., short-term health, chronic burden, and/or lifestyle choices). The number of the questionnaires and/or the number of questions that are included in the questionnaires that are provided to the patient via the user device 124 may be determined so as to reduce a number of clicks (e.g., responses to questions) and a minimum number of categories (e.g., categories of health related factors) to determine the health risk score of the patient. In some embodiments, the minimum number of clicks may be three clicks or less. Alternatively, the minimum number of clicks may include more than fifteen clicks.

In some embodiments, the total health module 116 may generate the health risk score further based on the sensor data. In these and other embodiments, the total health module 116 may compare the sensor data to known baselines indicated in the chronic data included in the chronic disease database 126. For example, a mean value and/or a standard deviation of sensor of a similar patient may be used as the known baselines. The similar patient may be determined based on similarity of an age, a gender, a race, a geographic location, an education level, an income level, a smoking habit, an alcohol habit, and/or a chronic condition between the patient and the similar patient.

The total health module 116 may categorize the health score for each of the three health dimensions which may include short-term health score, chronic care burden, and lifestyle choice score of the patient.

The total health module 116 may determine the minimum category of questions for high resolution statistical measurement of each dimension of the three health dimensions. For example, the questionnaire may include multiple categories such as "Your Biological Risk Factors", "Your Readiness to Change Health Habits", "Your Capacity of Self-Care", and "Your Social Life." Each category may include questions directed to one or more of the three health dimensions. The minimum number of clicks may be two clicks since the patient only has to identify the category where a change may have occurred and then click the questions related to the category where the change has occurred.

The total health module 116 may quantify each of the three health dimensions of the patient per the VAS health score.

The total health module 116 may generate and provide a health risk result to the physician and/or care-provider. The health risk result may include the health risk score of the patient, one or more of the minimum category of questions for high statistical measurement, and the quantification of each of the three health dimensions of the patient. The health risk result may indicate the likelihood of the patient experiencing an acute event in the near future, or risk of development of a new chronic condition in the near future, or the risk of the patient with at least one chronic disease experiencing a rise in a chronic care burden, and/or the lifestyle health compliance of the patient.

In some embodiments, the total health module 116 may generate a preferential health score. The preferential health score may be based on weighted scores of one or more of the three health dimensions included in the patient input using a sliding score for the VAS score. The three dimensions may be weighted differently based on a particular chronic disease. The health risk result may include the preferential health score. For example, a patient that is being incentivized to improve their health, the preferential score may include a weighted lifestyle choice score since an improved lifestyle is desired In some embodiments, the health risk result may be stored in the memory 117 and/or the total health module 116 as a first health risk result. After the specified period of time, the chronic burden module 108 may repeat the steps described above and may generate a second health risk result. The specified period of time may be equal to or greater than two weeks. In some embodiments, the specified period of time may be less than two weeks.

The total health module 116 may compare the first health risk result to the second health risk result to determine a trend of the health of the patient. If the trend of the health of the patient is improving, the second health risk result may be provided to the physician and/or care-provider and may be stored in the memory 117 and/or the total health module 116. If the trend of the health of the patient is declining, an alert including the second health risk result and/or a difference between the first health risk result and the second health risk result may be generated and provided to the physician and/or care provider. The alert may indicate that the trend of the health of the patient is declining and that the patient should have additional in person examination performed by the physician and/or care-provider as soon as possible.

In some embodiments, the total health module 116 may perform graded escalation on the health score for each of the three health dimensions where a patient may be considered to be at risk as their score falls below the threshold for the given category In some embodiments, for short-term health, it may include a change that is more than one standard deviation below a change observed in that the short-term health; for chronic care burden, it may be based on whether the risk score is greater than thirty out of one hundred; and for the lifestyle choice score, it may also include a change that is more than one standard deviation below a change in the lifestyle choice.

In some embodiments, the total health module 116 may collect a health risk score of a similar patient. For example, the health risk score of the similar patient may be based on the chronic data included in the chronic disease database 126 related to patients that have similar health issues as the patient, patients that have similar demographic characteristics, patients that have similar bio-profiles, and/or any other appropriate patient characteristic that may be used to determine similarity. The total health module 116 may compare the health risk score of the similar patient to the health risk score of the patient. The health risk score may be based on the comparison of the health risk score of the similar patient to the health risk score of the patient.

In some embodiments, the total health module 116 may compare each of the three dimensions of health of the health risk score of the similar patient to the corresponding dimension of health of the health risk score of the patient. In these and other embodiments, the health risk score may be based on the comparison of each dimension of health of the health risk score of the similar patient to the corresponding dimension of health of the health risk score of the patient (e.g., an expected baseline).

A weakness of the questionnaire-based health assessment may be in the fact that a patient may deliberately and misleadingly present himself to be significantly sicker, for example, to obtain earlier appointments. If widely practiced, such an approach can unfortunately dilute the benefit of such health scoring and assessment systems. Thus, the system may also encompass a reliability evaluation module (not illustrated). Score vector $v_1$ may represent patient's health assessment (or, assessment of a key category such as general self-reported health) on k different occasions where he was evaluated by the physician and the vector $v_2$ may represents the doctor's health assessment (or, assessment of a key category such as general self-reported health). Both vectors may be a k-dimensional vector, with entry i represents the score on the $i^{th}$ occasion. The module may compute the difference between the patient assessed health and the doctor's assessed health and based on that may compute the reliability index which may be used to compute the adjustment index which may correspond to the quantity by which the patient reported score is adjusted in the future. A larger the difference between vector $v_1$ and vector $v_2$, larger is the adjustment that may be applied. One way to compute the adjustment index may be through the mean squared difference between the assessments through using the L2 norm and dividing by k:

$$\epsilon = \frac{1}{k}\|v_1 - v_2\|_2^2$$

It may be used $$\frac{1}{\epsilon}$$

as our weighting factor to determine a user's "trustworthiness" in self-reported health.

The under-diagnosis module 112 may include software executable by or on the electronic device 102. For example, the under-diagnosis module 112 may include code stored on the electronic device 102 that may be executed line-by-line by the processor of the electronic device 102 and/or may be loaded into the memory 117 and executed by the processor of the electronic device 102 to perform or control performance of one or more operations described herein in connection with the under-diagnosis module 112. Alternatively or additionally, the under diagnosis module 112 may be implemented in hardware, e.g., as an ASIC, an FPGA, or other hardware device configured to perform or control performance of one or more operations described herein in connection with the under-diagnosis module 112.

The under-diagnosis module 112 may be configured to evaluate relative risk of under-diagnosis of a patient based on the EHR data included in the EHR database 128, the chronic data included in the chronic disease database 126, and/or the patient HRQOL input. The under-diagnosis module 112 may be configured to predict under-diagnosis in one or more chronic diseases, such as alcohol abuse, arthritis, asthma, cancer, cardiovascular disease, COPD, diabetes, disability, immunization, mental health, nutrition, physical activity, weight status, oral health, and/or other chronic disease(s).

The under-diagnosis module 112 may receive the chronic data from the chronic disease database 126. The chronic data may include data that indicates a number of patients that are diagnosed with one or more chronic diseases in a geographic location and/or for a given demographic. The number of patients that are diagnosed with one or more chronic diseases in a geographic location may be based on epidemiological attributes of the patients. For example, the chronic data may include data indicating whether the patients have experienced poor mental and/or physical health in the last day, ten days, thirty days, or any other appropriate range of time. Additionally, the chronic data may be adjusted based on statistical data related to age, ethnicity, gender, income level, education level, and/or geographic locations of the patients.

The under-diagnosis module 112 may receive the EHR data from the EHR database 128. The EHR data may include data indicating the number of patients that are diagnosed with one or more chronic diseases in a practice of a physician. Additionally, the EHR data may include data that indicates the number of patients in the practice of the physician with a higher risk for one or more chronic diseases. The under-diagnosis module 112 may determine whether a patient is at a higher risk or not based on, e.g., the sensor data related to the quality of health of the patients collected by the sensors 120 and 122.

The under-diagnosis module 112 may compare the number of patients diagnosed with a chronic disease in the practice of the physician included in the EHR data to the number of patients diagnosed with the same chronic disease in the geographic location included in the chronic data. The under-diagnosis module 112 may compare and/or analyze all of the patients that visit the physician. Additionally or alternatively, the under-diagnosis module 112 may compare the number of patients with a higher risk for a chronic disease in the practice of the physician included in the EHR data to the number of patients with a higher risk for the same chronic disease in the geographic location included in the chronic data. For example, the number of patients diagnosed with or at higher risk for the chronic disease in the practice of the physician may be compared to one or more tables included in some appropriate database, such as the CDC database.

The under-diagnosis module 112 may generate a comparison result. The comparison result may indicate whether the number of patients diagnosed with the chronic disease in the practice of the physician is greater than or less than the number of patients diagnosed with the chronic disease in the geographic location. Additionally or alternatively, the comparison result may indicate whether the number of patients at a higher risk for the chronic disease in the practice of the physician is greater than or less than the number of patients at a higher risk for the chronic disease in the geographic location or at some selected practices of other physicians, clinics or hospitals. In another embodiment of the invention, a reference database may be selected to match the demographic attributes of the patients of the given physician.

In another embodiment of the invention, the under-diagnosis module 112 may include a reference baseline that can evaluate data from one or more sensors configured to provide data related to a quality of health of a patient that pertains to, includes, and/or indicates at least one of diet pattern, sleep pattern, exercise pattern, activity level, heart rate, posture, stress, blood pressure variation, blood glucose, heart rhythm, smoking status, pain level, and/or GPS data of the patient. In some embodiments, sensors or meta-sensors may include a set of sensors and associated analysis algorithms that provide the required qualitative or quantitative label.

If the number of patients diagnosed with the chronic disease in the practice of the given physician is less than the number of patients diagnosed with the chronic disease in the geographic location and/or if the number of patients at a higher risk for the chronic disease in the practice of the physician is less than the number of patients at a higher risk for the chronic disease in the geographic location, the under diagnosis module 112 may generate and provide the alert to the physician and/or care provider. The alert may include the comparison result and may indicate that the number of patients diagnosed with the chronic disease in the practice of the physician is less than the number of patients diagnosed with the chronic disease in the geographic location and/or if the number of patients at a higher risk for the chronic disease in the practice of the physician is less than the number of patients at a higher risk for the chronic disease in the geographic location or at select practices or clinics or hospitals. In another embodiment, the reference database may provide information about the demographic characteristics of the set of patients that were initially underdiagnosed.

In some embodiments, the EHR data may include data that indicates a number of patients in the practice of the physician that have undergone a laboratory-based screening test for a chronic disease. In these and other embodiments, the under-diagnosis module 112 may compare the number of patients diagnosed with the chronic disease in the geographic location included in the chronic data to the number of patients in the practice of the physician that have undergone laboratory-based screening test for the same chronic disease included in the EHR data. The comparison result may be further based on the comparison of the number of patients diagnosed with the chronic disease in the geographic location to the number of patients in the practice of the physician that have undergone laboratory-based screening test for the same chronic disease.

In some embodiments, the EHR data may include data that indicates a number of patients in the practice of the physician that have been stratified as having a higher risk for a chronic disease based on a physician annotated diagnosis. In these and other embodiments, the under diagnosis module 112 may compare the number of patients diagnosed with the chronic disease in the geographic location included in the chronic data to the number of patients in the practice of the physician that have been stratified as having a higher risk for the same chronic diseases based on the physician annotated diagnosis included in the EHR data. The comparison result may also be based on the comparison of the number of patients diagnosed with the chronic disease in the geographic location to the number of patients in the practice of the physician that have been stratified as having a higher risk for the same chronic disease based on the physician annotated diagnosis.

In some embodiments, the EHR data may include data that indicates a number of patients in the practice of the physician with a higher risk for a chronic disease using the sensor data related to the quality of health of the patients. In these and other embodiments, the sensor data related to the quality of health of the patients may be based on at least one of a diet pattern, a sleep pattern, and/or an exercise pattern of the patients included in the EHR data.

In some embodiments, the EHR data may include data that indicates a number of patients in the practice of the physician that have been stratified as having a higher risk for one or more chronic diseases based on patient responses to one or more questionnaires provided to the patient by the disease calculator 106. In these and other embodiments, the under diagnosis module 112 may compare the number of patients diagnosed with the same chronic disease in the geographic location included in the chronic data to the number of patients in the practice of the physician that have been stratified as having a higher risk for the chronic disease based on patient responses to one or more questionnaires provided to the patient by the disease calculator 106 included in the EHR data. The comparison result may also be based on the comparison of the number of patients diagnosed with the chronic disease in the geographic location to the number of patients in the practice of the physician that have been stratified as having a higher risk for the same chronic disease based on patient responses to one or more questionnaires provided to the patient by the disease calculator 106.

In some embodiments, the EHR data may include data that indicates a number of patients in the practice of the physician with poor compliance to medical recommendations by the physician (e.g., lifestyle choice prescriptions generated by the lifestyle choice module 114). In these and other embodiments, the under-diagnosis module 112 may compare the number of patients diagnosed with a chronic disease in the geographic location included in the chronic data to the number of patients in the practice of the physician with poor compliance to the medical recommendations by the physician included in the EHR data. The comparison result may be further based on the comparison of the number of patients diagnosed with the chronic disease in the geographic location to the number of patients in the practice of the physician with poor compliance to the medical recommendations by the physician.

In some embodiments, the chronic data may include data that indicates population norms and expected deviation for a chronic disease for short-term HRQOL of the patients using the patient HALex input included in the chronic data. In these and other embodiments, the under diagnosis module 112 may compare the population norms and expected deviation for the chronic disease for short-term HRQOL using the patient HALex input included in the chronic data to the number of patients diagnosed with the same chronic disease in the practice of the physician included in the EHR data. The comparison result may be further based on the comparison of the population norms and expected deviation for the chronic disease for short-term HRQOL using the patient HALex input to the number of patients diagnosed with the same chronic disease in the practice of the physician.

In some embodiments, the chronic data may include data that indicates population norms and expected deviation for a chronic disease for short-term HRQOL using a VAS HRQOL score. In some embodiments, the VAS HRQOL may be based on patients rating their health from zero to one hundred where zero may indicate poor health and one hundred may indicate the best health a patient can imagine. In other embodiments, the VAS HRQOL may be based on a score of negative twenty to twenty where negative twenty may indicate a health status worse than death, Additionally, these scores may be normalized from zero to one hundred. For example, twenty may be added to all the scores and then the scores may be scaled back in the range zero to one hundred. The population level norms may be obtained by collecting the scores over a sufficiently large sample such that there is statistically enough patients in each category of the score. The categories may include an age, a gender, a race, a geographic location, an education level, an income level, a smoking habit, an alcohol habit, and/or a chronic condition of the patients. In these and other embodiments, the under diagnosis module 112 may compare the population norms and expected deviation for the chronic disease for short-term HRQOL using the VAS HRQOL score included in the chronic data to the number of patients diagnosed with the same chronic disease in the practice of the physician included in the EHR data. The comparison result may be further based on the comparison of the population norms and expected deviation for the chronic disease for short-term HRQOL using the VAS HRQOL score to the number of patients diagnosed with the same chronic diseases in the practice of the physician.

Figure 2:
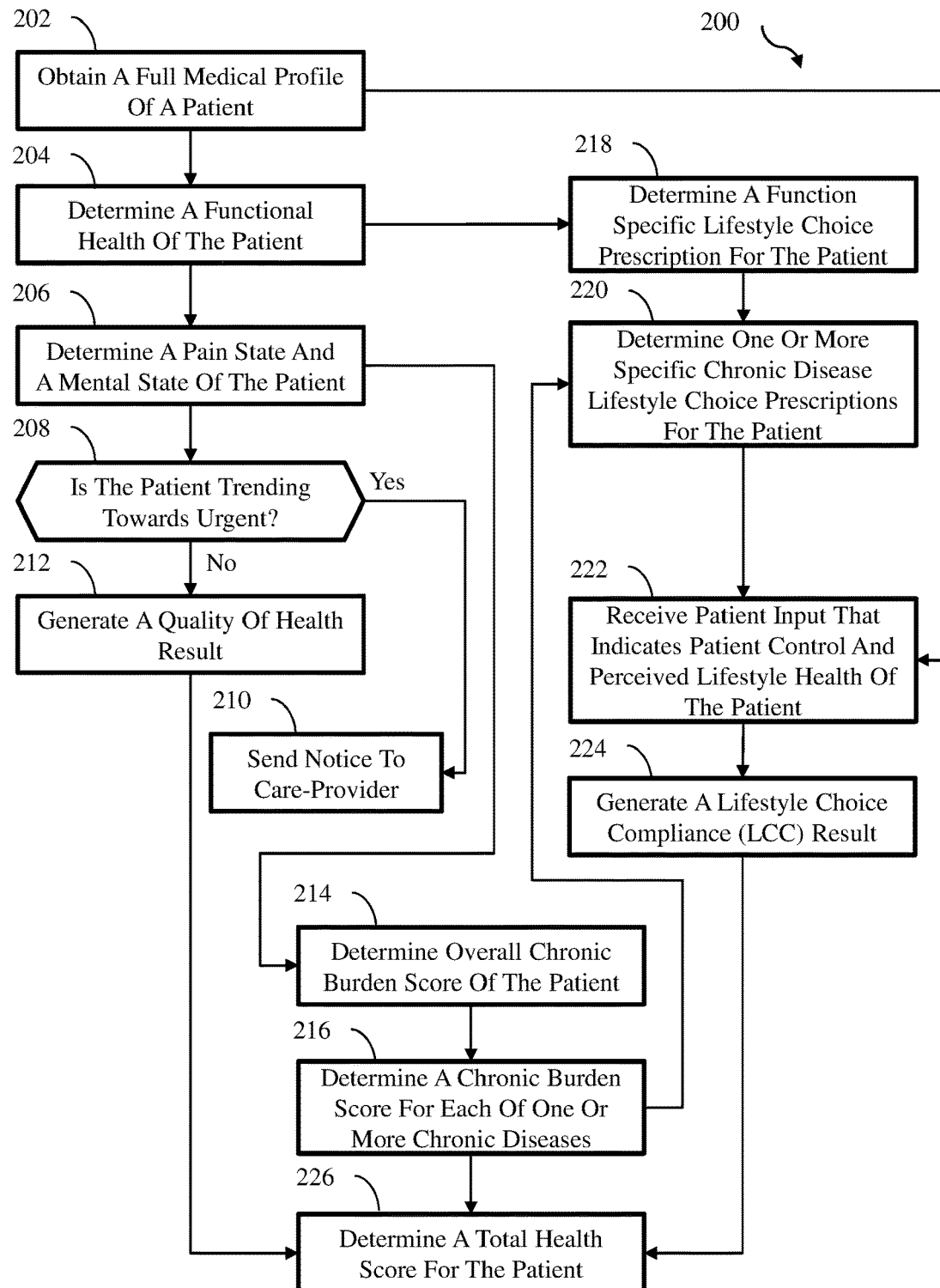
FIG. 2 is a flow diagram of an example method to generate a total health score of a patient.

FIG. 2 is a flow diagram of an example method 200 to generate a total health score of a patient, arranged in accordance with at least one embodiment described herein. The method 200 may be performed, in whole or in part, by an electronic device such as the electronic device 102 of FIG. 1, the sensors 120, 122, the user device 124, and/or one or more other systems or devices. In some embodiments, the electronic device may have access to a chronic disease database, such as the chronic disease database 126 of FIG. 1 and/or an EHR database such as the EHR database 128 of FIG. 1. Alternatively or additionally, the electronic device may have access to one or more sensors, such as the sensors 120 and 122 of FIG. 1.

The method 200 may be performed, in whole or in part, by the electronic device. Alternatively or additionally, the method 200 may be implemented by a processor device that performs or controls performance of one or more of the operations of the method 200. For instance, a computer (such as a computing device 1400 of FIG. 14) or other processor device may be communicatively coupled to the electronic device and/or may be included as a control system of the electronic device and may execute software or other computer-readable instructions accessible to the computer, e.g., stored on a non-transitory computer-readable medium accessible to the computer, to perform or control the electronic device to perform the method 200 of FIG. 2.

The method 200 may include one or more of blocks 202, 204, 206, 208, 210, 212, 214, 216, 218, 220, 222, 224, and/or 226. Although illustrated as discrete blocks, various blocks may be divided into additional blocks, supplemented with additional blocks, combined into fewer blocks, or eliminated, depending on the particular implementation. The method 200 may begin at block 202.

In block 202 ("Obtain A Full Medical Profile of A Patient") a full medical profile of a patient may be obtained. The full medical profile of the patient may be based on the EHR data, such as the EHR data included in the EHR database 128 of FIG. 1. Block 202 may be followed by block 204.

In block 204 ("Determine A Functional Health Of The Patient"), a functional health of the patient may be determined. In an example, the functional health of the patient may be determined based on patient HALex input as discussed elsewhere herein. Block 204 may be followed by block 206.

In block 206 ("Determine A Pain State And A Mental State Of The Patient"), a pain state and a mental state of the patient may be determined. In an example, the pain state of the patient may be determined based on patient input provided on an avatar as discussed elsewhere herein. The mental state of the patient may be determined based on patient PHQ2 input as discussed elsewhere herein. Block 206 may be followed by block 208.

In block 208 ("Is The Patient Trending Towards Urgent"), it may be determined whether the patient is trending towards urgent. If the patient is trending towards urgent, block 208 may be followed by block 210. If the patient is not trending towards urgent, block 208 may be followed by block 212.

In block 210 ("Send Notice Care-Provider"), a notice may be sent to the care-provider. In some embodiments, the care-provider may include a physician of the patient. The notice (e.g., the alert) may include the quality of health result. The notice may indicate that the patient is likely to experience an acute event in the near future and should have additional in person examination performed by the physician and/or care-provider as soon as possible.

In block 212 ("Generate A Quality Of Health Result"), a quality of health result may be generated. The quality of health result may be based on the pain state, mental state, functional health, and/or full patient set of the patient. The quality of health result may be the same or similar to the SHC result discussed elsewhere herein. Block 212 may be followed by block 226.

In block 214 ("Determine Overall Chronic Burden Score Of The Patient"), an overall chronic burden score (e.g., a CCB score) of the patient may be determined. The overall chronic burden score may be the same or similar to the CCB score discussed elsewhere herein. The overall chronic burden score may be based on all chronic diseases the patient is diagnosed with. Alternatively or additionally, the overall chronic burden score may be based on the pain state and the mental state of the patient determined in block 206. Block 214 may be followed by block 216.

In block 216 ("Determine A Chronic Burden Score For Each Of One Or More Chronic Diseases"), an individual chronic burden score for each of one or more chronic diseases may be determined. Each individual chronic disease burden score may be determined based on a single chronic disease that the patient is experiencing. The individual chronic burden score for each of the one or more chronic diseases may be similar to the overall chronic burden score but related to a single chronic disease. Block 216 may be followed by block 226.

In block 218 ("Determine A Function Specific Lifestyle choice Prescription For The Patient"), a function specific lifestyle choice prescription for the patient may be determined. The function specific lifestyle choice prescription may be determined based on the functional health of the patient determined in block 214. The function specific lifestyle choice prescription may be the same or similar to the lifestyle choice prescription generated by the lifestyle choice module 114 of FIG. 1. Block 218 may be followed by block 220.

In block 220 ("Determine One Or More Specific Lifestyle Choice Prescriptions For The Patient"), one or more specific lifestyle choice prescriptions for the patient may be determined. The one or more specific lifestyle choice prescriptions may be directed to reduce an impact that one or more chronic diseases are having on the patient. The one or more specific lifestyle choice prescriptions for the patient may be determined based on the overall chronic burden score and/or the individual chronic burden score for each of the one or more chronic diseases determined in block 216. Block 220 may be followed by block 222.

In block 222 ("Receive Patient Input That Indicates Patient Control And Perceived Lifestyle Health Of The Patient"), patient input that indicates patient control and perceived lifestyle health of the patient may be received. The patient input may include the patient HLPCQ input and/or the patient LRSQ input discussed elsewhere herein. Block 222 may be followed by block 224.

In block 224 ("Generate A LCC Result") a LCC result may be generated. The LCC result may include an LCC score. The LCC result and/or the LCC score may be the same or similar to the LCC result and/or LCC score generated by the lifestyle choice module 114 of FIG. 1. Block 224 may be followed by block 226.

In block 226 ("Determine A Total Health Score For The Patient"), a total health score for the patient may be determined. The total health score may be determined based on the quality of health result generated in block 212, the chronic burden score for the one or more chronic diseases determined in block 216, and/or the LCC result determined in block 224. The total health score may be the same or similar to the health risk score generated by the total health module 116 of FIG. 1.

One skilled in the art will appreciate that, for this and other processes, operations, and methods disclosed herein, the functions and/or operations performed may be implemented in differing order. Furthermore, the outlined functions and operations are only provided as examples, and some of the functions and operations may be optional, combined into fewer functions and operations, or expanded into additional functions and operations without detracting from the essence of the disclosed embodiments.

Figure 3:
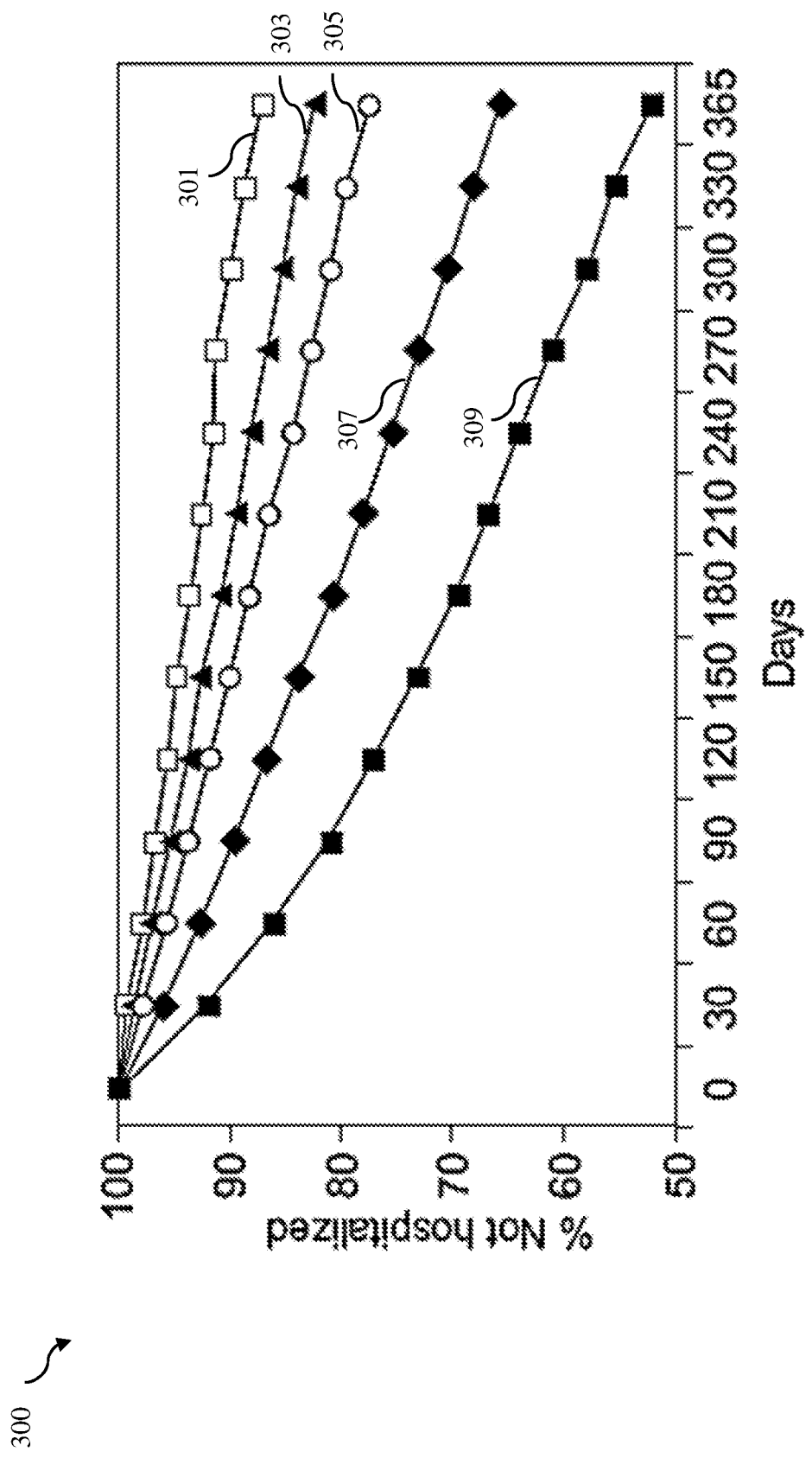
FIG. 3 is a graphical representation of a number of Medicare patients that are not hospitalized within a year of providing a patient general health input.

FIG. 3 is a graphical representation 300 of a number of Medicare patients that are not hospitalized within a year of providing a patient general health input, arranged in accordance with at least one embodiment described herein. Curves 301, 303, 305, 307, and 309 respectively represent the percentage of the Medicare patients that were not hospitalized within a year of providing the patient general health input that indicates excellent, very good, good, fair, and poor perceived general health of the patients.

For the curve 301, corresponding to the patient general health input that indicates excellent perceived general health of the patients, the number of patients that were not hospitalized decreased as the year progressed. For example, one hundred percent of the patients were not hospitalized at day zero, roughly ninety five percent of the patients were not hospitalized at roughly day one hundred ninety five, and roughly eighty eight percent of the patients were not hospitalized at day three hundred sixty five.

For the curve 303, corresponding to the patient general health input that indicates very good perceived general health of the patients, the number of patients that were not hospitalized also decreased as the year progressed. For example, one hundred percent of the patients were not hospitalized at day zero, roughly ninety two percent of the patients were not hospitalized at roughly day one hundred ninety five, and roughly eighty three percent of the patients were not hospitalized at day three hundred sixty five.

For the curve 305, corresponding to the patient general health input that indicates good perceived general health of the patients, the number of patients that were not hospitalized similarly decreased as the year progressed. For example, one hundred percent of the patients were not hospitalized at day zero, roughly eighty seven percent of the patients were not hospitalized at roughly day one hundred ninety five, and roughly seventy eight percent of the patients were not hospitalized at day three hundred sixty five.

For the curve 307, corresponding to the patient general health input that indicates fair perceived general health of the patients, the number of patients that were not hospitalized also decreased as the year progressed. For example, one hundred percent of the patients were not hospitalized at day zero, roughly seventy eight percent of the patients were not hospitalized at roughly day one hundred ninety five, and roughly sixty six percent of the patients were not hospitalized at day three hundred sixty five.

For the curve 309, corresponding to the patient general health input that indicates poor perceived general health of the patients, the number of patients that were not hospitalized decreased more quickly as the year progressed. For example, one hundred percent of the patients were not hospitalized at day zero, roughly sixty seven percent of the patients were not hospitalized at roughly day one hundred ninety five, and roughly fifty three percent of the patients were not hospitalized at day three hundred sixty five.

As can be seen in the graphical representation 300, a strong correlation between perceived general health of the patients and likelihood of hospitalization of the patient within a year exists.

Figure 4:
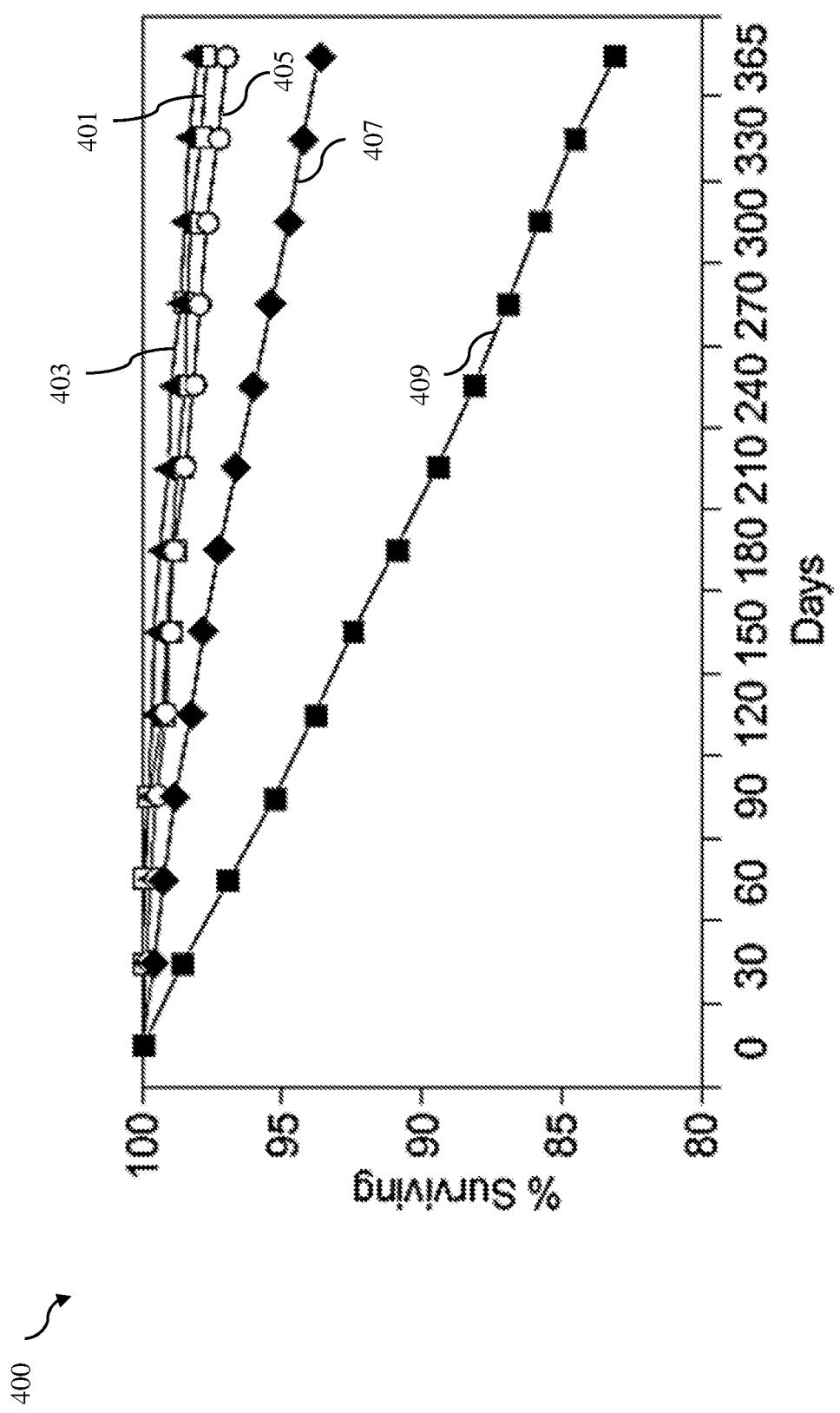
FIG. 4 is a graphical representation of a number of Medicare patients that do not die within a year of providing a patient general health input.

FIG. 4 is a graphical representation 400 of a number of Medicare patients that do not die within a year of providing a patient general health input, arranged in accordance with at least one embodiment described herein. Curves 401, 403, 405, 407, and 409 respectively represent the percentage of the Medicare patients that did not die within a year of providing patient general health input that indicates excellent, very good, good, fair, and poor perceived general health of the patients.

For the curve 401, corresponding to the patient general health input that indicates excellent perceived general health of the patients, the number of patients that did not die decreased as the year progressed. For example, one hundred percent of the patients did not die by day zero, roughly ninety nine percent of the patients did not die by roughly day one hundred ninety five, and roughly ninety eight percent of the patients did not die by day three hundred sixty five.

For the curve 403, corresponding to the patient general health input that indicates very good perceived general health of the patients, the number of patients that did not die also decreased as the year progressed. For example, one hundred percent of the patients did not die by day zero, roughly ninety nine percent of the patients did not die by roughly day one hundred ninety five, and roughly 97.5 percent of the patients did not die by day three hundred sixty five.

For the curve 405, corresponding to the patient general health input that indicates good perceived general health of the patients, the number of patients that did not die similarly decreased as the year progressed. For example, one hundred percent of the patients did not die by day zero, roughly ninety seven percent of the patients did not die by roughly day one hundred ninety five, and roughly 96.5 percent of the patients did not die by day three hundred sixty five.

For the curve 407, corresponding to the patient general health input that indicates fair perceived general health of the patients, the number of patients that did not die also decreased as the year progressed. For example, one hundred percent of the patients did not die by day zero, roughly ninety six percent of the patients did not die by roughly day one hundred ninety five, and roughly ninety four percent of the patients did not die by day three hundred sixty five.

For the curve 409, corresponding to the patient general health input that indicates poor perceived general health of the patients, the number of patients that did not die decreased more quickly as the year progressed. For example, one hundred percent of the patients did not die by day zero, roughly eighty nine percent of the patients did not die by roughly day one hundred ninety five, and roughly eight four percent of the patients did not die by day three hundred sixty five.

As can be seen in the graphical representation 400, a strong correlation between perceived general health of the patients and likelihood of death of the patient within a year exists.

Figure 5:
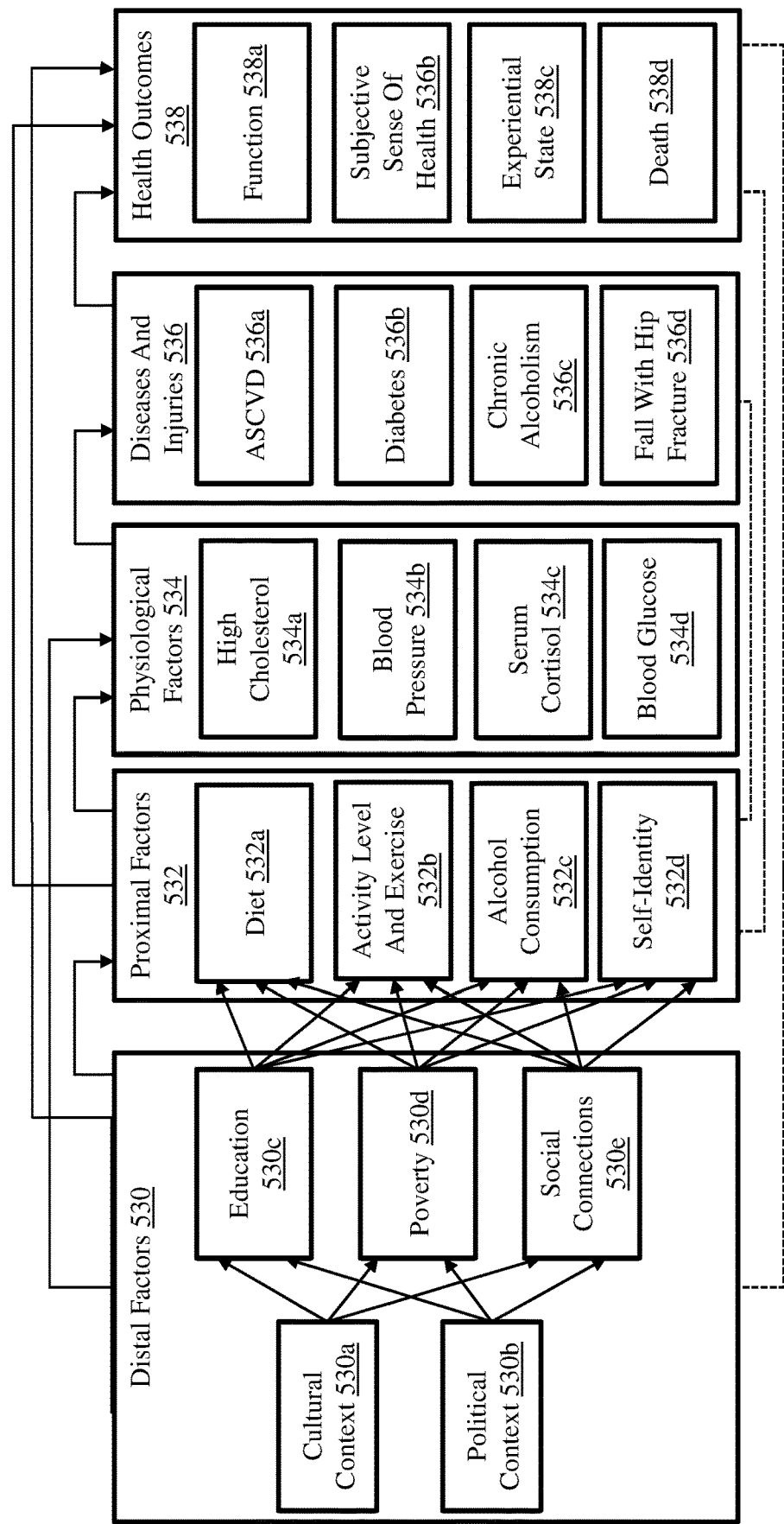
FIG. 5 is a graphical representation of how various factors may impact management of chronic diseases.

FIG. 5 is a graphical representation 500 of how various factors may impact management of chronic diseases, in accordance with at least one embodiment of the present disclosure. Example factors of the patient that may impact management of chronic diseases may include distal factors 530, proximal factors 532, physiological factors 534, diseases and injuries 536, and/or health outcomes 538 of the patient.

Potential causal relationships (e.g., relationships that may have an impact on a different factor) within the factors are illustrated as solid lines in the graphical representation 500. For example, the distal factors 530 of the patient may have a causal relationship with the proximal factors 532, the physiological factors 534, and/or the health outcomes 538 of the patient. As another example, the proximal factors 532 of the patient may have a causal relationship with the physiological factors 534 and/or the health outcomes 538 of the patient. As yet another example, the physiological factors 534 of the patient may have a causal relationship with the diseases and injuries 536 of the patient. As another example, the diseases and injuries 536 of the patient may have a causal relationship with the health outcomes 538 of the patient.

Potential feedback relationships (e.g., relationships that may adjust treatment and diagnosis of a different factor) within the factors are illustrated as dashed lines in the graphical representation 500. For example, the diseases and injuries 536 of the patient may have a feedback relationship with the proximal factors 532 of the patient. As another example, the health outcomes 538 of the patient may have a feedback relationship with the proximal factors 532 and/or the distal factors 530 of the patient.

The distal factors 530 of the patient may include one or more sub-factors including cultural context 530a, political context 530b, education 530c, poverty 530d, and/or social connections 530e. As can be seen in the graphical representation 500, the sub-factors included in the distal factors 530 may impact each other. For example, the education 530c sub-factor may be affected by the cultural context 530a and/or the political context 530b sub-factors.

The proximal factors 532 of the patient may include one or more sub-factors including diet 532a; activity level and exercise 532b; alcohol consumption 532c; and/or self-identity 532d. As shown in the graphical representation 500, the sub-factors included in the proximal factors 532 may be impacted by one or more sub-factors in the distal factors 530. For example, the diet 532a sub-factor may be affected by the education 530c, the poverty 530d, and/or social connections sub-factors.

The physiological factors 534 of the patient may include one or more sub-factors including high cholesterol 534a, blood pressure 534b, serum cortisol 534c, and/or blood glucose 534d. The diseases and injuries 536 of the patient may also include one or more sub-factors including atherosclerotic cardiovascular disease (ASCVD) 536a, diabetes, 536b, chronic alcoholism 536c, and/or fall with hip fracture 536d. Likewise, the health outcomes 538 of the patient may include one or more sub-factors including function 538a, subjective sense of health 536b, experiential state 538c, and/or death 538d.

Both the distal factors 530 and the proximal factors 532 may operate through sub-factors and directly on health outcomes 538 of the patient. For example, a level of education of the patient may directly influence their subjective sense of health 536b and/or level of social function 538a and may also impact the diet 532a and activity level and exercise 532b of the patient.

Figure 6:
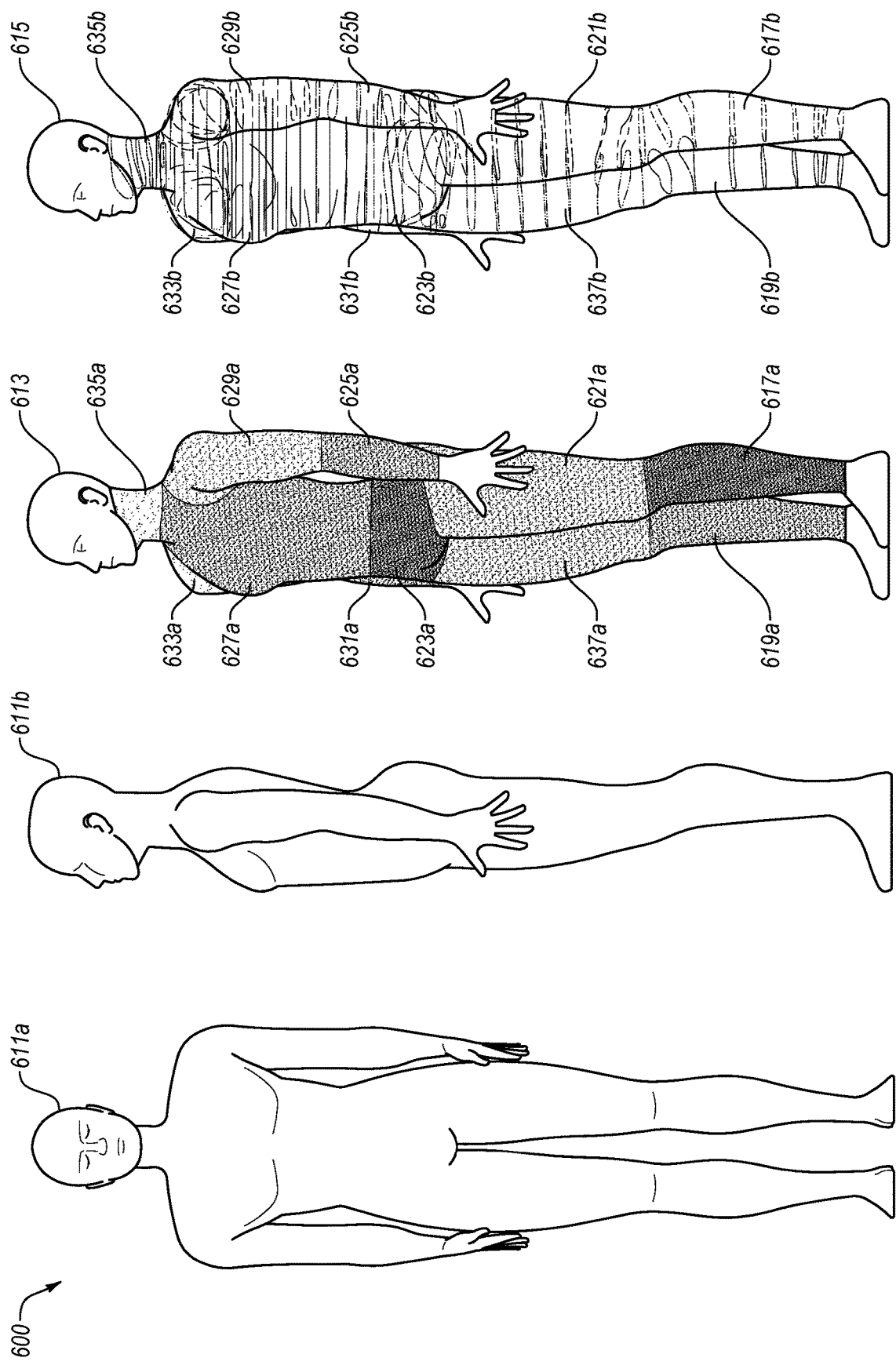
FIG. 6 is a graphical representation of anatomically detailed human avatars.

FIG. 6 is a graphical representation 600 of anatomically detailed human avatars 611a-b, 613, and 615, arranged in accordance with at least one embodiment of the present disclosure. In FIG. 6 a front view of a first avatar 611a and a side view of the first avatar 611b are illustrated. The first avatar 611a-b may be provided to the patient via a user device such as the user device 124 of FIG. 1. The first avatar 611a-b may be anatomically detailed to allow the patient to provide information specific to where the patient is experiencing pain and/or how much pain the patient is experiencing. The information collected via the first avatar 611a-b may be used to determine a VAS score on a VAS pain scale as discussed elsewhere herein.

Additionally, a side view of a second avatar 613 and a side view of a third avatar 615 illustrating different amounts of musculoskeletal pain reported by a patient are illustrated. The second avatar 613 and the third avatar 615 show amounts of reported musculoskeletal pain mapped to corresponding musculoskeletal regions of the second avatar 613 and the third avatar 615. In some embodiments, the second avatar 613 and/or the third avatar 615 may include a lower left leg region 617*a-b*, a lower right leg region 619*a-b*, an upper left leg region 621*a-b*, an upper right leg region 637*a-b*, a groin region 623 *a-b*, a lower right arm region 631*a-b*, a lower left arm region 625*a-b*, a chest region 627*a-b*, an upper left arm region 629*a-b*, an upper right arm region 633*a-b*, and a neck region 635*a-b*.

As illustrated in the second avatar 613, various amounts of musculoskeletal pain as reported by the patient are shown as different hatching covering an entire region of the second avatar 613. As illustrated in the third avatar 615, various amounts of musculoskeletal pain as reported by the patient are shown as different line types within a region of the third avatar 615.

A level of pain associated with a given hatching in the second avatar 613 and/or line type in the third avatar 615 according to an example embodiment will now be described. As illustrated in the second avatar 613 and the third avatar 615, the patient reported experiencing a high level of musculoskeletal pain in the lower left leg region 617*a-b* and the groin region 623*a-b*. As illustrated in the second avatar 613 and the third avatar 615, the patient reported experiencing a very high level of musculoskeletal pain in the lower right leg region 619*a-b*. Additionally, as illustrated in the second avatar 613 and the third avatar 615, the patient reported experiencing an intermediate level of musculoskeletal pain in the chest region 627*a-b*, the lower right arm region 631*a-b*, and the lower right arm region 631*a-b*. Furthermore, as illustrated in the second avatar 613 and the third avatar 615, the patient reported experiencing a low level of musculoskeletal pain in the upper right arm region 633*a-b*, the upper left arm region 629*a-b*, and the neck region 635*a-b*. As illustrated in the second avatar 613 and the third avatar 615, the patient reported experiencing no musculoskeletal pain in the upper right leg region 637*a-b* and the upper left leg region 621*a-b*.

Figure 7:
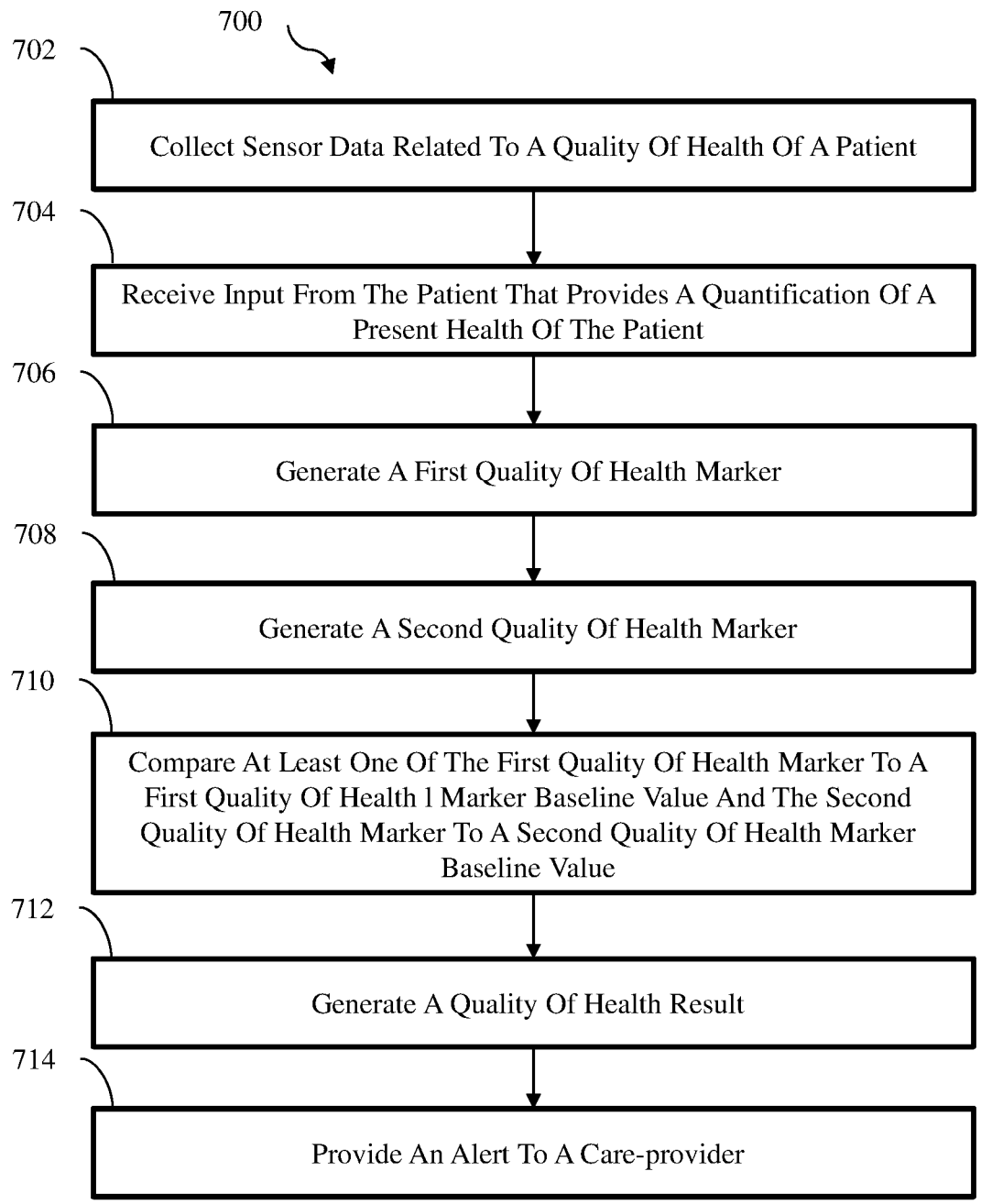
FIG. 7 is a flow diagram of an example method to predict a likelihood of a patient experiencing an acute event in the near future.

FIG. 7 is a flow diagram of an example method 700 to predict a likelihood of a patient experiencing an acute event (e.g., visiting an ER and/or hospitalization) in the near future, arranged in accordance with at least one embodiment described herein. The method 700 may be performed by a graded escalation module such as the graded escalation module 110 of FIG. 1. In some embodiments, the graded escalation module may have access to a chronic disease database, such as the chronic disease database 126 of FIG. 1 and/or an EHR database such as the EHR database 128 of FIG. 1. Additionally, the graded escalation module may have access to one or more sensors, such as the sensors 120 and 122 of FIG. 1.

The method 700 may be performed, in whole or in part, by the graded escalation module. Alternatively or additionally, the method 700 may be implemented by a processor device that performs or controls performance of one or more of the operations of the method 700. For instance, a computer (such as the computing device 1400 of FIG. 14) or other processor device may be communicatively coupled to the graded escalation module and/or may be included as a control system of the graded escalation module and may execute software or other computer-readable instructions accessible to the computer, e.g., stored on a non-transitory computer-readable medium accessible to the computer, to perform or control the graded escalation module to perform the method 700 of FIG. 7.

The method 700 may include one or more of blocks 702, 704, 706, 708, 710, 712, and/or 714. Although illustrated as discrete blocks, various blocks may be divided into additional blocks, supplemented with additional blocks, combined into fewer blocks, or eliminated, depending on the particular implementation. The method 700 may begin at block 702.

In block 702 ("Collect Sensor Data Related To A Quality Of Health Of A Patient"), sensor data related to a quality of health of a patient may be collected. In some embodiments, the sensor data may be collected by the graded escalation module from the sensors. Block 702 may be followed by block 704.

In block 704 ("Receive Input From The Patient That Provides A Quantification Of A Present Health Of The Patient"), input from the patient that provides a quantification of the present health of the patient may be received. The input from the patient may provide a quantification of the present health of the patient using a VAS based health status scale (e.g., a VAS pain scale). In some embodiments, the VAS based health status scale may be obtained by the patient indicating on an avatar a location of pain, an amount of pain, and/or a type of pain that the patient is experiencing. The avatar may include one or more of the avatars 611*a-b*, 613, and/or 615 discussed elsewhere herein. In some embodiments, the patient input may provide a quantification of lifestyle choices of the patient. Block 704 may be followed by block 706.

In block 706 ("Generate A First Quality Of Health Marker"), a first quality of health marker may be generated. The first quality of health marker may be generated based on the sensor data related to the quality of health of the patient and the quantification of the present health of the patient. In some embodiments, the first quality of health marker may be generated based on at least one of the sensor data related to the quality of health of the patient and the patient input. In these and other embodiments, the first quality of health marker may include a first dimension of the quality of health of the patient. Additionally or alternatively, the first quality of health marker may be indicative of additional examination of the quality of health of the patient to be performed.

In some embodiments, the first quality of health marker may include a first dimension of the quality of health of the patient. The first quality of health marker may indicate whether additional examination of the quality of health of the patient is to be performed. Block 706 may be followed by block 708.

In block 708 ("Generate A Second Quality Of Health Marker") a second quality of health marker may be generated. In some embodiments, the second quality of health marker may be based on at least one of the sensor data related to the quality of health of the patient and the patient input. In these and other embodiments, the second quality of health marker may be a second dimension of the quality of health of the patient. Additionally or alternatively, the second quality of health marker may be indicative of additional examination of the quality of health of the patient to be performed.

The second quality of health marker may be generated based on one or more risk stratification algorithms. In some embodiments, the second quality of health marker may indicate an acute assessment of issues related to the quality of health of the patient. In some embodiments, the method 700 may also include generating a third quality of health marker based on one or more risk stratification algorithms. In some embodiments, the third quality of health marker may be a third dimension of the quality of health of the patient. Additionally or alternatively, the third quality of health marker may be indicative of an acute assessment of issues related to the quality of health of the patient.

Additionally, the method 700 may include generating a HICO score based on the first quality of health marker and the second quality of health marker, as discussed in more detail below. Likewise, the method 700 may include generating a BICO score of the patient using lifestyle choices based on at least one of the patient input and the sensor data, as discussed in more detail below. Block 708 may be followed by block 710.

In block 710 ("Compare At Least One Of The First Quality Of Health Marker To A First Quality Of Health Marker Baseline Value And The Second Quality Of Health Marker To A Second Quality Of Health Marker Baseline Value"), at least one of the first quality of health marker may be compared to the first quality of health marker baseline value and the second quality of health marker may be compared to the second quality of health marker baseline value. In some embodiments, the method 700 may also include comparing the HICO score and the BICO score with a set of baseline values. Block 710 may be followed by block 712.

In block 712 ("Generate A Quality Of Health Result"), a quality of health result may be generated. The quality of health result may be based on the comparison of at least one of the first quality of health marker to the first quality of health marker baseline value and the second quality of health marker to the second quality of health marker baseline value. The quality of health result may indicate the likelihood of a patient experiencing an acute event in the near future. Block 712 may be followed by block 714.

In block 714 ("Provide An Alert To A Care Provider"), an alert may be provided to the care-provider. In some embodiments, the care-provider may include a physician of the patient. The alert may include the quality of health result. In some embodiments, the alert is provided only if the quality of health result is below a quality of health threshold amount (e.g., the first quality of health marker is below a first quality of health marker threshold value and/or the second quality of health marker is below a second quality of health marker threshold value), or if the quality of health result has deteriorated from a prior quality of health result by a difference more than a quality of health threshold difference (e.g., an iteration threshold value). In other embodiments, the alert may be provided for each and every quality of health result.

In some embodiments, the alert may include the result of at least one of the comparison of the first quality of health marker to the first quality of health marker baseline value, the second quality of health marker to the second quality of health marker baseline value, the HICO score and the BICO score to the set of baseline values.

Figure 8:
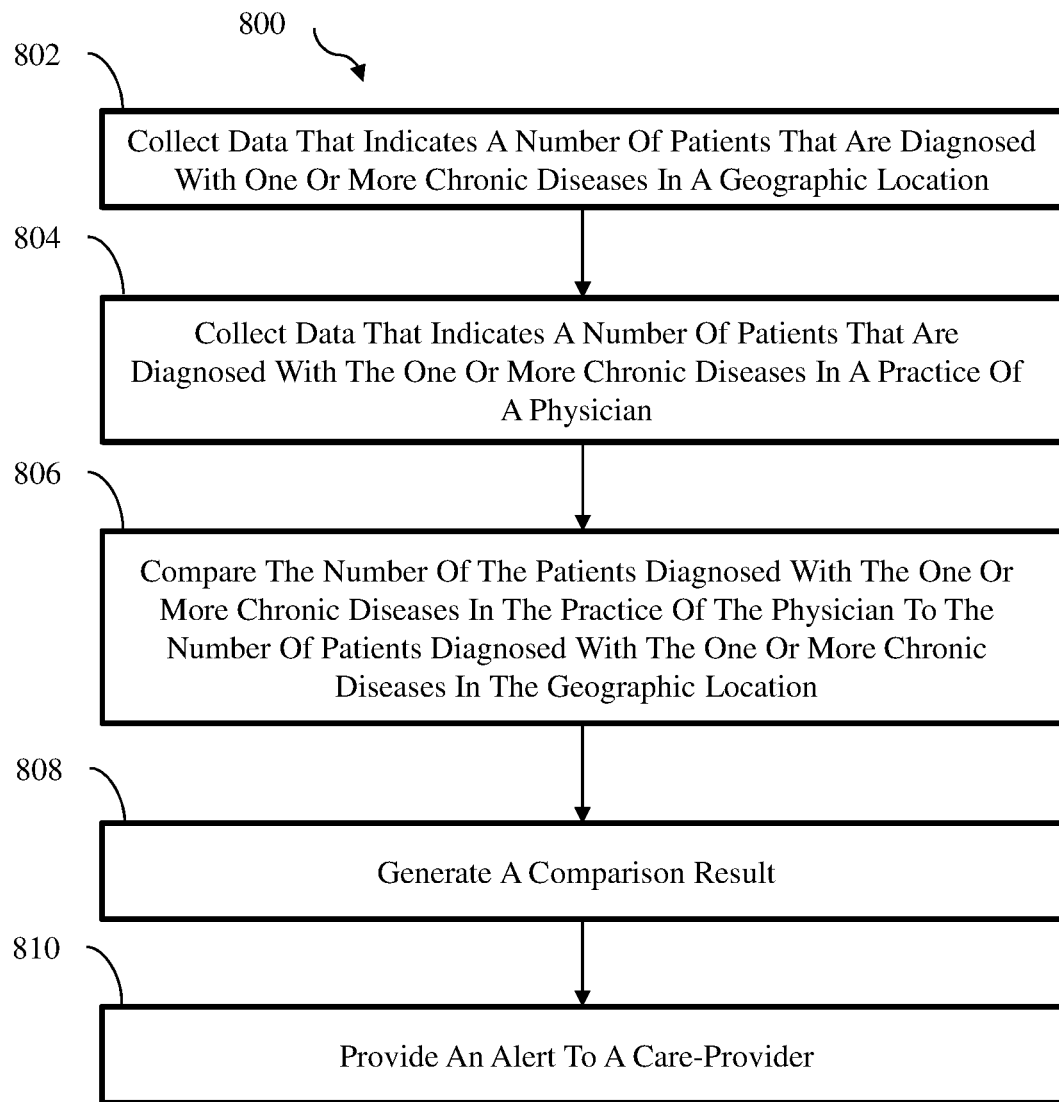
FIG. 8 is a flow diagram of an example method to evaluate relative risk of under-diagnosis of a patient.

FIG. 8 is a flow diagram of an example method 800 to evaluate relative risk of under-diagnosis of a patient, arranged in accordance with at least one embodiment described herein. The method 800 may be performed by an under diagnosis module such as the under diagnosis module 112 of FIG. 1. In some embodiments, the under diagnosis module may have access to a chronic disease database, such as the chronic disease database 126 of FIG. 1 and/or an EHR database such as the EHR database 128 of FIG. 1.

The method 800 may be performed, in whole or in part, by the under diagnosis module. Alternatively or additionally, the method 800 may be implemented by a processor device that performs or controls performance of one or more of the operations of the method 800. For instance, a computer (such as the computing device 1400 of FIG. 14) or other processor device may be communicatively coupled to the under diagnosis module and/or may be included as a control system of the under diagnosis module and may execute software or other computer-readable instructions accessible to the computer, e.g., stored on a non-transitory computer-readable medium accessible to the computer, to perform or control the under diagnosis module to perform the method 800 of FIG. 8.

The method 800 may include one or more of blocks 802, 804, 806, 808, and/or 810. Although illustrated as discrete blocks, various blocks may be divided into additional blocks, supplemented with additional blocks, combined into fewer blocks, or eliminated, depending on the particular implementation. The method 800 may begin at block 802.

In block 802 ("Collect Data That Indicates A Number Of Patients That Are Diagnosed With One Or More Chronic Diseases In A Geographic Location"), data that indicates a number of patients that are diagnosed with one or more chronic diseases in a geographic location may be collected. The data may be obtained from a chronic disease database such as the chronic disease database 126 of FIG. 1. The data may include the chronic data discussed elsewhere herein. Block 802 may be followed by block 804.

In block 804 ("Collect Data That Indicates A Number Of Patients That Are Diagnosed With The One Or More Chronic Diseases In A Practice Of A Physician"), data that indicates a number of patients diagnosed with the one or more chronic diseases in a practice of a physician may be collected. The data may be obtained from an EHR database such as the EHR database 128 of FIG. 1. The data may include the EHR data discussed elsewhere herein. Block 804 may be followed by block 806.

In block 806 ("Compare The Number Of The Patients Diagnosed With The One Or More Chronic Diseases In The Practice Of The Physician To The Number Of Patients Diagnosed With The One Or More Chronic Diseases In The Geographic Location"), the number of the patients diagnosed with the one or more chronic diseases in the practice of the physician may be compared to the number of patients diagnosed with the one or more chronic diseases in the geographic location. Block 806 may be followed by block 808.

In block 808 ("Generate A Comparison Result") a comparison result may be generated. The comparison result may indicate whether the number of patients diagnosed with the one or more chronic diseases in the practice of the physician is greater than or less than the number of patients diagnosed with the one or more chronic diseases in the geographic location. Alternatively or additionally, the comparison result may include a difference between the number of patients diagnosed with the one or more chronic diseases in the practice of the physician and the number of patients diagnosed with the one or more chronic diseases in the geographic location. Block 808 may be followed by block 810.

In block 810 ("Provide An Alert To A Care Provider"), an alert may be provided to the care-provider. The alert may include the comparison result. In some embodiments, the care-provider may include a physician of the patient. In some embodiments, the alert is provided only if the comparison result indicates the number of patients diagnosed with the one or more chronic diseases in the practice of the physician is less than the number of patients diagnosed with the one or more chronic diseases in the geographic location and/or if the number of patients at a higher risk for the one or more chronic diseases in the practice of the physician is less than the number of patients at a higher risk for the chronic disease in the geographic location. In other embodiments, the alert may be provided for each and every comparison result.

Figure 9:
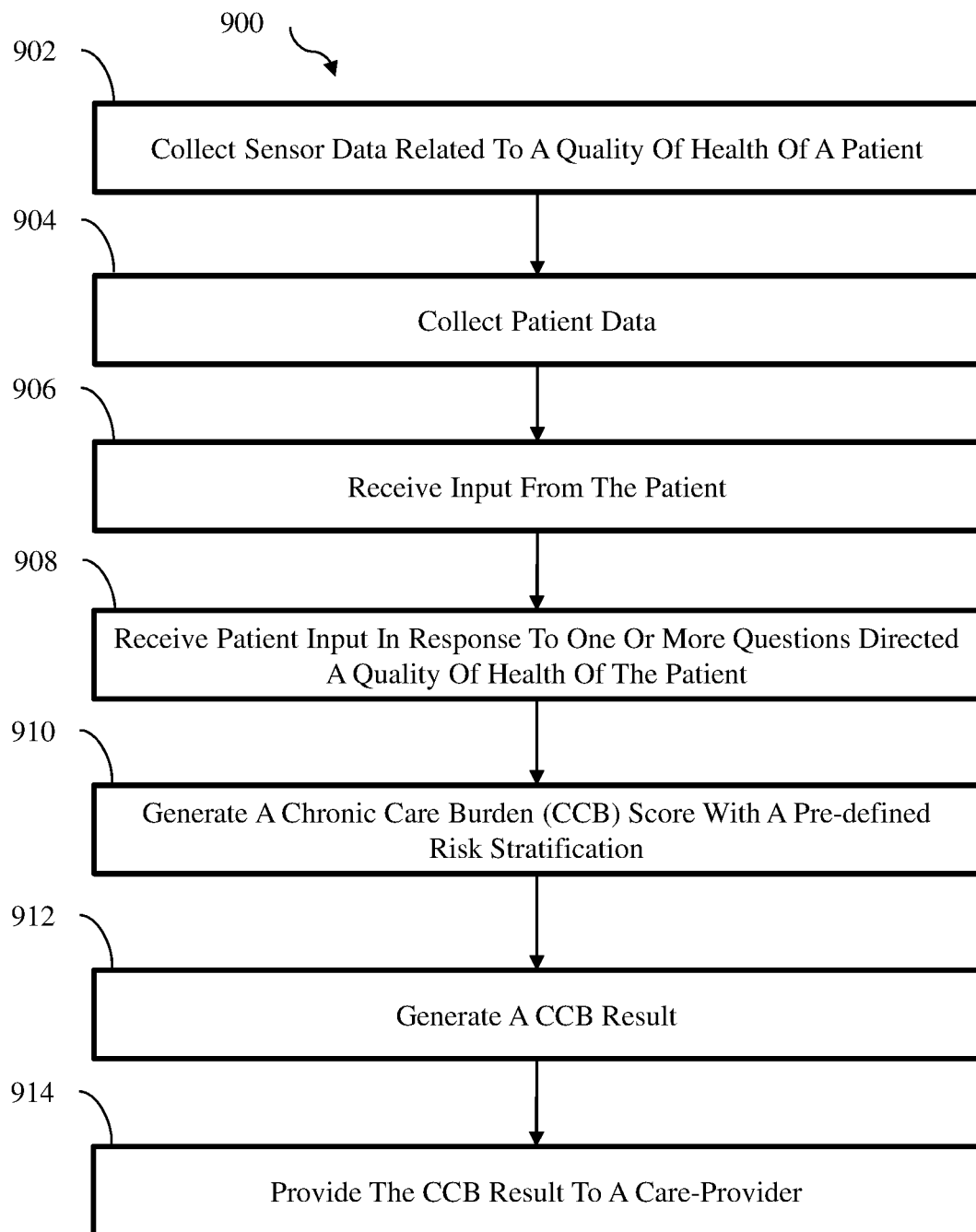
FIG. 9 is a flow diagram of an example method to evaluate and stratify a chronic care burden of a patient.

FIG. 9 is a flow diagram of an example method 900 to evaluate and stratify a chronic care burden of a patient, arranged in accordance with at least one embodiment described herein. The method 900 may be performed by a chronic burden module such as the chronic burden module 108 of FIG. 1. In some embodiments, the chronic burden module may have access to a chronic disease database, such as the chronic disease database 126 of FIG. 1 and/or an EHR database such as the EHR database 128 of FIG. 1. Additionally, the chronic burden module may have access to one or more sensors, such as the sensors 120 and 122 of FIG. 1.

The method 900 may be performed, in whole or in part, by the chronic burden module. Alternatively or additionally, the method 900 may be implemented by a processor device that performs or controls performance of one or more of the operations of the method 900. For instance, a computer (such as the computing device 1400 of FIG. 14) or other processor device may be communicatively coupled to the chronic burden module and/or may be included as a control system of the chronic burden module and may execute software or other computer-readable instructions accessible to the computer, e.g., stored on a non-transitory computer-readable medium accessible to the computer, to perform or control the chronic burden module to perform the method 900 of FIG. 9.

The method 900 may include one or more of blocks 902, 904, 906, 908, 910, 912, and/or 914. Although illustrated as discrete blocks, various blocks may be divided into additional blocks, supplemented with additional blocks, combined into fewer blocks, or eliminated, depending on the particular implementation. The method 900 may begin at block 902.

In block 902 ("Collect Sensor Data Related To A Quality Of Health Of A Patient"), sensor data related to a quality of health of a patient may be collected. In some embodiments, the sensor data may be collected by the chronic burden module from the sensors. In these and other embodiments, the sensor data may be related to a physical or mental health of the patient. Alternatively or additionally, the sensor data may pertain to, include, and/or be indicative of at least one of a diet pattern, a sleep pattern, an exercise pattern, an activity level, heart rate, posture, stress, blood pressure variation, blood glucose, heart rhythm, smoking status, pain level, and/or GPS data of the patient. Block 902 may be followed by block 904.

In block 904 ("Collect Patient Data"), patient data may be collected. The patient data may indicate at least one of a biological profile of the patient, a psychological profile of the patient, a social profile of the patient, physician notes related to the biological profile of the patient, physician notes related to the psychological profile of the patient, a baseline of sensor based data, and physician notes related to the social profile of the patient. Block 904 may be followed by block 906.

In block 906 ("Receive Input From the Patient"), patient input may be received from the patient. Alternatively or additionally, block 906 may include receiving one or both of manual inputs from the patient and/or sensor outputs from one or more sensors collecting data from the patient. The patient input may provide a quantification of a present health risk assessment of the patient using minimum clicks in minimum categories using a VAS. In some embodiments, the VAS may be obtained by the patient indicating on an avatar a location of pain, an amount of pain, and/or a type of pain that the patient is experiencing. The avatar may include one or more of the avatars 611a-b, 613, and/or 615 discussed elsewhere herein. Block 906 may be followed by block 908.

In block 908 ("Receive Patient Input In Response To One Or More Questions Directed To A Quality Of Health Of The Patient") patient input in response to one or more questions directed to a quality of health of the patient may be received. In some embodiments, the patient input may be received in response to one or more questionnaires being provided to the patient by a questionnaire module such as the questionnaire module 104 of FIG. 1. In these and other embodiments, the patient input may be received in response to one or more questionnaires being provided to the patient by a disease calculator, such as the disease calculator 106 of FIG. 1. Block 908 may be followed by block 910.

In block 910 ("Generate A Chronic Care Burden (CCB) Score With A Pre-Defined Risk Stratification"), a CCB score with a pre-defined risk stratification may be generated. The CCB score with the pre-defined risk stratification may be generated based on at least two of the patient data, the sensor data, and the patient input. Block 910 may be followed by block 912.

In block 912 ("Generate A CCB Result"), a CCB result may be generated. The CCB result may include the CCB score and a risk stratification of the patient based on the pre-defined risk stratification and the CCB score. Block 912 may be followed by block 914.

In block 914 ("Provide The CCB Result To A Care Provider"), the CCB result may be provided to the care-provider. In some embodiments, the care-provider may include a physician of the patient. In some embodiments, the CCB result is provided to the care-provider only if the CCB result exceeds a CCB threshold amount and/or if the CCB result has deteriorated from a prior CCB result by an amount more than a CCB difference threshold. In other embodiments, the alert may be provided for each and every CCB result.

Figure 10:
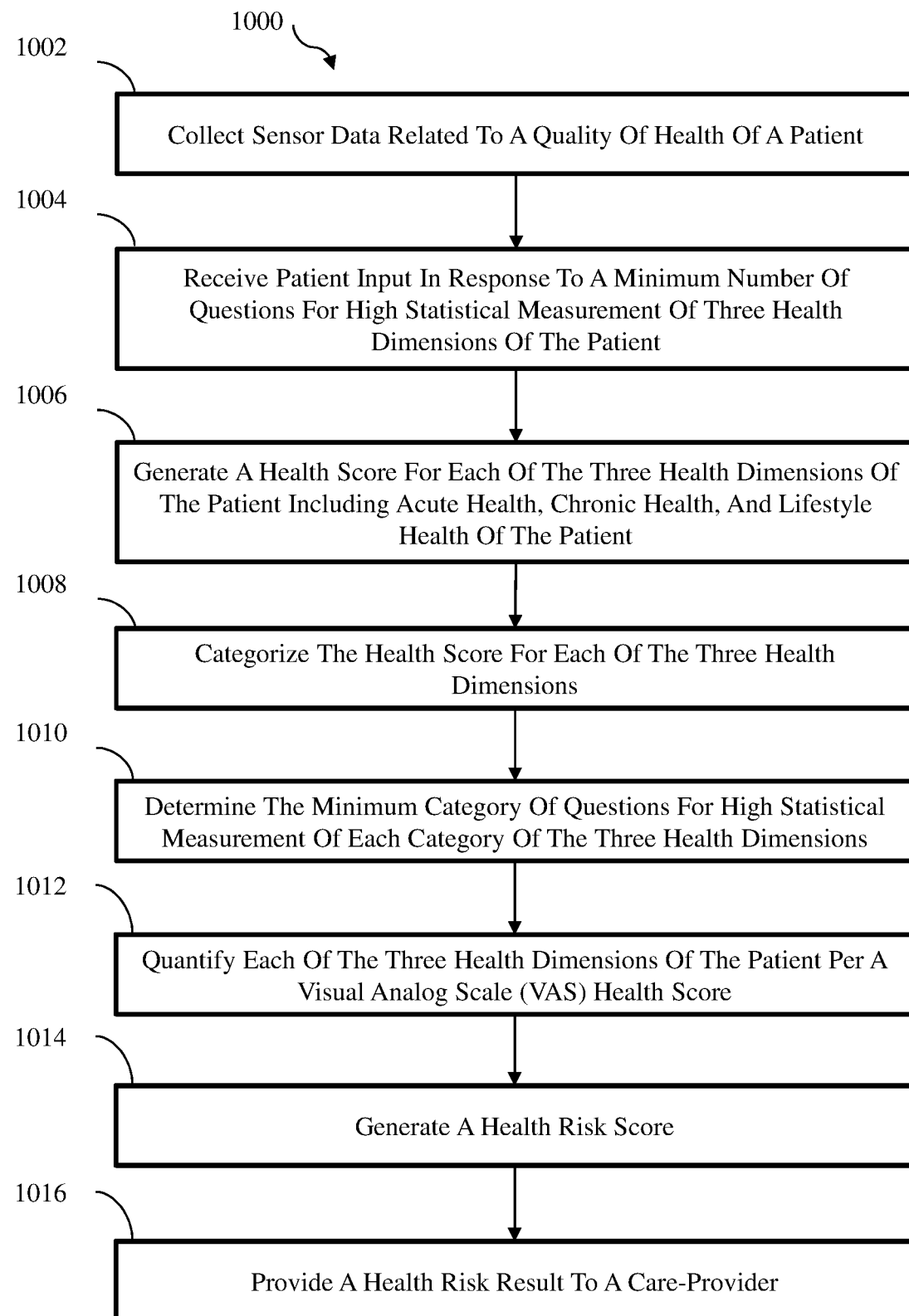
FIG. 10 is a flow diagram of an example method to generate a health risk score of a patient.

FIG. 10 is a flow diagram of an example method 1000 to generate a health risk score of a patient, arranged in accordance with at least one embodiment described herein. The method 1000 may be performed by a total health module such as the total health module 116 of FIG. 1. In some embodiments, the total health module may have access to a chronic disease database, such as the chronic disease database 126 of FIG. 1 and/or an EHR database such as the EHR database 128 of FIG. 1. Additionally, the total health module may have access to one or more sensors, such as the sensors 120 and 122 of FIG. 1.

The method 1000 may be performed, in whole or in part, by the total health module. Alternatively or additionally, the method 1000 may be implemented by a processor device that performs or controls performance of one or more of the operations of the method 1000. For instance, a computer (such as the computing device 1400 of FIG. 14) or other processor device may be communicatively coupled to the total health module and/or may be included as a control system of the total health module and may execute software or other computer-readable instructions accessible to the computer, e.g., stored on a non-transitory computer-readable medium accessible to the computer, to perform or control the total health module to perform the method 1000 of FIG. 10.

The method 1000 may include one or more of blocks 1002, 1004, 1006, 1008, 1010, 1012, 1014, and/or 1016.

Although illustrated as discrete blocks, various blocks may be divided into additional blocks, supplemented with additional blocks, combined into fewer blocks, or eliminated, depending on the particular implementation. The method 1000 may begin at block 1002.

In block 1002 ("Collect Sensor Data Related To A Quality Of Health Of A Patient"), sensor data related to a quality of health of a patient may be collected. In some embodiments, the sensor data may be collected by the total health module from the sensors. In these and other embodiments, the sensor data may pertain to, include, and/or indicate at least one of a diet pattern, a sleep pattern, an exercise pattern, an activity level, heart rate, posture, stress, blood pressure variation, blood glucose, heart rhythm, smoking status, pain level, and/or GPS data of the patient. Block 1002 may be followed by block 1004.

In block 1004 ("Receive Patient Input In Response To A Minimum Number Of Questions For High Statistical Measurement Of Three Health Dimensions Of The Patient"), patient input in response to a minimum number of questions for high statistical measurement of three health dimensions of the patient may be received. Block 1004 may be followed by block 1006.

In block 1006 ("Generate A Health Score For Each Of The Three Health Dimensions Of The Patient Including Acute Health, Chronic Health, and Lifestyle Health Of The Patient"), a health score for each of the three health dimensions of the patient including acute health, chronic health, and lifestyle health of the patient may be generated. The health score for a first health dimension may be based on an SHC score, the health score for a second health dimension may be based on a CCB score, and the health score for a third health dimension may be based on a LCC score. The SHC score may be the same or similar to the SHC score generated by the graded escalation module 110 of FIG. 1. The CCB score may be the same or similar to the CCB score generated by the chronic burden module 108 of FIG. 1. The LCC score may be the same or similar to the LCC score generated by the lifestyle choice module 114 of FIG. 1. Block 1006 may be followed by block 1008.

In block 1008 ("Categorize The Health Score For Each Of The Three Health Dimensions") the health score for each of the three health dimensions may be categorized. Block 1008 may be followed by block 1010.

In block 1010 ("Determine The Minimum Category Of Questions For High Statistical Measurement Of Each Category Of The Three Health Dimensions"), the minimum category of questions for high statistical measurement of each category of the three health dimensions may be determined. Block 1010 may be followed by block 1012.

In block 1012 ("Quantify Each Of The Three Health Dimensions Of The Patient Per A Visual Analog Scale (VAS) Health Score"), each of the three health dimensions of the patient per a VAS health score may be quantified. Block 1012 may be followed by block 1014.

In block 1014 ("Generate A Health Risk Score"), a health risk score may be generated. The health risk score may be based on the health score for each of the three health dimensions. The health risk score may be the same or similar to the health risk score discussed elsewhere herein. Block 1014 may be followed by block 1016.

In block 1016 ("Provide A Health Risk Result To A Care-Provider"), a health risk result may be provided to the care-provider. The health risk result may include the health risk score. In some embodiments, the care-provider may include a physician of the patient. In some embodiments, the health risk result is provided only if a trend of the health of the patient is improving (e.g., a second health risk result includes a higher score than a first health risk result). In other embodiments, the health risk result is provided only if a trend of the health of the patient is declining (e.g., the second health risk result includes a lower score than the first health risk result). In yet other embodiments, the alert may be provided for each and every comparison result.

Figure 11:
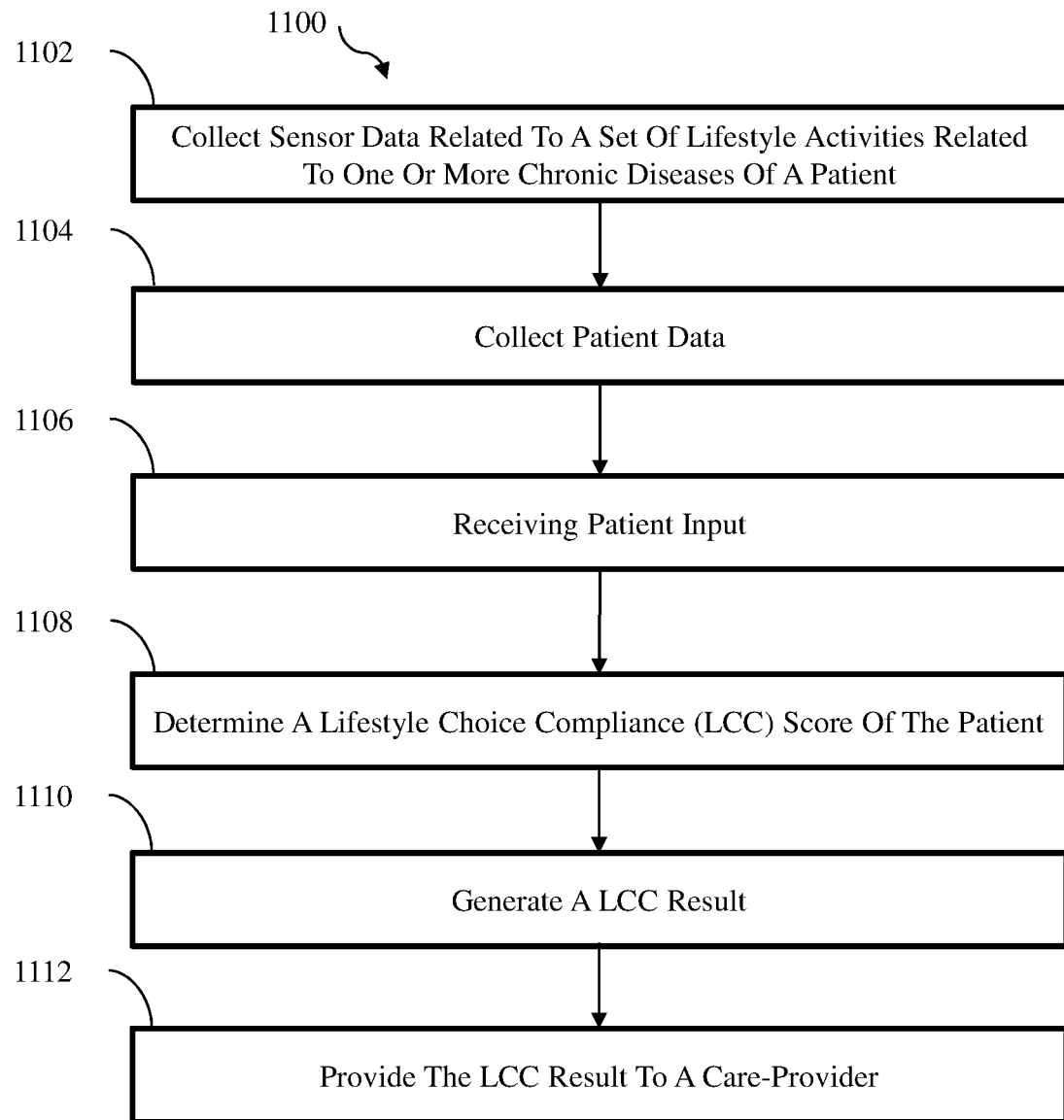
FIG. 11 is a flow diagram of an example method to evaluate and stratify a lifestyle health compliance of a patient.

FIG. 11 is a flow diagram of an example method 1100 to evaluate and stratify a lifestyle health compliance of a patient, arranged in accordance with at least one embodiment described herein. The method 1100 may be performed by a lifestyle choice module such as the lifestyle choice module 114 of FIG. 1. In some embodiments, the lifestyle choice module may have access to a chronic disease database, such as the chronic disease database 126 of FIG. 1 and/or an EHR database such as the EHR database 128 of FIG. 1. Additionally, the lifestyle choice module may have access to one or more sensors, such as the sensors 120 and 122 of FIG. 1.

The method 1100 may be performed, in whole or in part, by the lifestyle choice module. Alternatively or additionally, the method 1100 may be implemented by a processor device that performs or controls performance of one or more of the operations of the method 1100. For instance, a computer (such as the computing device 1400 of FIG. 14) or other processor device may be communicatively coupled to the lifestyle choice module and/or may be included as a control system of the lifestyle choice module and may execute software or other computer-readable instructions accessible to the computer, e.g., stored on a non-transitory computer-readable medium accessible to the computer, to perform or control the lifestyle choice module to perform the method 1100 of FIG. 11.

The method 1100 may include one or more of blocks 1102, 1104, 1106, 1108, 1110, and/or 1112. Although illustrated as discrete blocks, various blocks may be divided into additional blocks, supplemented with additional blocks, combined into fewer blocks, or eliminated, depending on the particular implementation. The method 1100 may begin at block 1102.

In block 1102 ("Collect Sensor Data Related To A Set Of Lifestyle Activities Related To One Or More Chronic Diseases Of A Patient"), sensor data related to a set of lifestyle activities related to one or more chronic diseases of a patient may be collected. In some embodiments, the sensor data may be collected by the lifestyle choice module from the sensors. In these and other embodiments, the sensor data may pertain to, include, and/or indicate at least one of a diet pattern, a sleep pattern, an activity level, heart rate, posture, stress, blood pressure variation, blood glucose, heart rhythm, smoking status, pain level, and/or GPS data of the patient. Block 1102 may be followed by block 1104.

In block 1104 ("Collect Patient Data"), patient data may be collected. The patient data may indicate at least one of a biological profile of the patient, a psychological profile of the patient, a social profile of the patient, and/or one or more lifestyle choice prescriptions of the patient. Block 1104 may be followed by block 1106.

In block 1106 ("Receive Patient Input"), patient input may be received from the patient. The patient input may indicate compliance of the patient with the lifestyle choice prescriptions. Block 1106 may be followed by block 1108.

In block 1108 ("Determine A Lifestyle Choice Compliance (LCC) Score Of The Patient") a LCC score may be determined. The LCC score may be based on at least one of the sensor data related to the set of lifestyle activities and the patient input that indicates compliance of the patient with the lifestyle choice prescriptions. Block 1108 may be followed by block 1110.

In block 1110 ("Generate A LCC Result") a LCC result may be generated. The LCC result may include the LCC score. Block 1110 may be followed by block 1112.

In block 1112 ("Provide The LCC Result To A Care Provider"), the LCC result may be provided to the care-provider. In some embodiments, the care-provider may include a physician of the patient. In some embodiments, the LCC result is provided to the care-provider only if the LCC score of the patient falls below a pre-specified limit. In other embodiments, the alert may be provided for each and every LCC result.

The data for Health Score can be collected from the patients enrolled in the care program or collected from public domain. It can be categorized in many ways with one embodiment being Gender, Age and State. For each category, distributions are created for general health, physical health, mental health and activity limitation. As an example of just one out of many similar useful embodiments, the following hazard ratios may be effective:

General Health:
Value: 1; Hazzard ratio: 1
Value: 2; Hazzard ratio: 12.3
Value: 3; Hazzard ratio: 21.0
Value: 4; Hazzard ratio: 44.5
Value: 5; Hazzard ratio: 110.4
Physical Health:
Value: 0; Hazzard ratio: 1
Value: 1 to 10; Hazzard ratio: 13.0
Value: 11 to 20; Hazzard ratio: 21.3
Value: 21 to 30; Hazzard ratio: 32.0
Mental Health:
Value: 0; Hazzard ratio: 1
Value: 1 to 10; Hazzard ratio: 12.3
Value: 11 to 20; Hazzard ratio: 19.7
Value: 21 to 30; Hazzard ratio: 23.6
Activity Limitation:
Value: 0; Hazzard ratio: 1
Value: 1 to 10; Hazzard ratio: 14.9
Value: 11 to 20; Hazzard ratio: 23.4
Value: 21 to 30; Hazzard ratio: 36.5

Now, the raw HRQoL score may be created by combining the percentile scores after weighting them suitably with the hazard ratios. As an example of just one, out of many, such useful embodiments, one can use the formulae:

HRQoL score=(General health percentile)*(1−general health hazard ratio/$K$)+(Physical health percentile)*(1−physical health hazard ratio/$K$)+(Mental health percentile)*(1−mental health hazard ratio/$K$)+(Activity limitation percentile)*(1−Activity limitation hazard ratio/$K$); where "$K$" can be derived using the normalized hazards from the General health category.

The normalized HRQoL score may be calculated in several ways with one embodiment being based on the range observed in the population analyzed. For example, one can use the following formulae:

Normalized HRQoL score=(HRQoL score−0.199897)/(3.752099−0.199897).

Now, using the Activity Score as computed in equation 1, a comprehensive health score (HICO) for the given patient can be calculated by suitably combining the normalized HRQoL score with the activity score. As an example of just one of our many similar useful embodiments, one can use the following formula:

HICO=0.5*Normalized HRQoL score+0.5*Activity Score.

It will be clear to a person skilled in the state of the art that an HRQoL score can also be calculated based on the statistical distribution of the sensor output values obtained from a representative sample where the sensor output values can represent either markers for physiological attributes such as heart rate, heart rhythm, blood pressure, blood glucose, weight, diet, chore related activity, exercise, smoking statistics, pollution encountered, etc. OR quality of life related attributes such as stress, mood, sleep duration, sleep quality, posture, social interaction, home bound time, leisure related activities, etc. The quantification of quality of life related attributes may be measured, for example, by the deviation of each such attribute from the representative sample and the physiological attributes may be measured by (preferably) deviation from the physician preferred values or the comparable population statistics. For example, the average blood pressure in the given sample may be 140/95 though the desired blood pressure, per the physician, may be 120/80, and the comparison can be made with respect to either of the reference values. Each such attribute pertaining to quality of life can then be combined based upon the percentile scores of that attribute. The weight of percentile value of each attribute can be assigned based on the preferred definition of HRQoL or may be chosen either by the care provider or by the patient or set a priori in consultation with the patient. For example, for a patient who is deemed by his care-provider as naturally introvert by choice, stress, mood, sleep can assume far greater weightage than a person who is deemed by his care provider as naturally extrovert by choice. For the person, naturally extrovert by choice, increase in social interactions or leisure related activities or reduction in home bound time will imply a greater improvement in quality of life. The HRQoL value obtained in this manner can be then weighted using the physiological attributes so that quality of life related attributes measurement can be normalized with respect to the health of the patient too. For example, when two patients have exactly equal attributes with respect to the quality of life but one of them maintains a better control on blood pressure, heart rate, and blood glucose then his HRQoL is deemed better.

In some embodiments, a physical predictive model of the physical health of a patient (herein 'physical predictive model') may be determined. The physical predictive model may be the same or similar to the health risk score. For example, the physical predictive model of the physical health of the patient may indicate an overall physical health of the patient. The physical predictive model may be determined by combining big data (e.g., CDC data) with patient data based on one or more of the following observations: a breakdown in health of a patient may be preceded by an acute episode which may occur when a disease burden is initially detected as a symptomatic occurrence; initial system-wide symptomatic disturbances of the patient may be tilted back to an original symptom-less homeostatic balance; and/or after experiencing moderate symptomatic changes, the patient is likely to experience increased tiredness and/or decreased resilience when experiencing symptoms, which may increase an amount of time for patient recovery post symptom which may take longer than patient recovery from activity pre symptom due to the onset of disease based reduced resilience.

In some embodiments, the physical predictive model may be determined daily for a period of time. In these and other embodiments, a day may include a period of time between a start node that relates to the patient waking up and an end node that relates to the patient falling asleep. Additionally, each day may include a number of states of the patient (e.g., ADL bins and/or activity bins). The period of time may include a week, a month, or any other appropriate period of time. In some embodiments, the resilience time may indicate how much time has elapsed between an activity (e.g., exercise) and biomarkers of the patient returning to normal. The physical predictive model may additionally include resilience time of similar activities.

In some embodiments, the patient recovery pre symptom and/or a tiredness level of the patient post symptom may be determined using sensors (e.g., smartphones, wearable, and/or non-wearable sensors). If either the patient recovery from activity pre symptom and/or the tiredness level of the patient post symptom decreases, a similar decrease in the overall physical health of the patient may occur.

The physical predictive model may be determined based on the comparison of the big data with patient data based on the observations listed above. In some embodiments, a hidden Markov model may be used to determine the physical predictive model. The physical predictive model may be generated using one or more nodes that represent different states of the patient and edges which connect such nodes. The edges refer to a moving average of previous instances of patient resilience during periods of time.

In some embodiments, a day may include a series of states (e.g., nodes) of the patient. The states may correspond to the current day and the current health of the patient. For example, a node may correspond to the patient being healthy on a first day of the period of time. Additionally, the states of the patient may correspond to specific diseases, specific habits, and/or specific risks of the patient. Furthermore, the states of the patient may correspond to specific diseases, specific habits, and/or specific risks mapped to different weather types, seasons of the year, days of the week. For example, a third state of the patient may correspond to a heat stroke state of the patient on the first day in which an average temperature for the day is above eighty five degrees Fahrenheit.

In some embodiments, the states of the patient may be based on portions of data included in the EHR data, such as BMI, blood pressure control, smoking status, depression status, or any other appropriate data point of the patient. Additionally, the states of the patient may be based on insurance data, for example, Medicare data, related to risk scores of the patient and/or expenses incurred due to chronic diseases of the patient. Additionally, the states of the patient may be based on data included in the patient HRQOL input received from the patient. For example, the states of the patient may be based on the number of healthy days versus the number of unhealthy days physically and/or mentally that the patient reports experiencing.

The states of the patient may represent numerical values for a day according to one or more metrics. For example, the metrics may include an average activity level in a day, an average tiredness level in a day, or any other appropriate metric of the patient. The states of the patient may be weighted based on both a physical aspect and an autonomous resiliency aspect of the patient. In some embodiments, the states of the patient to be considered in determining the physical predictive model may be determined by combining the short term health score, the chronic care burden score, and/or the lifestyle choice score.

A probability of the patient being in a particular state (e.g., $P(\pi_t)$) may be determined using evidence nodes. The evidence nodes may be based on a level of compliance of the patient with one or more goals and/or schedule for the patient on a day. For example, a first evidence node may be based on compliance of the patient with a specific goal on the first day and a second evidence node may be based on compliance of the patient with a specific schedule on a second day. In some embodiments, the evidence nodes may be associated with a total activity level, a total sedentary time, a total sleep, a blood pressure, a blood glucose, a pulmonary, and/or a pain level of the patient.

Each evidence node may include values from the different states of the patient with a corresponding probability. For example, an evidence node may include values from a healthy node (e.g., a healthy state of the patient) with probability $P_H$ and from an unhealthy node with probability $P_U$. In some embodiments, the value of the evidence nodes may also represent the resiliency, an exercise schedule, and/or deviation from the schedule of the patient. Thus, different evidence nodes may include different distributions from which values of the evidence nodes are sampled. The evidence node values may be used to determine the probability of the patient transitioning from one state to another state. For example, the probability of the patient transitioning from a healthy state to an unhealthy state.

The value of each evidence node may include a distribution specific to the patient. The distribution specific to the patient may be determined based on an initial physical training set of data. Additionally, the distribution specific to the patient may be extrapolated to similar patients with similar body build and/or types. In some embodiments, the distribution specific to the patient may be determined using empirical evidence, which may indicate a physical baseline of the patient for each evidence node (e.g., observed deviations from an expected mean of an evidence node for each state). For example, the resilience time may be compared to a resilience baseline of the patient. The comparison may be used to predict how the activity level of the patient deviated from the expected ADLs and/or activity bins and/or to predict what the physical health of the patient is on a day.

In some embodiments, the physical training set of data may include data related to each numerical combination of physical health scores of the patient. For example, the training set of data may include data related to all possible scores for combining the short term health score, the lifestyle choice score, and/or the chronic burden score of the patient. A distribution of sensor data may be determined for specific values of the short term health score, the lifestyle choice score, and/or the chronic burden score, which may permit the physical predictive model to be determined.

In some embodiments, an expected number of evidence nodes may be determined per day and/or per period of time. The evidence node values may represent the level of compliance with the one or more goals and/or the schedule. For example, an evidence node may include a score of one for complete compliance and a score of zero for no compliance with the goals and/or the schedule. An evidence node may include a score between zero and one hundred for varying levels of compliance with the goals and/or schedule. In some embodiments, the value of each evidence node may be weighted based on a statistical significance of the corresponding evidence node.

A range of values for the evidence nodes may be assigned with a probability based on the physical baseline of the patient. For example, an event in which the heart rate of the patient takes three to four minutes to return to resting rate may be labelled as event A and an event in which the heart rate of the patient takes four to five minutes to return to resting rate may be labelled as event B. Empirically determined probabilities for event A and event B may be determined and assigned.

At the end of each day, resiliency levels of the patient and/or deviation from the expected number of evidence nodes may be determined. Additionally, the physical predictive model of the physical health of the patient may be determined using percentile based computation in which a mean-centered binomial distribution of population based metrics are centered at a score of fifty and scores associated with healthy patients are distributed towards one hundred.

A probability of the patient transitioning from a current state (e.g., $\pi_t$) on one day to another state (e.g., $\pi_{t'}$) on a subsequent day may be determined (e.g., $P(\pi_t|\pi_{t'})$). A probability of the patient being in one state may be determined using Equation 2.

$$P(\pi_t|E_{day1}, E_{day2}, \ldots, E_{dayn})) \qquad \text{Equation 2}$$

In Equation 2, $E_{day1}$ through $E_{dayn}$ may represent the evidence nodes for each day of the period of time. $E_{dayn}$ may correspond to a final day in the period of time. For example, in an embodiment in which the period of time is one week, $E_{dayn}$ may be $E_{day7}$. As another example, in an embodiment in which the period of time is one week, $E_{day4}$ may represent the evidence node associated with Thursday since Thursday is the fourth day of a week. Additionally, each state of the patient may only be associated with one output evidence node. For example, a state corresponding to a specific state of the patient on Thursday (e.g., day4) may be associated with a single evidence node that corresponds to $E_{day4}$.

In an example in which the patient may be in one of two states (e.g., a healthy state or a sick state) on a day, the probability of the patient being in the sick state may be determined using conditional probability. The probability of the patient being in a sick state given N evidence nodes may be determined according to Equation 3.

$$P(\pi_t = \text{Sick}|E_{Day1}, E_{Day2}, \ldots, E_{DayN}) = [P_S * (\Pi^n_{i=1} P \\ (E_{Day(i)}|E_{Day(i-1)}, E_{Day(i-2)}, \ldots, E_{Day1}, \text{Sick}))]/P \\ (E_{Day1}, \ldots, E_{DayN}) = [P_S * (\Pi^n_{i=1} P(E_{Day(i)}| \\ E_{Day(i+1)}, E_{Day(i+2)}, \ldots, E_{DayN}, \text{Sick}))]/ \\ P(E_{Day1}, \ldots, E_{DayN}) \qquad \text{Equation 3}$$

In Equation 3, $P_S$ may represent the probability that the patient is in the sick state.

In another example in which the patient may be in one of three states (e.g., the healthy state, an intermediate state, or the sick state) on a day, the probability of the patient being in one of the three states given N evidence nodes may initially be determined according to Equation 2. The probability of the patient being in one of the three states may be marginalized over all three states, since the evidence nodes may include conditional independence according to Equation 4:

$$E_{Day\ i} \perp \{\pi_x : x \neq i\} \qquad \text{Equation 4}$$

In Equation 4, x may represent day number in a series of days. The significance level of the current state may be determined recursively using Equations 5, 6, and 7.

$$\alpha_t(\pi_t) = P(\pi_t, E_{day\ 1:t}) = \Sigma_{\pi_{t-1}} P(\pi_t, \pi_{t-1}, E_{day\ 1:t}) \qquad \text{Equation 5}$$

$$\alpha_t(\pi_t) = P(E_{day\ t}|\pi_t)\Sigma \pi_{t-1} P(E_{Day\ t}|\pi_t, \pi_{t-1}, E_{day\ 1:t-1})P \\ (\pi_t|\pi_{t-1}, E_{day\ 1:t-1})P(\pi_{t-1}, E_{day\ 1:t-1}) \qquad \text{Equation 6}$$

$$\alpha_t(\pi_t) = P(E_{day\ t}|\pi_t)\Sigma_{\pi_{t-1}} P(\pi_t|\pi_{t-1})\alpha_{t-1}(\pi_{t-1}) \qquad \text{Equation 7}$$

$P(E_{day\ t}|\pi_t)$ and $P(\pi_t|\pi_{t-1})$ may be given as transition probabilities in the physical predictive model. Based on Equations 5, 6, and 7, the probability of the patient being in the current state on a day given the evidence node values may be determined according to Equation 8.

$$P(\pi_t | E_{day\ 1:t}) = \frac{\alpha_t(\pi_t)}{\sum_{i \in \Omega} \alpha_i(\pi_i)} \qquad \text{Equation 8}$$

In Equation 8, $\Omega$ may represent a set of states the patient may be in on the day.

An example program in which the probability of the patient being healthy or sick, given the evidence nodes over that last N days; the distribution of the states of the patient; the probability of transitioning between each state; the physical baselines of the patient; and a model setup may include:

```
function calculate_current_state(n_observations, day):
    markov_model = new Model(transition_probabilities, distribution_per_node)
    possible_states = markov_model.get_possible_states(day)
    today_observation = getTodaysData( )
    state_probabilities = [ ]
    for state in possible_states:
        prob=markov_model.get_probability_of_state(today_observation,n_observations)
        state_probabilities += [(state, prob)]
    return (argmax(state_probabilities), state_probabilities)
```

In the example program, the function get_probability_of_state( ) may determine $(P\pi_t|E_{Day1}, E_{Day2}, \ldots, E_{DayN})$ for each possible state of the patient. Additionally, the function get_probability_of_state( ) may return a tuple of the most likely state using distribution over all states.

In some embodiments, a metric of vitality may be determined using a moving average of the total activity and the tiredness levels of the patient. For example, K evidence nodes may represent a tuple of high or moderate activity in a day and the tiredness level of the patient. The values of the K evidence nodes may be adjusted based on a sequence of activities. For example, the value associated with the tiredness level (e.g., how tired the patient should be at the end of the day) may be adjusted by an amount if that day includes a high intensity activity (Activity1) followed by a moderate intensity activity (Activity2). As another example, the value associated with the tiredness level may be adjusted by another amount if that day includes the high intensity activity (Activity1) followed by another high intensity activity (Activity3).

In some embodiments, the resilience time between activities (e.g., the period of time of rest between Activity1 and Activity2 or Activity3) may be weighted differently depending on the sequence of activities. For example, if the sequence of activities is Activity1 followed by Activity3 (e.g., two high intensity activities), the period of time may be assigned a fifty percent higher weight than if the sequence of activities is Activity1 followed by Activity2. Furthermore, any activity or evidence node in a day may be adjusted based on the sequence of the activities, which may increase accuracy of the physical predictive model of the physical health of the patient.

In some embodiments, the probabilities associated with each state and/or the value of the evidence nodes may be adjusted based on weather, seasons, month, or any other appropriate piece of data for the period of time. If the current day has different weather than a previous similar day, the expected activity level may be adjusted accordingly. For example, if the current day has colder weather than the previous similar day, the patient may remain indoors more on the current day. ADLs and/or activity bins that are associated with outdoor activities may be assigned a lower weight or no weight at all. Additionally, ADLs and/or activity bins that are associated with indoor activities may be assigned a greater weight. As another example, a probability of transitioning to a node associated with a heart attack may increase during winter months and/or heat stroke and dehydrations may increase during summer months.

An example program in which the sequence of activities in a day are received and generates a tuple of activity and state for a day may include:

```
def calculate_mood(activities_list, day):
    expected_array = get_baseline( )
    actual_array = get_today_readings( )
    output_lst = [ ]
    for i in range(len(activities_list):
        x = expected_array[day][i]
        y = actual_array[day][i]
        output_lst += [(activities_lst[i], x-y)]
    return output_lst
```

In some embodiments, the physical predictive model may be determined as a tuple of different components that are not added together. For example, the physical predictive model may be equal to {SHC, CCB, LCC}, in which SHC represents the short term health score, CCB represents the chronic burden score, and LCC represents the lifestyle choice score.

In some embodiments, the physical predictive model may be determined as a weighted average of the three health dimensions. For example, the weighted average of the short term health score, the chronic burden score, and the lifestyle choice score. Furthermore, the physical predictive model may be determined according to Equation 9.

$$HS=f(SHC,CCB,LCC) \qquad \text{Equation 9}$$

In Equation 9, HS represents the health risk score, SHC represents the short term health score, CCB represents the chronic burden score, and LCC represents the lifestyle choice score. The quantification may be based on statistical distribution of the physical predictive model and of the big data with respect to the chronic burden score and/or the lifestyle choice score of the patient. Additionally, quantification may be based on statistical distribution of the physical predictive model over a baseline period for the short term health score.

The weighted average of the three health dimensions may be determined based on the EHR data, big data, or any other appropriate data. In some embodiments, the weighted average of the three health dimensions may be assigned by the physician of the patient. The weighted average of the three health dimensions may incorporate a mean and a standard deviation of the short term health score, the chronic burden score, and/or the lifestyle choice score. The distribution of the sum of the short term health score, the chronic burden score, and the lifestyle choice score may be determined according to Equation 10.

$$V \sim N(\mu_x + \mu_y + \mu_z, \sigma_x^2 + \sigma_y^2 + \sigma_z^2 +) \qquad \text{Equation 10}$$

In Equation 10, X represents the short term health score, Y represents the chronic burden score, Z represents the lifestyle choice score, $\mu_x$ represents the mean and median of the short term health score, $\mu_y$ represents the mean and median of the chronic burden score, $\mu_z$ represents the mean and median of the lifestyle choice score, $\sigma_x$ represents the standard deviation of the short term health score, $\sigma_y$ represents that standard deviation of the chronic burden score, and $\sigma_z$ represents the standard deviation of the lifestyle choice score. Additionally, the weighted average of the three health dimensions may be the same or similar. In some embodiments, the physical predictive model and the risk of disease ρ may be determined by examining the deviation from the expected value.

In some embodiments, the physical predictive model may be determined by convolving Equation 11.

$$V=\alpha X+\beta Y+\gamma Z \qquad \text{Equation 11}$$

In Equation 11, α represents the weight assigned to the short term health score, β represents the weight assigned to the chronic burden score, and γ represents the weight assigned to the lifestyle choice score. In some embodiments, the physical predictive model determined by convolving Equation 11 may be determined per chronic diseases. Thus the physical predictive model of the patient experiencing multiple chronic diseases may be determined according to Equation 12.

$$HS_i=f(SHC,CCB_i,LCC) \qquad \text{Equation 12}$$

In Equation 12, $CCB_i$ may represent the chronic burden score for a single chronic disease of the multiple chronic diseases that the patient is experiencing. Additionally, the physical predictive model may be determined according to Equation 13.

$$HS=\{HS_1, \ldots, HS_k\} \qquad \text{Equation 13}$$

In Equation 13, each physical predictive model (e.g., $HS_1$ through $HS_k$) may be either a composite health score or a triplet score of the short term health score, the chronic burden score, and the lifestyle choice score for each chronic disease the patient is experiencing.

In some embodiments, the physical predictive model may be used to incorporate the short term health score, the chronic burden score, and the lifestyle choice score so as to incorporate evidence nodes representing the health score of the patient using patient HRQOL input, patient GSRH input, patient HALEX input, chronic burden score, and/or lifestyle choice score values.

In some embodiments, a particular day in the period of time may be compared to a similar day in another period of time. For example, if the period of time is a week, Mondays in the various weeks may be compared to each other to determine whether the activity of a current Monday is different from the activity level of the similar Monday in a previous period of time.

In some embodiments, a predictive model of the mental health of the patient (herein 'mental predictive model') may be determined. The mental predictive model may be used to detect whether the patient is suffering from heightened anxiety, a troubling down mental state, clinical depression, or any other neurological state. The mental predictive model may be determined by combining big data (e.g., CDC data) with patient data based on the following observation: a patient in poor mental health (e.g., depressed) on a day is more likely to be in poor mental health on a subsequent day as well. In some embodiments, the mental predictive model may be determined daily for the period of time.

In some embodiments, the mental predictive model may determine relationships between changes in biomarkers of the patient and the mental state of the patient and/or changes in biomarkers compared to a mental baseline of the patient. Additionally, the mental predictive model may determine deviation from the sensor data and/or deviation from a template of the patient for a day. The mental predictive model may be determined using a current mental state of the patient. The mental predictive model may be based at least in part on the sensor data. The sensor data may be gathered by a smartphone, biosensors, various smartphone applications, and/or facial action coding systems (FACS).

In some embodiments, the current mental state of the patient may be determined based on how the patient is interacting with the smartphone. For example, the smartphone may detect a speed at which the patient types, how the backspace or other special symbol buttons are pressed, how much the smartphone shakes during use. Additionally, the current state of the patient may be determined based on the heart rate, a heart rate variance, responses from an electro dermal analysis (EDA), and/or any other appropriate biomarker of the patient.

In some embodiments, the current mental state of the patient may be determined based on patient input received via a smartphone application. A smartphone application, such as the Circumplex App, may include a user interface with multiple locations representing different mental states. For example, the user interface may include locations representing pleasant activation, activated pleasure, pleasure, deactivated pleasure, pleasant deactivation, deactivation, unpleasant deactivation, deactivated displeasure, displeasure, activated displeasure, unpleasant activation, and/or activation mental states of the patient. Furthermore, the current mental state of the patient may be determined based on emotion recognition using FACS that allows no frame to frame recording of activity and/or life of the patient besides emotions and the activity type. For example, a FACS may be programmed to recognize facial expressions of the patient that are associated with different mental states of the patient.

In some embodiments, the mental states of the patient may be associated with portions of data included in the EHR data, such as BMI, blood pressure control, smoking status, depression status, or any other appropriate data point of the patient. Additionally, the mental states of the patient may be based on insurance data, for example, Medicare data, related to risk scores of the patient and/or expenses incurred due to chronic diseases of the patient. Additionally, the mentally states of the patient may be based on data included in the patient HRQOL input. For example, the mental states of the patient may be based on the number of healthy days versus the number of unhealthy days physically and/or mentally that the patient reports experiencing.

The mental states of the patient may represent the day, a mood of the patient, an expected biomarker, and/or an external marker. The external marker may include states of the weather (e.g., one node may correspond to Mondays where the patient is in a Sad mental state and the weather is rainy). Moods of the patient may include happy, excited, calm, normal, sad, distressed, and/or any other appropriate mood. A value of the mental states may be a weighted average of deviations from the mental baseline of the patient. Each deviation range may be determined based on a specific probability. The mental states of the patient may represent mood scores for a day.

A probability of the patient being in a particular mental state (e.g., P(it)) may be determined using mental evidence nodes. The mental evidence nodes may be based on a level of compliance of the patient with one or more goals and/or schedule for the patient on a day. In some embodiments, the mental evidence nodes may be based on the sensor data gathered by the smartphone, biosensors, various smartphone applications, and/or a FACS. Additionally, the evidence nodes may be based on a deviation from a mean on a day. Alternatively, the mental evidence nodes may be based on the level of compliance of the patient with one or more goals and/or schedule for the patient during an activity. In some embodiments, the mental evidence nodes may be associated with the total activity level, the total sedentary time, the total sleep, the blood pressure, the blood glucose, the pulmonary, and/or the pain level of the patient.

Each mental evidence node may include values from the different mental states of the patient with a corresponding probability. For example, a mental evidence node may include values from a happy node (e.g., a happy mental state of the patient) with probability $P_H$ and from a sad node with probability $P_S$. Thus, different mental evidence nodes may include different distributions from which the mental evidence node values are sampled. The mental evidence node values may be used to determine the probability of the patient transitioning from one mental state to another mental state. For example, the probability of the patient transitioning from a happy mental state to a sad mental state.

The value of each mental evidence node may include a distribution specific to the patient. The distribution specific to the patient may be determined based on an initial mental training set of data. Additionally, the distribution specific to the patient may be extrapolated to similar patients with similar mental compositions and/or types. In some embodiments, the distribution specific to the patient may be determined using empirical evidence, which may indicate a mental baseline of the patient for each mental evidence node (e.g., observed deviations from an expected mean of an evidence node for each state). The comparison may be used to predict how the activity level of the patient deviates from the expected ADLs and/or activity bins and/or to predict what the mental health of the patient is on a day.

In some embodiments, an expected number of mental evidence nodes may be determined for each day. The mental evidence nodes may include a value that represents the level of compliance with the one or more goals and/or the schedule. For example, a mental evidence node may include a score of one for complete compliance and a score of zero for no compliance with the goals and/or the schedule. A mental evidence node may include a score between zero and one for varying levels of compliance with the goals and/or the schedule. In some embodiments, the value of each mental evidence node may be weighted based on a statistical significance of the mental evidence node.

A range of values for the mental evidence nodes may be assigned with a probability based on the mental baseline of the patient. For example, empirically determined probabilities for event A and event B may be determined and assigned. The probability of the range of values may be determined by dividing a number of times an event occurs by a total number of times events occur.

Activity levels of the patient may be determined each day during the period of time. Likewise, the mental state of the patient may be determined each day. Furthermore, activity levels and/or mental state of the patient may be determined during each activity.

A probability of the patient transitioning from a current mental state (e.g., $\pi_t$) on one day to another mental state (e.g., $\pi_{t'}$) on a subsequent day may be determined (e.g., $P(\pi_t | \pi_{t'})$. A probability of the patient being in one mental state may be determined using Equation 14.

$$P(\pi_t | E_{day1}, E_{day2}, \ldots, E_{dayn}))$$

Equation 14

In Equation 14, $E_{day1}$ through $E_{dayn}$ may represent the mental evidence nodes for each day of the period of time.

In an example in which the patient may be in one of two states (e.g., a happy mental state or a sad mental state) on a day, the probability of the patient being in the sad mental state may be determined using conditional probability. The probability of the patient being in the sad mental state given N evidence nodes may be determined according to Equation 15.

$$P(\pi_t = Sad | E_{Day1}, E_{Day2}, \ldots, E_{DayN}) = [P_S^* (\Pi_{i=1}^n P(E_{Day(i)} | E_{Day(i-1)}, E_{Day(i-2)}, \ldots, E_{Day1}, \text{Sick}))]/P(E_{Day1}, \ldots, E_{DayN}) = [P_S^* (\Pi_{i=1}^n P(E_{Day(i)} E_{Day(i+1)}, E_{Day(i+2)}, \ldots, E_{DayN}, \text{Sick}))]/P(E_{Day1}, \ldots, E_{DayN})$$

Equation 15

In Equation 15, $P_S$ may represent the probability that the patient is in the sad mental state.

In another example in which the patient may be in one of three mental states (e.g., the happy mental state, an intermediate mental state, or the sad mental state) on a day, the probability of the patient being in one of the three mental states given N mental evidence nodes may initially be determined according to Equation 14. The probability of the patient being in one of the three mental states may be marginalized over all three mental states, since the mental evidence nodes may include conditional independence according to Equation 3. The significance level of the current mental state may be determined recursively using Equations 4, 5, and 6. Based on Equations 4, 5, and 6, the probability of the patient being in the current mental state on a day given the mental evidence node values may be determined according to Equation 7.

An example program in which the probability of the patient being happy or sad, given the mental evidence nodes over that last N days; the distribution of the mental states of the patient; the probability of transitioning between each mental state; the mental baseline of the patient; and a model setup may include:

```
function calculate_current_state(n_observations, day):
markov_model = new Model(transition_probabilities, distribution_per_node)
possible_states = markov_model.get_possible_states(day)
today_observation = getTodaysData( )
state_probabilities = [ ]
for state in possible_states:
    prob=markov_model.get_probability_of_state(today_observation,n_observations)
    state_probabilities += [(state, prob)]
return (argmax(state_probabilities), state_probabilities)
```

In the example program, the function get_probability_of_state( ) may determine $(P\pi_t | E_{Day1}, E_{Day2}, \ldots, E_{DayN})$ for each possible mental state of the patient. Additionally, the function get_probability_of_state( ) may return a tuple of the most likely state using distribution over all mental states.

In some embodiments, a metric of emotion may be determined by creating mood tuples (e.g., (mood, activity)) for each activity in a day and by using mental evidence nodes for each activity rather than each day. The patient may receive feedback on the prediction of the mood of the patient after performing the activity.

In some embodiments, the probabilities associated with each mental state and/or the value of the mental evidence nodes may be adjusted based on weather, seasons, month, or any other appropriate piece of data for the period of time.

For example, if a current mental state of the patient is depressed, the probability of the mental state of the patient being depressed may increase. Thus, the probability of the patient transitioning from a depressed mental state on one day to a depressed mental state on a subsequent day may be increased.

In some embodiments, a predicted distribution of the sensor data may be determined based on a single mental state of the patient and the mental training set of data. For example, the single mental state may include: Monday, Raining, Mood=5.0/10.0. The predicted distribution of the sensor data may be determined to correspond to the single node with specific probabilities.

In some embodiments, the mental state of the patient may be determined based on the day and the activity only. The day and the activity may be sufficient to determine the mental state if the patient typically follows a regimented schedule, is not clinically depressed, and does not suffer from other neurological disorders. A deviation from the mean of the expected activity of the patient may be used to determine the mental state. Determining the mental state based on the day and the activity only may provide data indicating an impact an activity may have on the mental state of the patient.

An example program in which the sequence of activities in a day are received and generates a tuple of activity and state for a day may include:

```
def calculate_mood(activities_list, day):
    expected_array = get_baseline( )
    actual_array = get_today_readings( )
    output_lst = [ ]
    for i in range(len(activities_list)):
        x = expected_array[day][i]
        y = actual_array[day][i]
        output_lst += [(activities_lst[i], x-y)]
    return output_lst
```

In some embodiments, the mental predictive model may be determined as a tuple of different components that are not added together. For example, the mental predictive model may be equal to (SHC, CCB, LCC, SMC), in which SHC represents the short term health score, CCB represents the chronic burden score, LCC represents the lifestyle choice score, and SMC represents the short term mood change.

Figure 12:
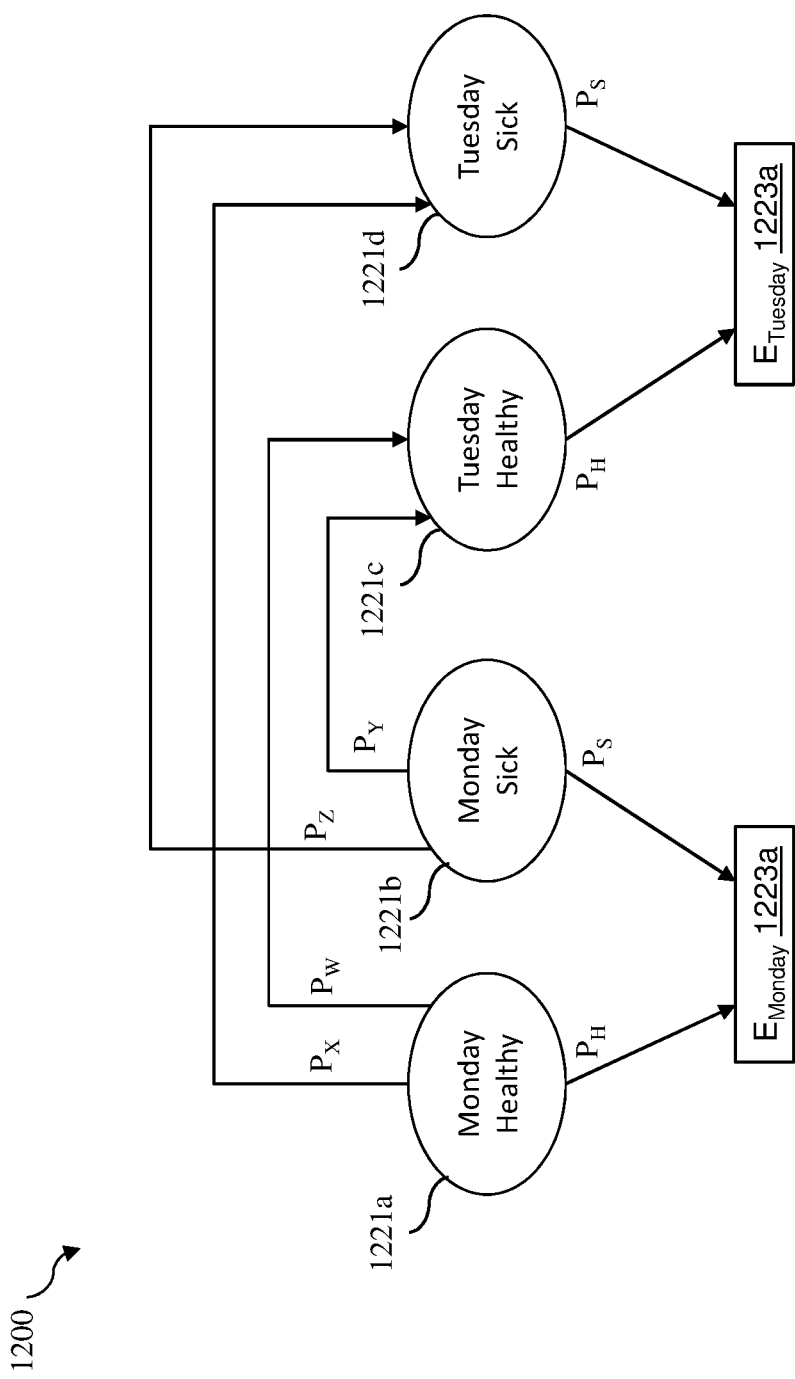
FIG. 12 is a block diagram illustrating a physical predictive model of the physical health of a patient in which the patient may be in one of two states.

FIG. 12 is a block diagram illustrating a physical predictive model 1200 of the physical health of a patient in which the patient may be in one of two states. The physical predictive model 1200 may include a first state 1221*a* of the patient, a second state 1221*b* of the patient, a third state 1221*c* of the patient, and a fourth state 1221*d* of the patient (collectively referred to herein as the states 1221). The physical predictive model 1200 may also include a first evidence node 1223*a* and a second evidence node 1223*b* (collectively referred to herein as the evidence nodes 1223 or evidence node 1223). The physical predictive model 1200 may be generated as discussed elsewhere herein.

As illustrated in FIG. 12, the first evidence node 1223a may correspond to a Monday during a period of time (e.g., a first day). Likewise, the second evidence node 1223b may correspond to a Tuesday during the period of time (e.g., a second day). It is understood that the evidence nodes 1223 may correspond to different days in the period of time. The evidence nodes 1223 may be based on a level of compliance of the patient with one or more goals and/or schedule for the patient on a day as discussed elsewhere.

As illustrated in FIG. 12, the first state 1221a may correspond to the patient being in a healthy state on the first day. Additionally, as illustrated in FIG. 12, the second state 1221b may correspond to the patient being in a sick state on the first day. Also, as illustrated in FIG. 12, the third state 1221c may correspond to the patient being in a healthy state on the second day. Furthermore, as illustrated in FIG. 12, the fourth state 1221d may correspond to the patient being in a sick state on the second day. It is to be understood that the states 1221 may correspond to different physical states of the patient.

A probability of the patient being in each of the states 1221 may be determined using Equation 2. The probability of the patient being in one of the states 1221 are represented as $P_H$ and $P_S$ in FIG. 12. $P_H$ may represent the probability of the patient being in the healthy state and $P_S$ may represent the probability of the patient being the sick state. For example, $P_H$ may represent the probability of the patient being in the first state 1221a on the first day and/or the third state 1221c on the second day. As another example, $P_S$ may represent the probability of the patient being in the second state 1221b on the first day and/or the fourth state 1221d on the second day.

A probability of the patient transitioning from one state 1221 on the first day to another state 1221 on the second day may be determined as discussed elsewhere. The probability of the patient transitioning from one state 1221 on the first day to another state 1221 on the second day are represented as $P_W$, $P_X$, $P_Y$, and $P_Z$ in FIG. 12. For example, $P_W$ may represent the probability of the patient transitioning from the first state 1221a on the first day to the third state 1221c on the second day. As another example, $P_X$ may represent the probability of the patient transitioning from the first state 1221a on the first day to the fourth state 1221d on the second day. As yet another example, $P_Y$ may represent the probability of the patient transitioning from the second state 1221b on the first day to the third state 1221c on the second day. For example, $P_Z$ may represent the probability of the patient transitioning from the second state 1221b on the first day to the fourth state 1221d on the second day.

Figure 13:
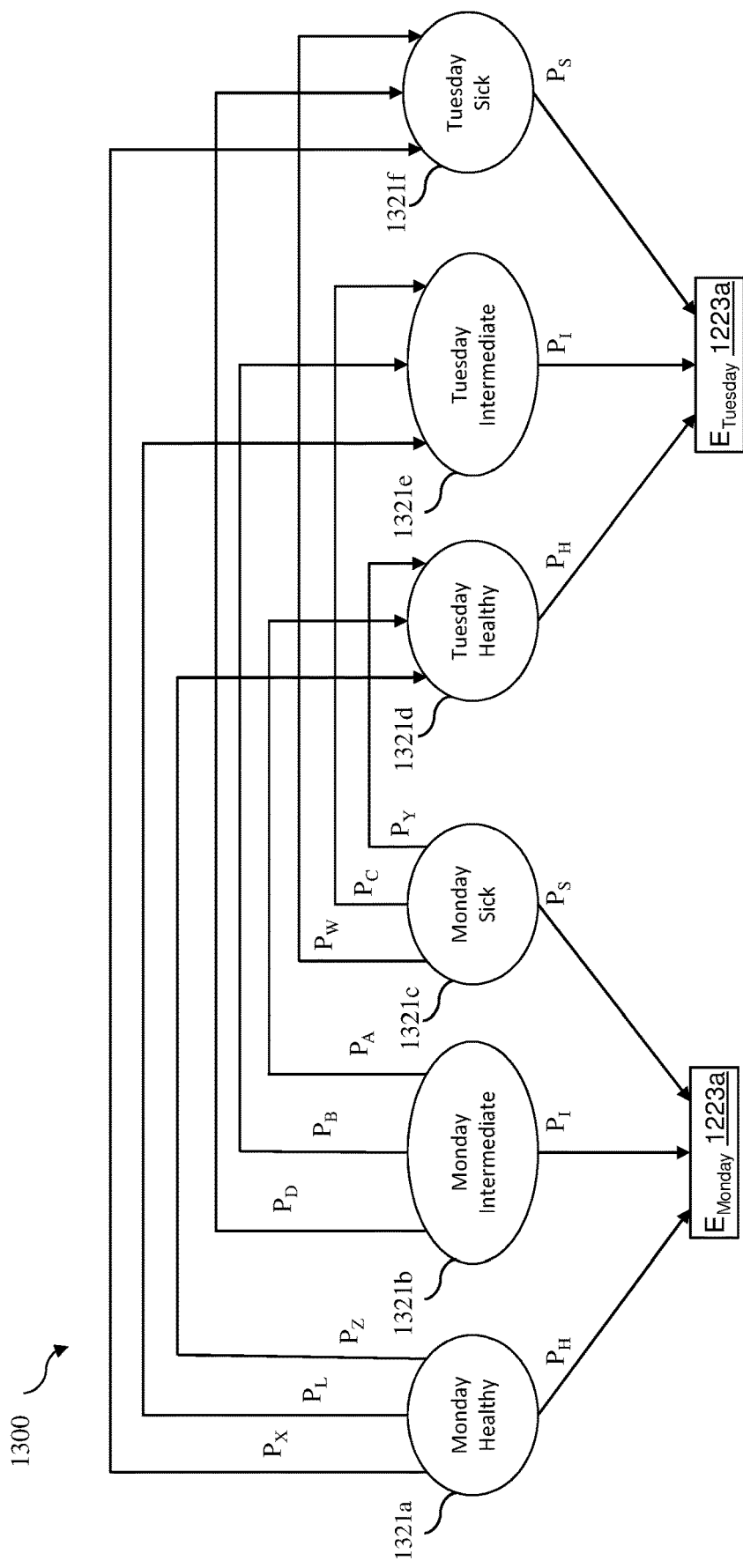
FIG. 13 is another block diagram illustrating a physical predictive model of the physical health of a patient in which the patient may be in one of three states.

FIG. 13 is another block diagram of a physical predictive model 1300 of the physical health of a patient in which the patient may be in one of three states. The physical predictive model 1300 may include a first state 1321a of the patient, a second state 1321b of the patient, a third state 1321c of the patient, a fourth state 1321d of the patient, a fifth state 1321e of the patient, and a sixth state 1321f of the patient (collectively referred to herein as the states 1321). The physical predictive model 1300 may also include a first evidence node 1323a and a second evidence node 1323b (collectively referred to herein as the evidence nodes 1323 or evidence node 1323). The physical predictive model 1300 may be generated as discussed elsewhere herein.

As illustrated in FIG. 13, the first evidence node 1323a may correspond to a Monday during a period of time (e.g., a first day). Likewise, the second evidence node 1323b may correspond to a Tuesday during the period of time (e.g., a second day). It is understood that the evidence nodes 1323 may correspond to different days in the period of time. The evidence nodes 1323 may be based on a level of compliance of the patient with one or more goals and/or schedule for the patient on a day as discussed elsewhere.

As illustrated in FIG. 13, the first state 1321a may correspond to the patient being in a healthy state on the first day. Additionally, as illustrated in FIG. 13, the second state 1321b may correspond to the patient being in an intermediate state on the first day. Also, as illustrated in FIG. 13, the third state 1321c may correspond to the patient being in a sick state on the first day. Furthermore, as illustrated in FIG. 13, the fourth state 1321d may correspond to the patient being in a healthy state on the second day. As illustrated in FIG. 13, the fifth state 1321e may correspond to the patient being in an intermediate state on the second day. Also, as illustrated in FIG. 13, the sixth state 1321f may correspond to the patient being in a sick state on the second day. It is to be understood that the states 1321 may correspond to different physical states of the patient.

A probability of the patient being in each of the states 1321 may be determined using Equation 2. The probability of the patient being in one of the states 1321 are represented as $P_H$, $P_I$, and $P_S$ in FIG. 13. $P_H$ may represent the probability of the patient being in the healthy state. $P_I$ may represent the probability of the patient being in the intermediate state. $P_S$ may represent the probability of the patient being in the sick state. For example, $P_H$ may represent the probability of the patient being in the first state 1321a on the first day and/or the fourth state 1321d on the second day. As another example, $P_I$ may represent the probability of the patient being in the second state 1321b on the first day and/or the fifth state 1321e on the second day. As yet another example, $P_S$ may represent the probability of the patient being in the third state 1321c on the first day and/or the sixth state 1321f on the second day.

A probability of the patient transitioning from one state 1321 on the first day to another state 1321 on the second day may be determined as discussed elsewhere. The probability of the patient transitioning from one state 1321 on the first day to another state 1321 on the second day are represented as $P_A$, $P_B$, $P_C$, $P_D$, $P_L$, $P_W$, $P_X$, $P_Y$, and $P_Z$ in FIG. 13. For example, $P_L$ may represent the probability of the patient transitioning from the first state 1321a on the first day to the fifth state 1321e on the second day. As another example, $P_X$ may represent the probability of the patient transitioning from the first state 1321a on the first day to the sixth state 1321f on the second day. As yet another example, $P_Z$ may represent the probability of the patient transitioning from the first state 1321a on the first day to the fourth state 1321d on the second day.

Likewise, $P_A$ may represent the probability of the patient transitioning from the second state 1321b on the first day to the fourth state 1321d on the second day. Also, $P_B$ may represent the probability of the patient transitioning from the second state 1321b on the first day to the fifth state 1321e on the second day. Furthermore, $P_D$ may represent the probability of the patient transitioning from the second state 1321b on the first day to the sixth state 1321f on the second day.

Figure 14:
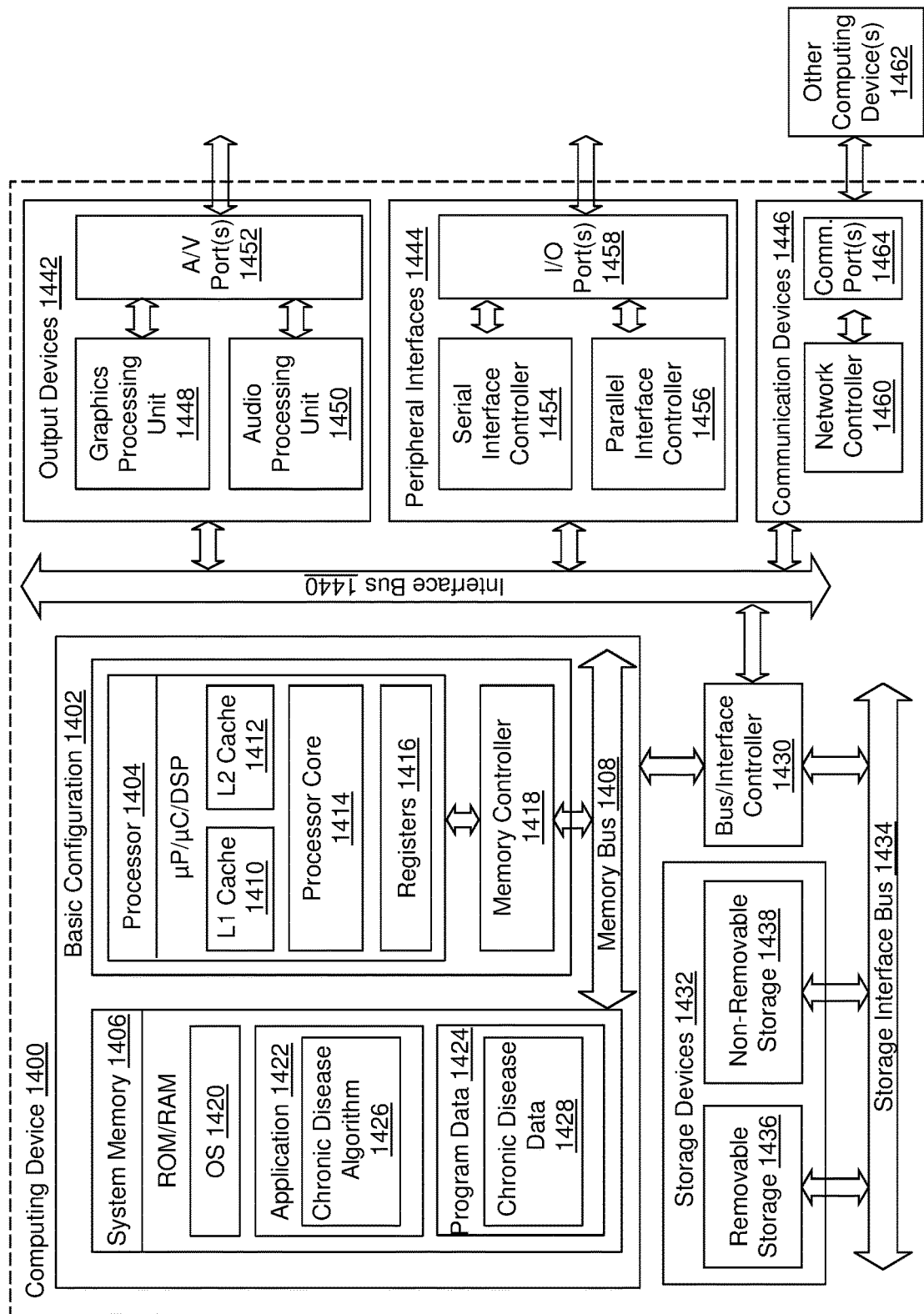
FIG. 14 is a block diagram of an example computing device.

Additionally, $P_W$ may represent the probability of the patient transitioning from the third state 1321c on the first day to the sixth state 1321f on the second day. Also, $P_Y$ may represent the probability of the patient transitioning from the third state 1321c on the first day to the fourth state 1321d on the second day. Likewise, $P_C$ may represent the probability of the patient transitioning from the third state 1321c on the first day to the fifth state 1321e on the second day FIG. 14 is a block diagram of an example of the computing device 1400, arranged in accordance with at least one embodiment of the present disclosure. The computing device 1400 may be used in some embodiments to perform or control performance of one or more of the methods and/or operations described herein. For instance, the computing device 1400 may be communicatively coupled to and/or included in or as the electronic device 102 described in relation to FIG. 1 to perform or control performance of the methods 200, 700, 800, 900, 1000, and 1100 of FIGS. 2, 8, 9, 10, and 11. In a basic configuration 1402, the computing device 1400 typically includes one or more processors 1404 and a system memory 1406. A memory bus 1408 may be used for communicating between the processor 1404 and the system memory 1406.

Depending on the desired configuration, the processor 1404 may be of any type including, such as a microprocessor (μP), a microcontroller (μC), a digital signal processor (DSP), or any combination thereof. The processor 1404 may include one or more levels of caching, such as a level one cache 1410 and a level two cache 1412, a processor core 1414, and registers 1416. The processor core 1414 may include an arithmetic logic unit (ALU), a floating point unit (FPU), a digital signal processing core (DSP Core), or any combination thereof. An example memory controller 1418 may also be used with the processor 1404, or in some implementations the memory controller 1418 may be an internal part of the processor 1404.

Depending on the desired configuration, the system memory 1406 may be of any type, such as volatile memory (such as RAM), non-volatile memory (such as ROM, flash memory, or the like), or any combination thereof. The system memory 1406 may include an operating system 1420, one or more applications 1422, and program data 1424. The application 1422 may include a chronic disease algorithm 1426 that is arranged to predict a likelihood of a patient experiencing an acute event in the near future, evaluate relative risk of under-diagnosis of a patient, evaluate and stratify a chronic care burden of a patient, generate a health risk score of a patient, and/or evaluate and stratify a lifestyle health compliance of a patient as described herein. The program data 1424 may include chronic disease data 1428 such as chronic data and/or EHR data that may be used to control aspects of the methods and/or operations described herein. In some embodiments, the application 1422 may be arranged to operate with the program data 1424 on the operating system 1420 to perform one or more of the methods and/or operations described herein, including those described with respect to FIGS. 2 and 7-11.

The computing device 1400 may include additional features or functionality, and additional interfaces to facilitate communications between the basic configuration 1402 and any other devices and interfaces. For example, a bus/interface controller 1430 may be used to facilitate communications between the basic configuration 1402 and one or more data storage devices 1432 via a storage interface bus 1434. The data storage devices 1432 may include removable storage devices 1436, non-removable storage devices 1438, or a combination thereof. Examples of removable storage and non-removable storage devices include magnetic disk devices such as flexible disk drives and hard-disk drives (HDDs), optical disk drives such as compact disk (CD) drives or digital versatile disk (DVD) drives, solid state drives (SSDs), and tape drives to name a few. Example computer storage media may include volatile and nonvolatile, removable and non-removable media implemented in any method or technology for storage of information, such as computer-readable instructions, data structures, program modules, or other data.

The system memory 1406, the removable storage devices 1436, and the non-removable storage devices 1438 are examples of computer storage media. Computer storage media includes, but is not limited to, RAM, ROM, EEPROM, flash memory or other memory technology, CD-ROM, digital versatile disks (DVDs) or other optical storage, magnetic cassettes, magnetic tape, magnetic disk storage or other magnetic storage devices, or any other medium which may be used to store the desired information and which may be accessed by the computing device 1400. Any such computer storage media may be part of the computing device 1400.

The computing device 1400 may also include an interface bus 1440 for facilitating communication from various interface devices (e.g., output devices 1442, peripheral interfaces 1444, and communication devices 1446) to the basic configuration 1402 via the bus/interface controller 1430. The output devices 1442 include a graphics processing unit 1448 and an audio processing unit 1450, which may be configured to communicate to various external devices such as a display or speakers via one or more A/V ports 1452. The peripheral interfaces 1444 include a serial interface controller 1454 or a parallel interface controller 1456, which may be configured to communicate with external devices such as input devices (e.g., keyboard, mouse, pen, voice input device, touch input device, and/or others), sensors, or other peripheral devices (e.g., printer, scanner, and/or others) via one or more I/O ports 1458. The communication devices 1446 include a network controller 1460, which may be arranged to facilitate communications with one or more other computing devices 1462 over a network communication link via one or more communication ports 1464.

Figure 15:
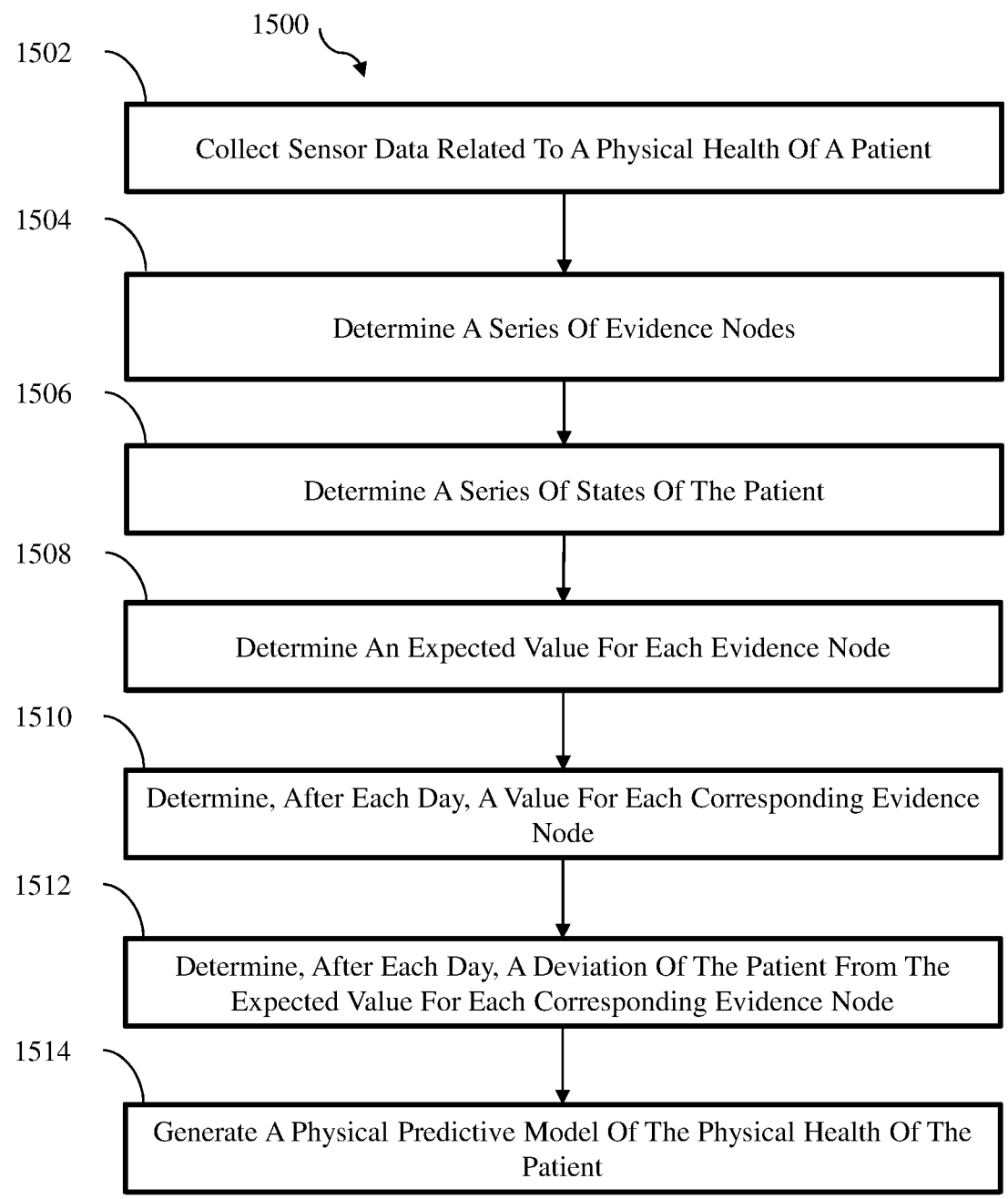
FIG. 15 is a flow diagram of an example method to generate a physical predictive model of a physical health of a patient.

FIG. 15 is a flow diagram of an example method 1500 to generate a physical predictive model of a physical health of a patient, arranged in accordance with at least one embodiment described herein. The method 1500 may be performed by a computer such as the computing device 1400 of FIG. 14. The method 1500 may be performed, in whole or in part, by the computing device. Alternatively or additionally, the method 1500 may be implemented by a processor device that performs or controls performance of one or more of the operations of the method 1500.

The method 1500 may include one or more of blocks 1502, 1504, 1506, 1508, 1510, 1512, and/or 1514. Although illustrated as discrete blocks, various blocks may be divided into additional blocks, supplemented with additional blocks, combined into fewer blocks, or eliminated, depending on the particular implementation. The method 1500 may begin at block 1502.

In block 1502 ("Collect Sensor Data Related To A Physical Health Of A Patient"), sensor data related to a physical health of a patient may be collected. In some embodiments, the sensor data may be collected by the computing device from the sensors. In these and other embodiments, the sensor data may pertain to, include, and/or indicate at least one of a diet pattern, a sleep pattern, an exercise pattern, an activity level, heart rate, posture, stress, blood pressure variation, blood glucose, heart rhythm, smoking status, pain level, and/or GPS data of the patient. Additionally or alternatively, the sensor data may be related to a mental health of the patient. Block 1502 may be followed by block 1504.

In block 1504 ("Determine A Series Of Evidence Nodes"), a series of physical evidence nodes may be determined. The physical evidence nodes may correspond with at least one of a schedule and one or more goals for the patient during a single day within a period of time. Block 1504 may be followed by block 1506.

In block 1506 ("Determine A Series Of States Of The Patient"), a series of physical states of the patient may be determined. Each physical state of the patient may be associated with a single physical evidence node. Block 1506 may be followed by block 1508.

In block 1508 ("Determine An Expected Value For Each Evidence Node") an expected value for each physical evidence node may be determined. The expected value may be determined based on a physical baseline of the patient. Block 1508 may be followed by block 1510.

In block 1510 ("Determine, After Each Day, A Value For Each Corresponding Physical Evidence Node"), a value for each corresponding physical evidence node may be determined after each day. Block 1510 may be followed by block 1512.

In block 1512 ("Determine, After Each Day, A Deviation Of The Patient From The Expected Value For Each Corresponding Physical Evidence Node"), a deviation of the patient from the expected value for each corresponding physical evidence node may be determined after each day. Block 1512 may be followed by block 1514.

In block 1514 ("Generate A Physical Predictive Model Of The Physical Health Of The Patient"), a physical predictive model of the physical health of the patient may be generated. The physical predictive model of the physical health of the patient may be generated based on the deviation of the patient from the expected value for each corresponding physical evidence node.

Figure 16:
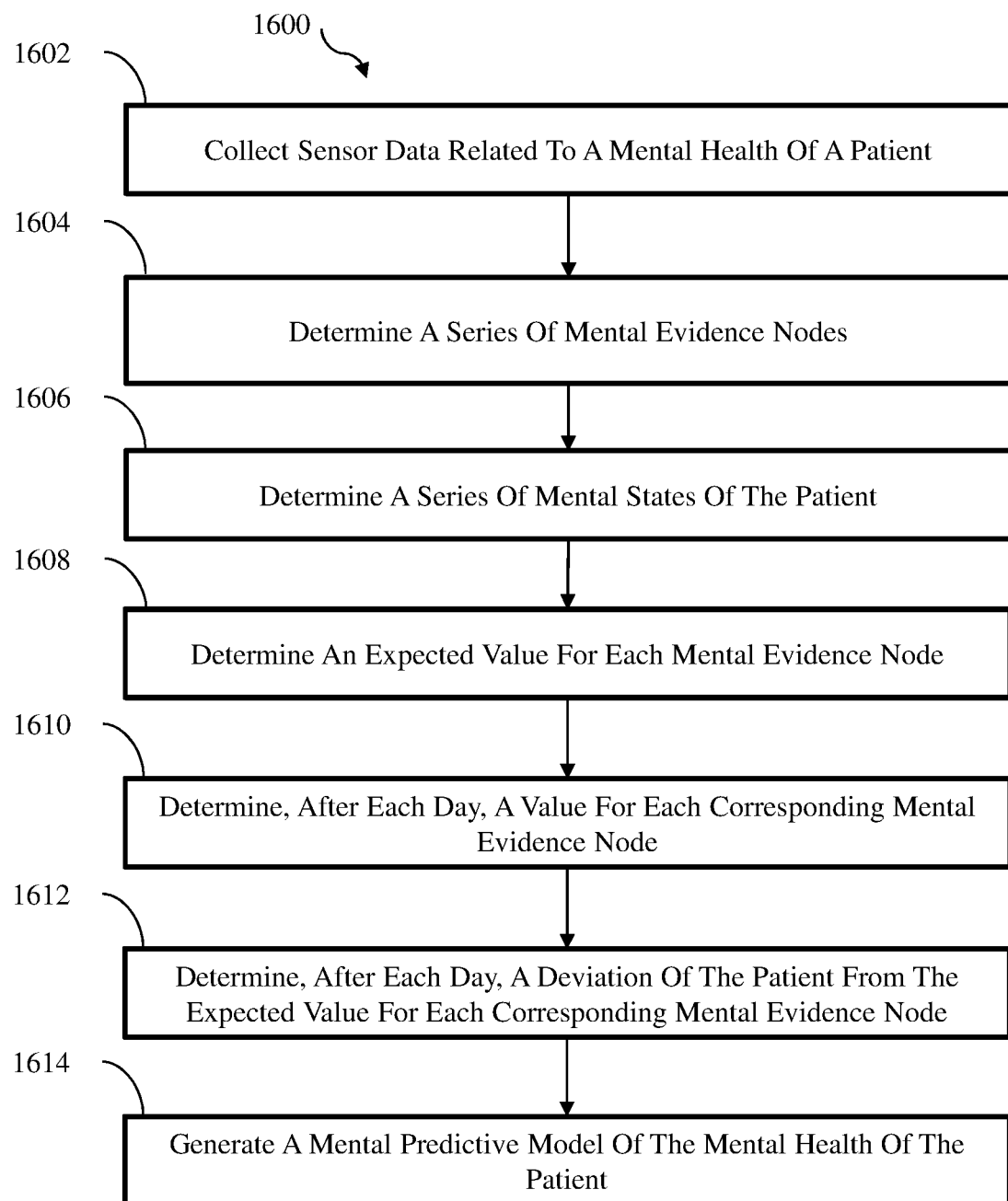
FIG. 16 is a flow diagram of an example method to generate a mental predictive model of a mental health of a patient, all arranged in accordance with at least one embodiment described herein.

FIG. 16 is a flow diagram of an example method 1600 to generate a mental predictive model of a mental health of a patient, arranged in accordance with at least one embodiment described herein. The method 1600 may be performed by a computer such as the computing device 1400 of FIG. 14. The method 1600 may be performed, in whole or in part, by the computing device. Alternatively or additionally, the method 1600 may be implemented by a processor device that performs or controls performance of one or more of the operations of the method 1600.

The method 1600 may include one or more of blocks 1602, 1604, 1606, 1608, 1610, 1612, and/or 1614. Although illustrated as discrete blocks, various blocks may be divided into additional blocks, supplemented with additional blocks, combined into fewer blocks, or eliminated, depending on the particular implementation. The method 1600 may begin at block 1602.

In block 1602 ("Collect Sensor Data Related To A Mental Health Of A Patient"), sensor data related to a mental health of a patient may be collected. In some embodiments, the sensor data may be collected by the computing device from the sensors. In these and other embodiments, the sensor data may pertain to, include, and/or indicate at least one of a diet pattern, a sleep pattern, an exercise pattern, an activity level, heart rate, posture, stress, blood pressure variation, blood glucose, heart rhythm, smoking status, pain level, and/or GPS data of the patient. Additionally or alternatively, the sensor data may be related to a mental health of the patient. Block 1602 may be followed by block 1604.

In block 1604 ("Determine A Series Of Mental Evidence Nodes"), a series of mental evidence nodes may be determined. The mental evidence nodes may correspond with at least one of a schedule and one or more goals for the patient during a single day within a period of time. Block 1604 may be followed by block 1606.

In block 1606 ("Determine A Series Of Mental States Of The Patient"), a series of mental states of the patient may be determined. Each mental state of the patient may be associated with a single mental evidence node. Block 1606 may be followed by block 1608.

In block 1608 ("Determine An Expected Value For Each Mental Evidence Node") an expected value for each mental evidence node may be determined. The expected value may be determined based on a mental baseline of the patient. Block 1608 may be followed by block 1610.

In block 1610 ("Determine, After Each Day, A Value For Each Corresponding Mental Evidence Node"), a value for each corresponding mental evidence node may be determined after each day. Block 1610 may be followed by block 1612.

In block 1612 ("Determine, After Each Day, A Deviation Of The Patient From The Expected Value For Each Corresponding Mental Evidence Node"), a deviation of the patient from the expected value for each corresponding mental evidence node may be determined after each day. Block 1612 may be followed by block 1614.

In block 1614 ("Generate A Mental Predictive Model Of The Mental Health Of The Patient"), a mental predictive model of the mental health of the patient may be generated. The mental predictive model of the mental health of the patient may be generated based on the deviation of the patient from the expected value for each corresponding mental evidence node.

The network communication link may be one example of a communication media. Communication media may typically be embodied by computer-readable instructions, data structures, program modules, or other data in a modulated data signal, such as a carrier wave or other transport mechanism, and may include any information delivery media. A "modulated data signal" may be a signal that includes one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR), and other wireless media. The term "computer-readable media" as used herein may include both storage media and communication media.

The computing device 1400 may be implemented as a portion of a small-form factor portable (or mobile) electronic device such as a cell phone, a personal data assistant (PDA), a personal media player device, a wireless web-watch device, a personal headset device, an application-specific device, or a hybrid device that include any of the above functions. The computing device 1400 may also be implemented as a personal computer including both laptop computer and non-laptop computer configurations.

The present disclosure is not to be limited in terms of the particular embodiments described herein, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that the present disclosure is not limited to particular methods, reagents, compounds, compositions, or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A system to evaluate and stratify a chronic care burden of a patient, the system comprising:
   one or more sensors configured to collect sensor data related to a quality of health of a patient that include at least one of an activity level, a heart rate, a posture, a stress, a blood pressure variation, a blood glucose, a heart rhythm, a smoking status, a pain level, and a GPS data;
   an electronic health record (EHR) database including patient data that indicates at least one of a biological profile of the patient, a psychological profile of the patient, a social profile of the patient, physician notes related to the biological profile of the patient, physician notes related to the psychological profile of the patient, baseline of sensor based data, and physician notes related to the social profile of the patient;
   a user device including a display, the user device configured to output an anatomically detailed human avatar to the patient via the display and to receive input from the patient that is effective to select one or more regions of the anatomically detailed human avatar where the patient is experiencing pain and a Visual Analog Scale (VAS) pain score according to a VAS pain scale of each of the selected one or more regions of the anatomically detailed human avatar; and
   a processor, coupled to the one or more sensors, the EHR database, and the user device, wherein the processor is configured to perform or control performance of executable operations including:
      receiving sensor data from the one or more sensors and VAS input provided by the patient through the anatomically detailed human avatar, the VAS input identifying at least one of a location of the patient's body experiencing pain, an amount of pain at the identified location, or a type of pain at the identified location;
      receiving patient input in response to one or more questions directed to a quality of health of the patient;
      generating a chronic care burden (CCB) score with a pre-defined risk stratification, wherein the CCB score is based on the patient data, the sensor data, the VAS input, and the patient input; and
      generating a CCB result, wherein the CCB result includes the CCB score and a risk stratification of the patient based on the pre-defined risk stratification and the CCB score;
      determining, based on the risk stratification, the present health risk assessment of the patient as one of Urgent, Very High, High, Moderately High, Moderate, or Low, wherein the present health risk assessment of the patient indicates whether the patient is likely to experience a rise in the chronic care burden associated with one or more chronic diseases in the intermediate future; and
      in response to determining that the present health risk assessment of the patient is Urgent, Very High, High, or Moderately High, providing the CCB result to a care-provider and alerting the care-provider to perform an in person examination of the patient as soon as possible to prevent or treat a likely rise in the chronic care burden associated with the one or more chronic diseases.

2. The system of claim 1, the executable operations further comprising combining the CCB score with a general self-reported health (GSRH) score received from the patient, wherein the risk stratification of the patient is determined based on the CCB score being combined with the GSRH score, and wherein a patient with a low GSRH score and a high CCB score is more likely to be at both a high acute risk as well as a high chronic care burden risk.

3. The system of claim 2, wherein the GSRH score is determined based on the VAS input and a status that indicates the quality of health of the patient is quantified along a scale of zero to ten.

4. The system of claim 3, wherein the GSRH score further includes health status of the patient values of at least one of "excellent", "very good", "good", "fair", and "poor" health status of the patient.

5. The system of claim 1, the executable operations further comprising combining the CCB score with at least one of an activity limitation score and a non-ordinal unhealthy days score, wherein the risk stratification of the patient is determined based on the CCB score being combined with at least one of the activity limitation score and the non-ordinal unhealthy days score.

6. The system of claim 1, wherein the VAS pain score is within a range of zero to one.

7. The system of claim 1, the executable operations further comprising combining the CCB score with a chronic disease calculator score, wherein the CCB result includes the result of the CCB score being combined with the chronic disease calculator score, and wherein the chronic disease calculator score identifies impending chronic care diseases with a sudden death burden.

8. The system of claim 1, wherein the one or more sensors are configured to monitor at least one of depression, hypertension, stroke risk, chronic obstructive pulmonary disease (COPD), diabetes, and fall risk of the patient.

9. The system of claim 8, wherein the one or more sensors are one or more on-body (wearable) devices.

10. The system of claim 8, wherein the one or more sensors are one or more off-body (non-wearable) devices.

11. The system of claim 1, wherein the CCB result includes one or more categories of at least one of a risk factor, a social life, and an approach toward health maintenance of the patient.

12. A method to evaluate and stratify a chronic care burden of a patient, the method comprising:
   collecting sensor data related to a quality of health of a patient that include at least one of an activity level, a heart rate, a posture, a stress, a blood pressure variation, a blood glucose, a heart rhythm, a smoking status, a pain level, and a GPS data;

collecting patient data that indicates at least one of a biological profile of the patient, a psychological profile of the patient, a social profile of the patient, physician notes related to the biological profile of the patient, physician notes related to the psychological profile of the patient, baseline of sensor based data, and physician notes related to the social profile of the patient;

outputting an anatomically detailed human avatar to the patient via a display of a user device;

receiving, via the user device, input from the patient that is effective to select one or more regions of the anatomically detailed human avatar where the patient is experiencing pain and a Visual Analog Scale (VAS) pain score according to a VAS pain scale of each of the selected one or more regions of the anatomically detailed human avatar;

receiving patient input in response to one or more questions directed to a quality of health of the patient;

generating a chronic care burden (CCB) score with a pre-defined risk stratification, wherein the CCB score is based on the patient data, the sensor data, the VAS input, and the patient input; and generating a CCB result, wherein the CCB result includes the CCB score and a risk stratification of the patient based on the pre-defined risk stratification and the CCB score;

determining, based on the risk stratification, the present health risk assessment of the patient as one of Urgent, Very High, High, Moderately High, Moderate, or Low, wherein the present health risk assessment of the patient indicates whether the patient is likely to experience a rise in the chronic care burden associated with one or more chronic diseases in the intermediate future; and in response to determining that the present health risk assessment of the patient is Urgent, Very High, High, or Moderately High, providing the CCB result to a care-provider and alerting the care-provider to perform an in person examination of the patient as soon as possible to prevent or treat a likely rise in the chronic care burden associated with the one or more chronic diseases.

13. The method of claim 12, further comprising combining the CCB score with a general self-reported health (GSRH) score received from the patient, wherein the risk stratification of the patient is determined based on the CCB score being combined with the GSRH score, and wherein a patient with a low GSRH score and a high CCB score is more likely to be at both a high acute risk as well as a high chronic care burden risk.

14. The method of claim 13, wherein the GSRH score is determined based on the VAS input and a status that indicates the quality of health of the patient is quantified along a scale of zero to ten.

15. The method of claim 14, wherein the GSRH score further includes health status of the patient values of at least one of "excellent", "very good", "good", "fair", and "poor" health status of the patient.

16. The method of claim 12, further comprising combining the CCB score with at least one of an activity limitation score and a non-ordinal unhealthy days score, wherein the risk stratification of the patient is determined based on the CCB score being combined with at least one of the activity limitation score and the non-ordinal unhealthy days score.

17. The method of claim 12, the method further comprising combining the CCB score with a chronic disease calculator score, wherein the CCB result further includes the result of the CCB score being combined with the chronic disease calculator score, and wherein the chronic disease calculator score identifies impending chronic care diseases with a sudden death burden.

18. The method of claim 12, wherein the CCB result includes one or more categories of at least one of a risk factor, a social life, and an approach toward health maintenance of the patient.

* * * * *